US012486275B2

(12) United States Patent
Kahn et al.

(10) Patent No.: US 12,486,275 B2

(45) Date of Patent: Dec. 2, 2025

(54) SUBSTITUTED PYRAZINO[2,1-C][1,2,4]TRIAZINES AS Wnt/CBP/CATENIN SIGNALING PATHWAY INHIBITORS

(71) Applicant: CITY OF HOPE, Duarte, CA (US)

(72) Inventors: Michael Kahn, Monrovia, CA (US); David Horne, Altadena, CA (US)

(73) Assignee: CITY OF HOPE, Duarte, CA (US)

( * ) Notice: Subject to any disclaimer, the term of this patent is extended or adjusted under 35 U.S.C. 154(b) by 658 days.

(21) Appl. No.: 17/801,646

(22) PCT Filed: Mar. 11, 2021

(86) PCT No.: PCT/US2021/021952

§ 371 (c)(1),
(2) Date: Aug. 23, 2022

(87) PCT Pub. No.: WO2021/183791

PCT Pub. Date: Sep. 16, 2021

(65) Prior Publication Data

US 2023/0132808 A1 May 4, 2023

Related U.S. Application Data

(60) Provisional application No. 62/988,822, filed on Mar. 12, 2020.

(51) Int. Cl.

*A61K 31/4985* (2006.01)
*C07D 487/04* (2006.01)
*C07D 519/00* (2006.01)

(52) U.S. Cl.

CPC ......... *C07D 487/04* (2013.01); *C07D 519/00* (2013.01)

(58) Field of Classification Search

CPC .......................... A61K 31/4985; C07D 487/04

(Continued)

(56) References Cited

U.S. PATENT DOCUMENTS 7,598,253 B2 10/2009 Kahn et al.
7,671,054 B1 3/2010 Moon et al.

(Continued)

FOREIGN PATENT DOCUMENTS

CN 1942472 2/2012
EP 3581183 A1 12/2019

(Continued)

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Hackam, et al. JAMA, 296(14), 2006, 1731-1732.*
International Preliminary Report on Patentability for International Application No. PCT/US2021/021958 mailed Sep. 22, 2022, 7 pages.

(Continued)

*Primary Examiner* — Douglas M Willis

(74) *Attorney, Agent, or Firm* — Aikin & Gallant, LLP

(57) ABSTRACT

Disclosed and provided herein are, inter alia, compounds of formula (Ia), (Ib), or (Ic):

(Ia)

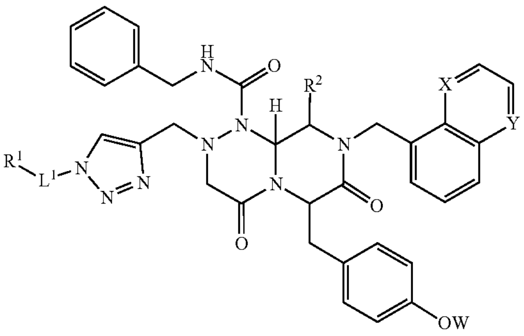

or (Ib)

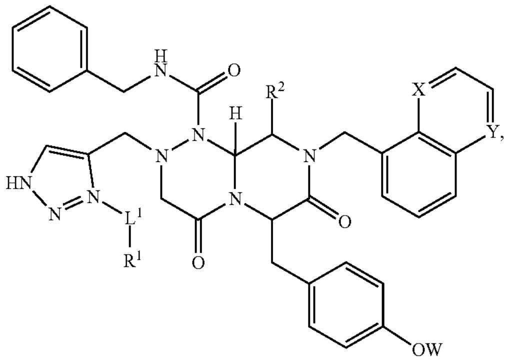

, or (Ic)

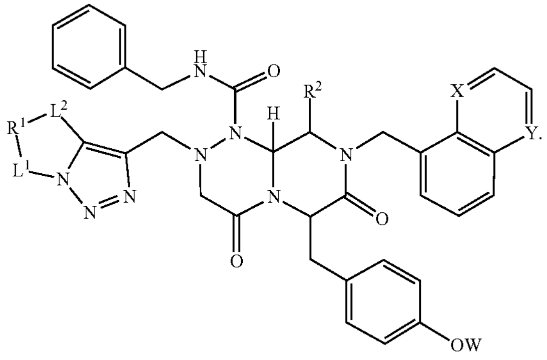

Figure 1:
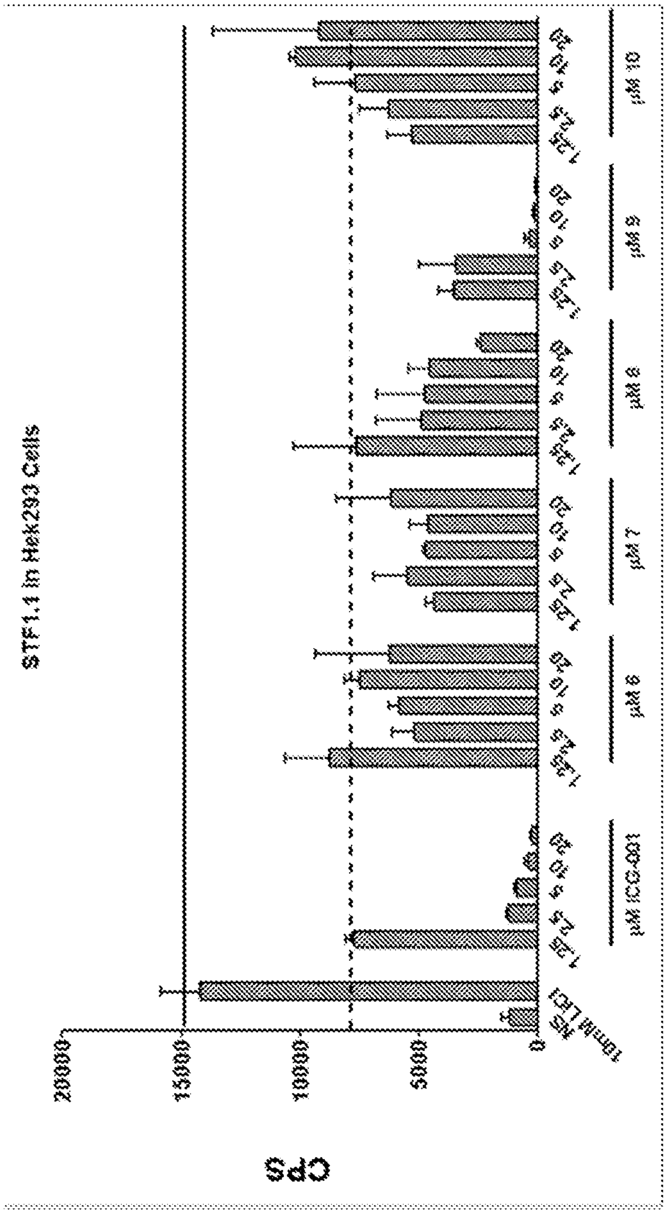

.

or pharmaceutically acceptable salts or stereoisomers thereof, and use thereof in methods for modulating CREB binding protein (CBP)/catenin signaling pathway activity and treating CBP/β-catenin mediated disorders.

20 Claims, 2 Drawing Sheets

(58) Field of Classification Search
USPC .......................................... 514/249; 544/350
See application file for complete search history.

(56) References Cited

U.S. PATENT DOCUMENTS

| | | | |
|---|---|---|---|
| 9,371,330 | B2 | 6/2016 | Kahn et al. |
| 2010/0029630 | A1 | 2/2010 | Moon et al. |
| 2010/0286094 | A1 | 11/2010 | Chung et al. |
| 2011/0294797 | A1 | 12/2011 | Moon et al. |
| 2014/0051706 | A1 | 2/2014 | Kouji et al. |
| 2015/0011759 | A1 | 1/2015 | Christie et al. |
| 2015/0175615 | A1 | 6/2015 | Inoue et al. |
| 2021/0317123 | A1 | 10/2021 | Ruan |

FOREIGN PATENT DOCUMENTS

| | | | | |
|---|---|---|---|---|
| WO | 2005116032 | A3 | 8/2005 | |
| WO | 200905139 | A2 | 4/2009 | |
| WO | 2009051397 | A2 | 4/2009 | |
| WO | 2012068299 | A2 | 5/2012 | |
| WO | WO-2021183791 | A1 * | 9/2021 | .............. A61P 37/00 |

OTHER PUBLICATIONS

International Preliminary Report on Patentability for International Application No. PCT/US2021/021952 mailed Sep. 22, 2022, 6 pages.
International Search Report and Written Opinion for International Application No. PCT/US2021/021958 mailed Jul. 21, 2021, 10 pages.
International Search Report and Written Opinion for International Application No. PCT/US2021/021952 mailed Jun. 2, 2021, 8 pages.
"PubChem-CID-140634489," <https://pubchem.ncbi.nlm.nih.gov/compound/140634489>, Dec. 6, 2019, 9 pages.
Akbar et al., "Aging immunity may exacerbate COVID-19: Increased general inflammation in aging inhibits immunity and affects responses to infections" Science, vol. 369 Issue 6501, Jul. 17, 2020, pp. 256-257.
Akcora et al., "Inhibition of canonical WNT signaling pathway by β-catenin/CBP inhibitor ICG-001 ameliorates liver fibrosis in vivo through suppression of stromal CXCL12" BBA—Molecular Basis of Disease, vol. 1864, Dec. 5, 2017, pp. 804-818.
Anderson et al., "The effect of influenza vaccination for the elderly on hospitalization and mortality: an observational study with a regression discontinuity design" Annals of Internal Medicine, vol. 172, Mar. 3, 2020, pp. 445-452.
Bem, "Pulmonary fibrosis secondary to COVID-19: a call to arms?" The Lancet Respiratory Medicine, vol. 8, Aug. 2020, pp. 750-752.
Borsa et al., "Modulation of asymmetric cell division as a mechanism to boost CD8+ T cell memory" Science Immunology, vol. 4 Issue 34, Apr. 12, 2019, pp. 1-15.
Ciocca et al., "Cutting edge: asymmetric memory t cell division in response to rechallenge" The Journal of Immunology, vol. 188 No. 9, Mar. 30, 2012, pp. 4145-4148.
Parmigiani et al., "Impaired antibody response to influenza vaccine in HIV-infected and uninfected aging women is associated with immune activation and inflammation" PLoS One, vol. 8 Issue 11, Nov. 13, 2013, pp. 1-13.
Emami et al., "A small molecule inhibitor of β-catenin/CREB-binding protein transcription" Proceedings of the National Academy of Sciences USA, vol. 101 No. 34, Aug. 24, 2004, pp. 12682-12687.
George et al., "Pulmonary fibrosis and COVID-19: the potential role for antifibrotic therapy" The Lancet Respiratory Medicine, vol. 8, May 15, 2020, pp. 807-815.
Ma et al., "Differential roles for the coactivators CBP and p300 on TCF/β-catenin-mediated survivin gene expression" Oncogene, vol. 24, Mar. 14, 2005, pp. 3619-3631.
Kahn, "Can we safely target the WNT pathway?" Nature Reviews Drug Discovery, vol. 13, Jul. 1, 2014, pp. 513-532.
Kim et al., "Activation of miR-21-Regulated pathways in immune aging selects against signatures characteristic of memory T cells" Cell Reports, vol. 25, Nov. 20, 2018, pp. 2148-2162.
Kim et al., "CBP/Catenin antagonists: targeting LSCs' Achilles heel" Experimental Hematology, vol. 52, May 4, 2017, pp. 1-11.
Kimura et al., "Safety, tolerability, and preliminary efficacy of the anti-fibrotic small molecule PRI-724, a CBP/β-Catenin inhibitor, in patients with hepatitis C virus-related cirrhosis: a single-center, open-label, dose escalation phase 1 trial" EBioMedicine, vol. 23, Aug. 19, 2017, pp. 79-87.
Kumar et al., "Preferential induction of EphB4 over EphB2 and its implication in colorectal cancer progression" Cancer Research, vol. 69 No. 9, Apr. 14, 2009, pp. 3736-3745.
Ljungberg et al., "Functions of the WNT signaling network in shaping host responses to infection" Frontiers in Immunology, vol. 10, Nov. 8, 2019, pp. 1-23.
Mannick et al., "TORC1 inhibition enhances immune function and reduces infections in the elderly" Science Translational Medicine, vol. 10 Issue 449, Jul. 11, 2018, pp. 1-10.
Mavigner et al., "Pharmacological modulation of the Wnt/β-Catenin pathway inhibits proliferation and promotes differentiation of long-lived memory $CD4^+$ T cells in antiretroviral therapy-suppressed simian immunodeficiency virus-infected macaques" Journal of Virology, vol. 94 Issue 1, Dec. 12, 2019, pp. 1-15.
Merad et al., "Pathological inflammation in patients with COVID-19: a key role for monocytes and macrophages" Nature Reviews Immunology, vol. 20, May 6, 2020, pp. 355-362.
Morrot "Asymmetric cell division regulates the transcriptional balance controlling memory fate decisions in T cells" Annals of Translational Medicine, vol. 5, Mar. 1, 2017, pp. 1-2.
Hirakawa et al., "β-catenin signaling inhibitors ICG-001 and C-82 improve fibrosis in preclinical models of endometriosis" Scientific Reports, vol. 9, Dec. 27, 2019, pp. 1-11.
Shiozaki et al., "Discovery of (1S,2R,3R)-2,3-Dimethyl-2-phenyl-1-sulfamidocyclopropanecarboxylates: Novel and Highly Selective Aggrecanase Inhibitors" Journal of Medicinal Chemistry, vol. 54, Mar. 21, 2011, pp. 2839-2863.
Slutsky et al., "Ventilator-induced lung injury" New England Journal of Medicine, vol. 369, Nov. 28, 2013, pp. 2126-2136.
Thomas et al., "Kat3 coactivators in somatic stem cells and cancer stem cells: biological roles, evolution and pharmacologic manipulation" Cell Biology and Toxicology, vol. 32, Mar. 23, 2016, pp. 61-81.
Veltri et al., "Concise review: Wnt signaling pathways in skin development and epidermal stem cells" Stem Cells Express, vol. 36, Oct. 19, 2017, pp. 22-35.
Verbist et al., "Metabolic maintenance of cell asymmetry following division in activated T lymphocytes" Nature, vol. 532, Apr. 21, 2016, pp. 389-404.
Willyard "Ageing and COVID vaccines" Nature, vol. 586, Oct. 15, 2020, pp. 352-354.
Xiao et al., "Wnt/β-catenin regulates blood pressure and kidney injury in rats" BBA—Molecular Basis of Disease, vol. 1865 Issue 6, Jan. 30, 2019, pp. 1313-1322.
Zhao et al., "An essential role for Wnt/β-catenin signaling in mediating hypertensive heart disease" Scientific Reports, vol. 8, Jun. 12, 2018, pp. 1-14.
Nusse et al., "Many Tumors Induced by the Mouse Mammary Tumor Virus Contain a Provirus Integrated in the Same Region of the Host Genome," Cell vol. 31, Nov. 1982; pp. 99-109.
Baker et al., "Molecular cloning of sequences from wingless, a segment polarity gene is *Drosophila*: the spatial distribution of a transcript in embryos," The EMBO Journal, vol. 6, No. 6, 1987, pp. 1765-1773.
Logan et al., "The Wnt Signaling Pathway in Development and Disease," Annu. Rev. Cell Dev. Biol. 2004, 20, pp. 781-810.
Van Amerongen et al., "Towards an integrated view of Wnt signaling in development," Development 136, 2009, pp. 3205-3214.
Alonso et al., "Stem cells in the skin: waste not, Wnt not," Genes & Development 17, 2003, pp. 1189-1200.
Pinto, et al., "Wnt control of stem cells and differentiation in the intestinal epithelium," Experimental Cell Research 306, (2005), 357-363.

(56) References Cited

OTHER PUBLICATIONS

Nemeth et al., "β-Catenin Expression in the Bone Marrow Microenvironment Is Required for Long-Term Maintenance of Primitive Hematopoietic Cells," Stem Cells, 2009, 27, pp. 1109-1119.
Reya et al., "Wnt signaling in stem cells and cancer," Nature, vol. 434, Apr. 14, 2005, pp. 843-850.
Groden et al., "Identification and Characterization of the Familial Adenomatous Polyposis Coli Gene," Cell, vol. 66, Aug. 9, 1991, pp. 589-600.
Kinzler et al., "Identification of FAP Locus Genes from Chromosome 5q21," Science, vol. 253, Aug. 9, 1991; pp. 661-665.
Nishisho et al., "Mutations of Chromosome 5q21 Genes in FAP and Colorectal Cancer Patients," Science, vol. 253, Aug. 9, 1991; 253:, pp. 665-669.
Morin, et al., "Activation of β-Catenin-Tcf Signaling in Colon Cancer by Mutations in B-Catenin or APC," Science, vol. 275, Mar. 21, 1997, pp. 1787-1790.
Rubinfeld et al., "Stabilization of β-Catenin by Genetic Defects in Melanoma Cell Lines," Science, vol. 275, Mar. 21, 1997, pp. 1790-1792.
Herr et al., "WNT secretion and signalling in human disease," Trends in Molecular Medicine, vol. 18, No. 8, Aug. 2012, pp. 483-493.
Han, "Functional Genomic Studies: Insights into the Pathogenesis of Liver Cancer," Annual Rev. Genom. Hum. Genet., 2012, 13, pp. 171-205.
Sastre-Perona, et al., "Role of the Wnt pathway in thyroid cancer," Frontiers in Endocrinology (Lausanne), vol. 3, Article 31, Feb. 29, 2012, pp. 1-10.
Gatcliffe, et al., "Wnt signaling in ovarian tumorigenesis," Int. J. Gynecol. Cancer, 2008; 18(5): 954-962.
Caldwell et al., "The Wnt Antagonist sFRP1 in Colorectal Tumorigenesis," Cancer Research 64, Feb. 1, 2004, pp. 883-888.
Lee et al., "Expression of the secreted frizzled-related protein gene family is downregulated in human mesothelioma," Oncogene 23, 2004, pp. 6672-6676.
Zou et al., "Aberrant methylation of secreted frizzled-related protein genes in esophageal adenocarcinoma and Barrett's esophagus," Int. J. Cancer, vol. 116, 2005, pp. 584-591.
Rhee et al., "Wnt and frizzled receptors as potential targets for immunotherapy in head and neck squamous cell carcinomas," Oncogene 21, 2002, pp. 6598-6605.
Milovanovic et al., "Expression of Wnt genes and frizzled 1 and 2 receptors in normal breast epithelium and infiltrating breast carcinoma," International Journal of Oncology 25, 2004, pp. 1337-1342.
Okino et al., "Up-regulation and overproduction of DVL-1, the human counterpart of the *Drosophila* dishevelled gene, in cervical squamous cell carcinoma," Oncology Reports 10, 2003, pp. 1219-1223.
Uematsu et al., "Wnt Pathway Activation in Mesothelioma: Evidence of Dishevelled Overexpression and Transcriptional Activity of β-Catenin," Cancer Research 63, Aug. 1, 2003, pp. 4547-4551.
Uematsu et al., "Activation of the Wnt pathway in non small cell lunch cancer: evidence of dishevelled overexpression," Oncogene (2003) 22, pp. 7218-7221.
Tang et al., "Inhibition of CREB binding protein-beta-catenin signaling down regulates CD133 expression and activates PP2A-PTEN signaling in tumor initiating liver cancer cells," Cell Communication and Signaling, 2018, 16:9, pp. 1-12.
Higuchi et al., "Specific Direct Small Molecule p300/β-Catenin Antagonists Maintain Stem Cell Potency," Current Molecular Pharmacology, 2016, 9, pp. 272-279.
Ramirez-Montagut et al., "Immunity to melanoma: unraveling the relation of tumor immunity and autoimmunity," Oncogene (2003) 22, pp. 3180-3187.
Sawaya et al., "Risk of Cervical Cancer Associated with Extending the Interval between Cervical-Cancer Screenings," The New England Journal of Medicine, vol. 349, No. 16, Oct. 16, 2003, pp. 1501-1509.
Rosen et al., "Low membranous expression of β-catenin and high mitotic count predict poor prognosis in endometrioid carcinoma of the ovary," Modern Pathology (2010) 23, pp. 113-122.
Gregory et al., "Non-hematopoietic bone marrow stem cells: Molecular control of expansion and differentiation," Experimental Cell Research 306 (2005), pp. 330-335.
Fukui et al., "Transcriptional silencing of secreted frizzled related protein 1 (SFRP1) by promoter hypermethylation in non-small lung cancer," Oncogene (2005) 24, pp. 6323-6327.
Gerrard, Diane et al.; "Disruption of Broad Epigenetic Domains in PDAC Cells by HAT Inhibitors;" retrieved online: Epigenomes 2019, 3, 11; doi:10.3390/epigenomes3020011; www.mdpi.com/journal/epigenomes; MDPI, Basel, Switzerland; Jun. 2, 2019; pp. 1-18.
Gravesen, Eva et al.; "Effect of inhibition of CBP-coactivated β-catenin-mediated Wnt signalling in uremic rats with vascular calcifications;" retrieved online: https://doi.org/10.1371/journal.pone.0201936; PLOS One; Utrecht, Netherlands; Aug. 3, 2018; pp. 1-21.
Kuchibhotla, Virinchi N. S. et al.; "Inhibition of β-catenin/CBP signalling improves airway epithelial barrier function and suppresses CCL20 release;" Wiley: European Journal of Allergy and Clinical Immunology "EAACI"; retrieved online: 13989995, 2020, 7; https://onlinelibrary.wiley.com/doi/10.1111/ by City of Hope—Lee Graff Medic, Wiley Online Library on Apr. 8, 2024; pp. 14216-14219.
Lewis, Amy et al.; "Small-molecule Wnt inhibitors are a potential novel therapy for intestinal fibrosis in Crohns disease;" retrieved online: https://doi.org/10.1042/CS20210889; http://portlandpress.com/clinsci/article-pdf/136/19/1405/938187/cs-2021-0889.pdf by City of Hope National Medical Center; Clinical Science (2022) 136; Portland Press; Oct. 14, 2022; pp. 1405-1423.
Zhou, Yufan et al.; "3D Chromatin Alteration by Disrupting β-Catenin/CBP Interaction Is Enriched with Insulin Signaling in Pancreatic Cancer;" retrieved online: https://doi.org/10.3390/cancers 16122202; https://www.mdpi.com/journal/cancers; Cancers 2024, 16, 2202; pp. 1-14.

* cited by examiner

SUBSTITUTED PYRAZINO[2,1-C][1,2,4]TRIAZINES AS Wnt/CBP/CATENIN SIGNALING PATHWAY INHIBITORS

CROSS-REFERENCE TO RELATED APPLICATION

This application is a 371 National Stage Entry of International Application No. PCT/US2021/021952 filed Mar. 11, 2021, which claims the benefit of priority to U.S. Provisional Patent Application Ser. No. 62/988,822, filed Mar. 12, 2020, which are hereby incorporated by reference in their entirety.

BACKGROUND

Wnt/β-catenin signaling is an evolutionarily conserved pathway and it plays indispensable roles in both embryonic development and adult homeostasis. The Wnt/β-catenin network was first reported in 1982 with identification of mouse proto-oncogene int1 also known as Wnt1). Later the homolog of int1, Wingless (Wg) from *Drosophila melanogaster*, was identified to promote wing development in fruit flies (Nusse R. et al., *Cell,* 1982; 31:99-109; Baker N. E., *EMBO J.,* 1987; 6:1765-1773). Since then, accumulative studies have reported essential roles of the Wnt/β-catenin signaling in development of various organs and tissues such as the brain, spinal cord, kidney, heart, liver, lungs, limbs and eyes (Logan C. Y. et al., *Annu Rev Cell Dev Biol.* 2004; 20:781-810; van Amerongen R. et al., *Development,* 2009; 136:3205-3214). In addition, the Wnt/β-catenin signaling also plays crucial roles in adult homeostasis such as regeneration of skin, gut, hair and bone marrow (Alonso L. et al., *Genes Dev.* 2003; 17:1189-1200; Pinto D. et al., *Exp Cell Res,* 2005; 306:357-363; Nemeth M. J. et al., *Stem Cells,* 2009; 27:1109-1119; Reya T. et al., *Nature,* 2005; 434:843-850).

Wnt/β catenin signaling dysregulation/hyperactivity has been implicated in a range of disease states including diabetes, cancer, and fibrosis. In 1991, genetic mutations in the tumor suppressor APC were first found to be associated with colorectal cancer (Groden J. et al., *Cell,* 1991; 66:589-600; Kinzler K. W. et al., *Science,* 1991; 253:661-665; Nishisho I. et al., *Science,* 1991; 253:665-669). Genetic mutations of β-catenin that abnormally activate the Wnt/β-catenin signaling were also observed in colorectal cancer (Morin P. J. et al., *Science,* 1997; 275:1787-1790). Importantly, effects of mutations in the Wnt/β-catenin cascade are not limited to colorectal cancers. For instance, messenger RNA splicing and missense mutations in the β-catenin gene were described in melanoma progression (Rubinfeld B. et al., *Science,* 1997; 275:1790-1792; Herr P. et al., *Trends in Mol Med.,* 2012; 18:483-493) and other solid tumors, such as liver cancer (Han Z G., *Annual Rev Genomics Hum Genet.* 2012; 13:171-205), thyroid tumors (Sastre-Perona A. et al., *Front Endocrinol* (Lausanne) 2012; 3:31) and ovarian neoplasms (Gatcliffe T. A. et al., *Int J Gynecol Cancer,* 2008; 18:954-962).

Besides genetic mutations of the Wnt/β-catenin cascade, abnormal expression of the signaling proteins by epigenetic alteration is also involved in various types of cancer. For instance, the reduced activity or absence of extracellular Wnt antagonist, the secreted Frizzled-related proteins (SFRPs) has been reported in colorectal, breast, prostate, and lung cancers (Caldwell G. M. et al., *Cancer Res,* 2004; 64:883-888; Lee A. Y. et al, *Oncogene,* 2005; 24:6323-6327; Zou H. et al., *Int J Cancer,* 2005; 116:584-591). Increased expression of Wnt ligands and Dvl has been demonstrated to be associated with many types of cancer as well (Rhee C. S. et al., *Oncogene,* 2002; 21:6598-6605; Milovanovic T. et al., *Int J Oncol,* 2004; 25:1337-1342; Okino K. et al., *Oncol Rep.* 2003; 10:1219-1223; Uematsu K. et al., *Cancer Res.* 2003; 63:4547-4551; Uematsu K. et al., *Oncogene,* 2003; 22:7218-7221).

The recent studies have shown that the inhibitors of CBP-β-catenin signaling pathway significantly reduced CD133 (tumor initiating liver cells, TICs) expression and anchorage independent growth in human hepatoblastoma cell line HepG2 and murine TICs (Tang et al., *Cell Communication and Signaling* 16:9, 2018).

Given the critical roles of Wnt/β-catenin pathway in cancer and other disorders, there is an unmet need for therapeutic agents capable of modulating this target. The proposed compounds have the potential to deliver potent, small molecule inhibitors of Wnt/β-catenin pathway.

SUMMARY

Provided herein, inter alia, are small molecule inhibitors of CREB binding protein (CBP)/catenin signaling pathway, pharmaceutical compositions comprising these compounds, and the use of these compounds for the treatment of CBP/catenin signaling pathway modulated disease or disorder, in addition to cosmeceutical uses thereof.

Aspects of the invention may include any one or more of the following clauses. In an aspect, provided is a compound of structural formulae (Ia) (Ib), and (Ic):

(Ia)

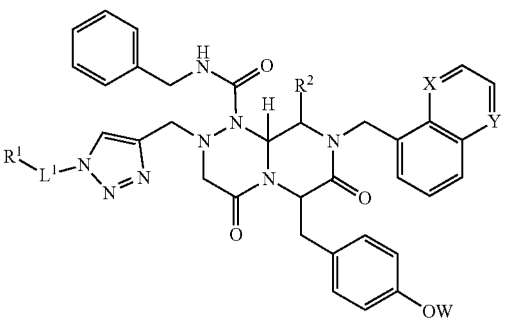

or (Ib)

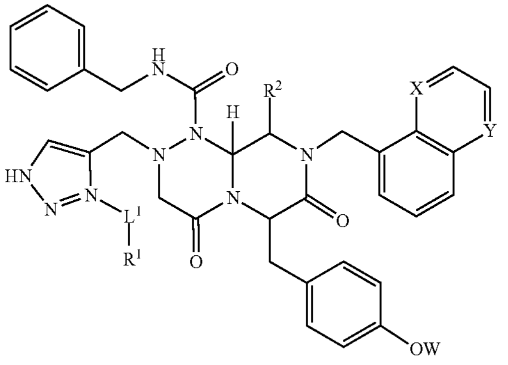

or

-continued (Ic)

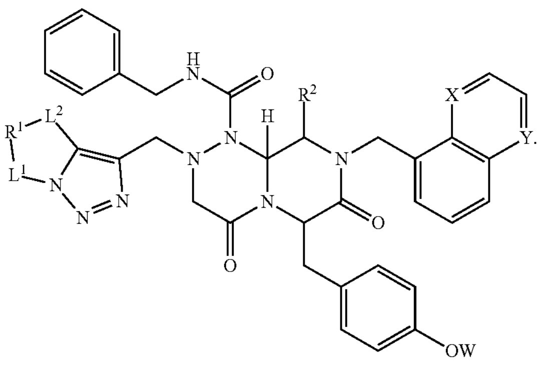

X is N or —CH. Y is N or —CH. $L^1$ and $L^2$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. $R^1$ is independently hydrogen, halogen, $—CX^1_3$, $—CHX^1_2$, $—CH_2X^1$, $—OCX^1_3$, $—OCHX^1_2$, $—OCH_2X^1$, —CN, $—S(O)_2R^{1A}$, $—SR^{1A}$, $—S(O)R^{1A}$, $—SO_2NR^{1A}R^{1B}$, $—NHC(O)NR^{1A}R^{1B}$, $—N(O)_2$, $—NR^{1A}R^{1B}$, $—NHNR^{1A}R^{1B}$, $—C(O)R^{1A}$, $—C(O)—OR^{1A}$, $—C(O)NR^{1A}R^{1B}$, $—C(O)NHNR^{1A}R^{1B}$, $—OR^{1A}$, $—NR^{1A}SO_2R^{1B}$, $—NR^{1A}C(O)R^{1B}$, $—NR^{1A}C(O)OR^{1B}$, $—NR^{1A}OR^{1B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen or substituted or unsubstituted $C_1$-$C_4$ alkyl. $R^{1A}$ and $R^{1B}$ are independently hydrogen, $—CX^1_3$, $—CHX^1_2$, $—CH_2X^1$, —C(O)OH, $—C(O)NH_2$, —OH, $—NH_2$, —COOH, $—CONH_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)OH, —NHOH, $—OCX^1_3$, $—OCHX^1_2$, $—OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{1A}$ and $R^{1B}$ substituents bonded to the same nitrogen atom may optionally be joined to form a substituted or unsubstituted heterocycloalkyl or substituted or unsubstituted heteroaryl. $X^1$ is halogen. W is hydrogen, phosphate or phosphate salt, or an ester of an alkyl acid or of a fatty acid, preferably hydrogen.

2. The compound of clause 1, wherein the compound is of the formula (Ia') or (Ib'):

(Ia')

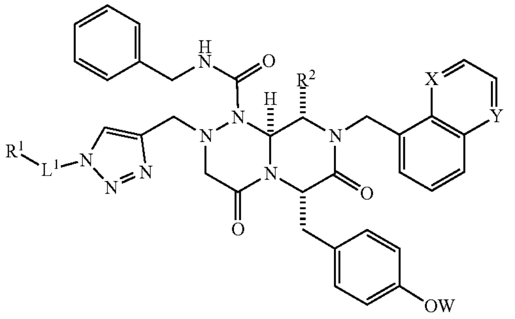

or (Ib')

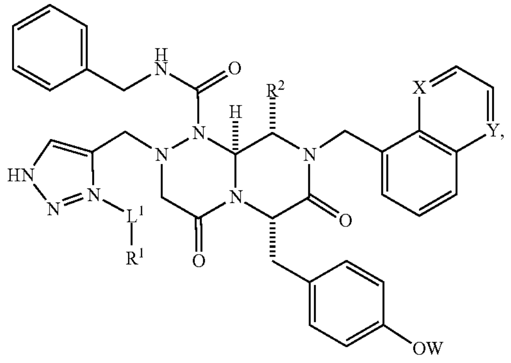

or (Ic')

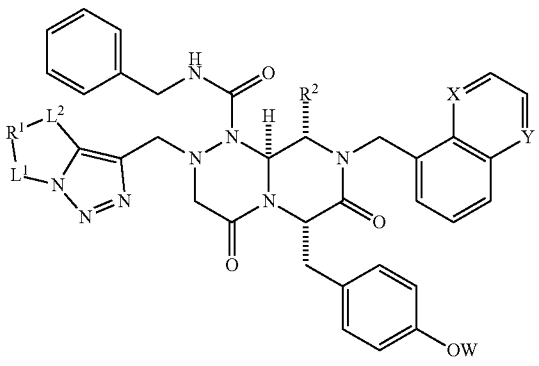

or a pharmaceutically acceptable salt thereof.

3. The compound of clause 1 or 2, wherein the compound is of the formula (IIa) or (IIb):

(IIa)

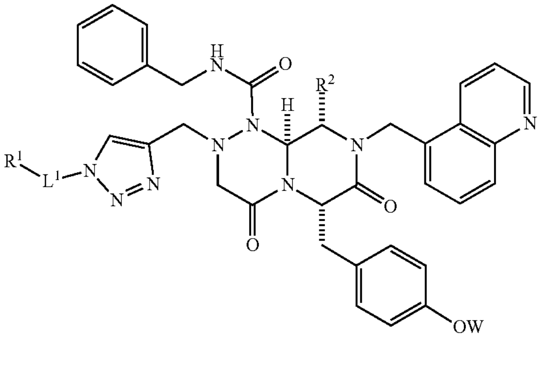

or

-continued
(IIb)
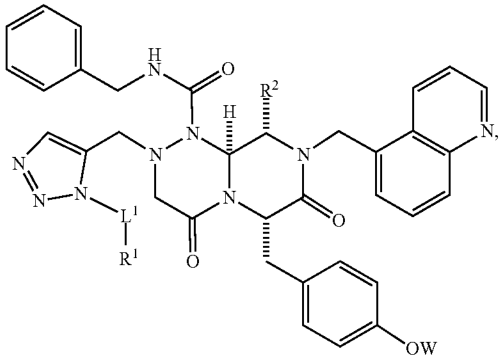
or
(IIc)
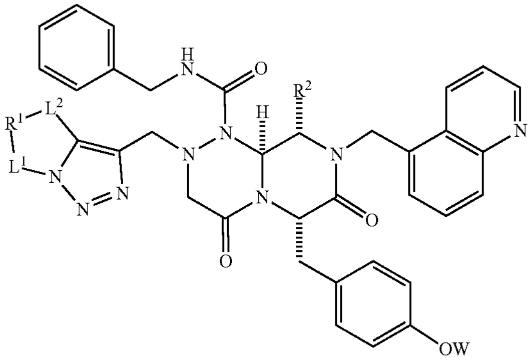
or a pharmaceutically acceptable salt thereof.
4. The compound of clause 1 or 2, wherein the compound is of the formula (IIIa) or (IIIb):
(IIIa)
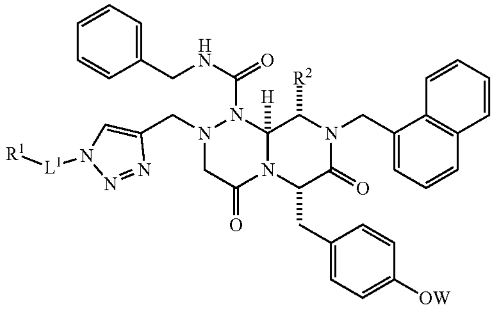
or
(IIIb)
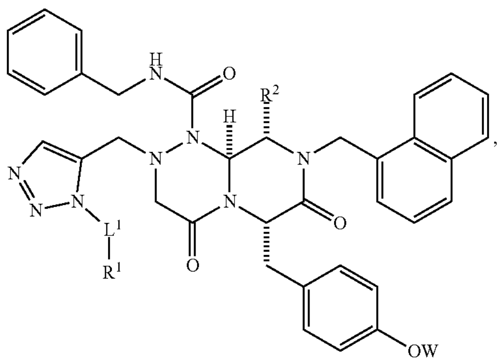
, or
-continued
(IIIc)
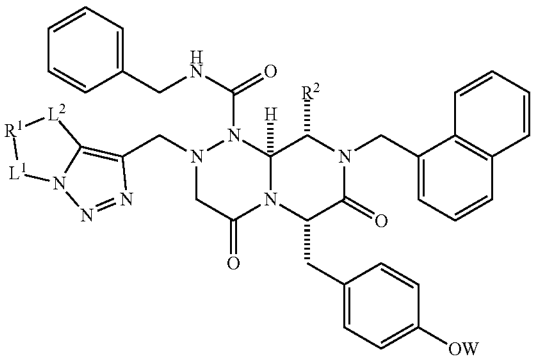
or a pharmaceutically acceptable salt thereof.
5. The compound of clause 1 or 2, wherein the compound is of the formula (IVa) or (IVb):
(IVa)
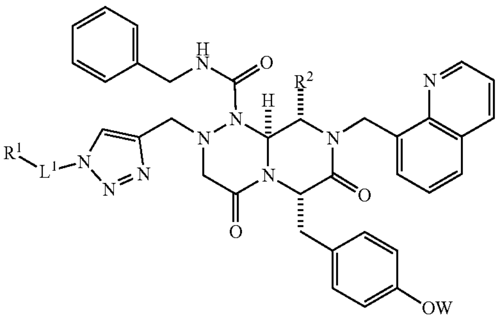
or
(IVb)
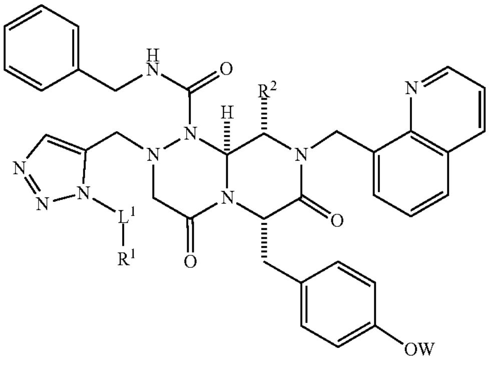
, or -continued (IVc)

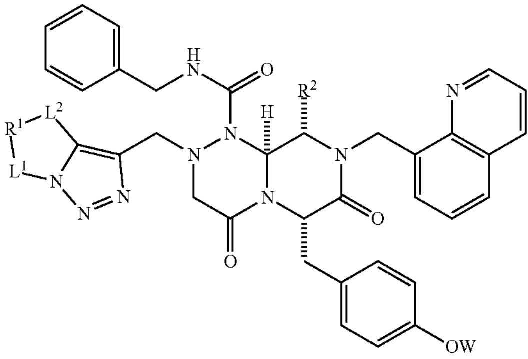

or a pharmaceutically acceptable salt thereof.

6. The compound of any one of clauses 1 to 5, wherein $L^1$ or $L^2$ is $(CH_2)n$, and n is an integer from 0 to 4.

7. The compound of any one of clauses 1 to 6, wherein $R^2$ is hydrogen, $—CH_3$, or $—CH_2CH_3$.

8. The compound of any one of clauses 1 to 7, wherein $L^1$ is methylene or ethylene and $L^2$ is a bond.

9. The compound of any one of clauses 1 to 8, wherein $R^1$ is halogen, $—CX^1_3$, $—CHX^1_2$, $—CH_2X^1$, $—OCX^1_3$, $—OCHX^1_2$, $—OCH_2X^1$, —CN, $—S(O)_2R^{1A}$, $—SR^{1A}$, $—S(O)R^{1A}$, $—SO_2NR^{1A}R^{1B}$, $—NHC(O)NR^{1A}R^{1B}$, $—N(O)_2$, $—NR^{1A}R^{1B}$, $—NHNR^{1A}R^{1B}$, $—C(O)R^{1A}$, $—C(O)—OR^{1A}$, $—C(O)NR^{1A}R^{1B}$, $—C(O)NHNR^{1A}R^{1B}$, $—OR^{1A}$, $—NR^{1A}SO_2R^{1B}$, $—NR^{1A}C(O)R^{1B}$, $—NR^{1A}C(O)OR^{1B}$, $—NR^{1A}OR^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl 10. The compound of clause 9, wherein $R^1$ is —CN, —OH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

11. The compound of clause 1, wherein the compound is:

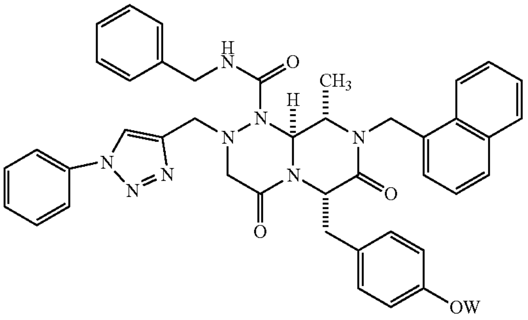

,

-continued

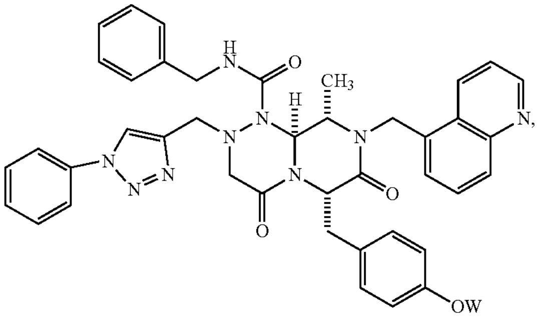

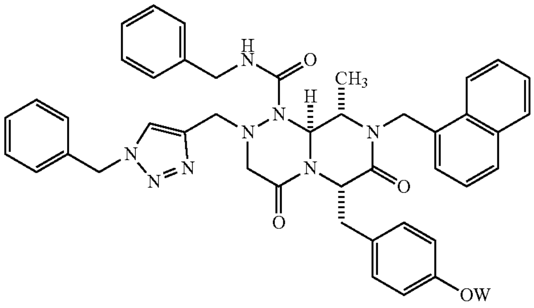

,

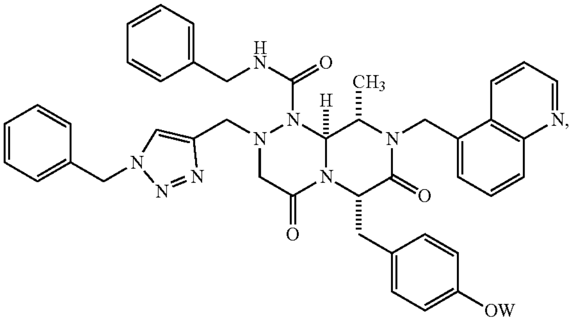

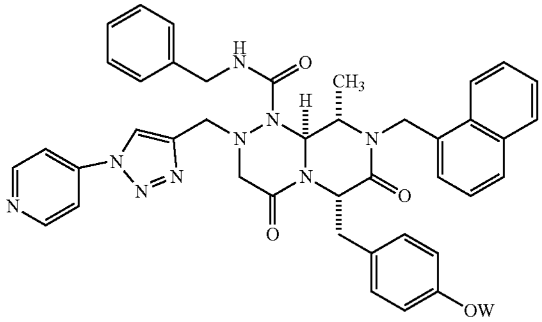

,

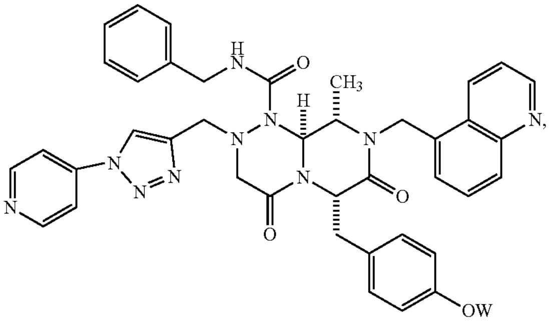

-continued
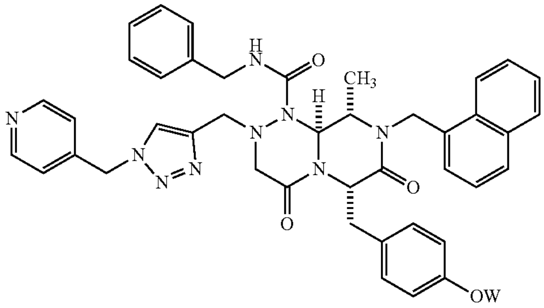
,
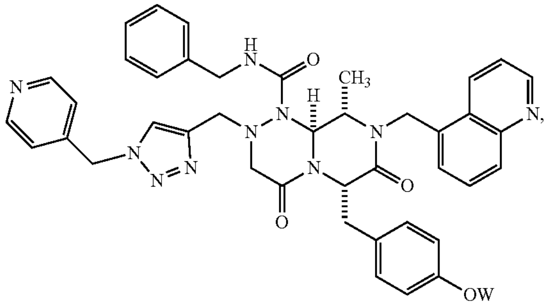
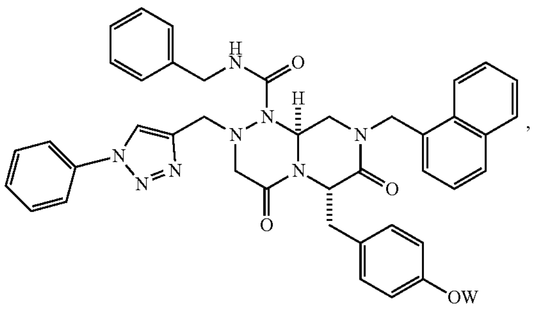
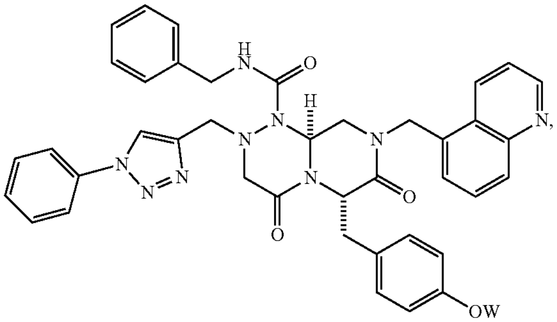
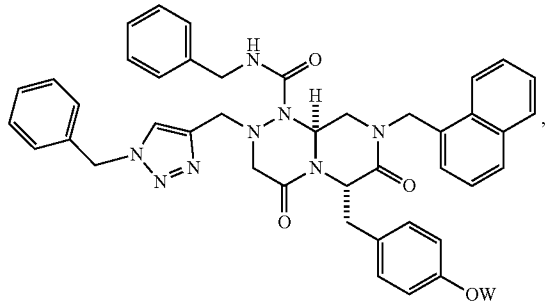
-continued
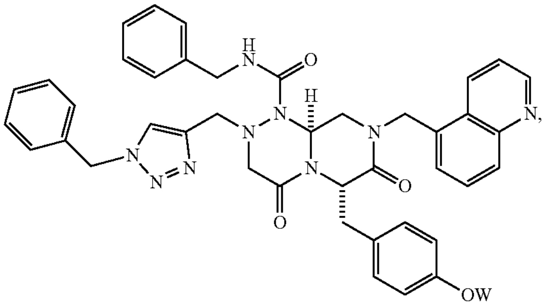
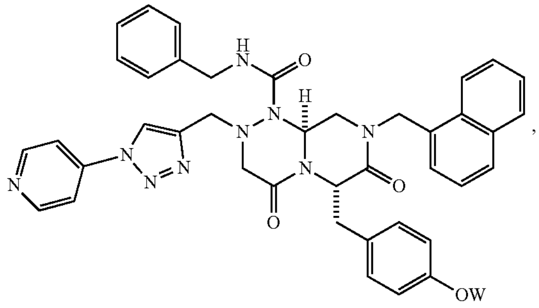
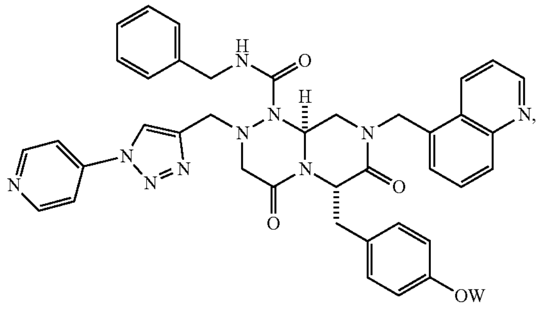
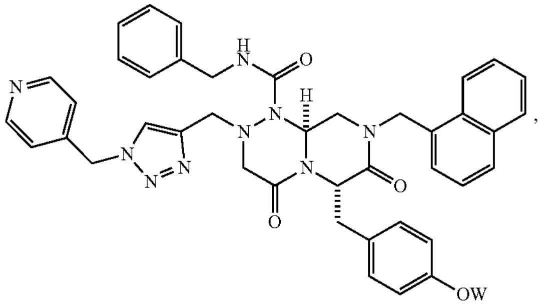
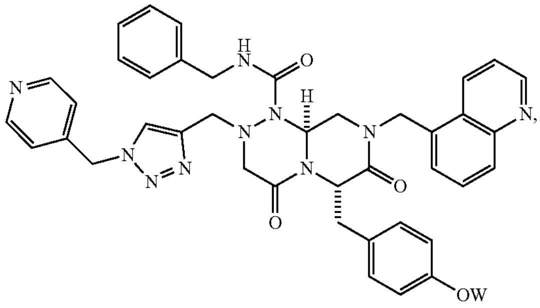

-continued
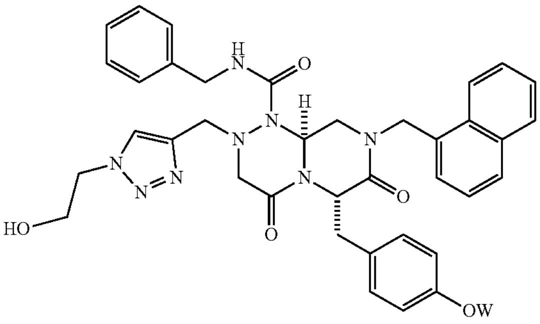
,
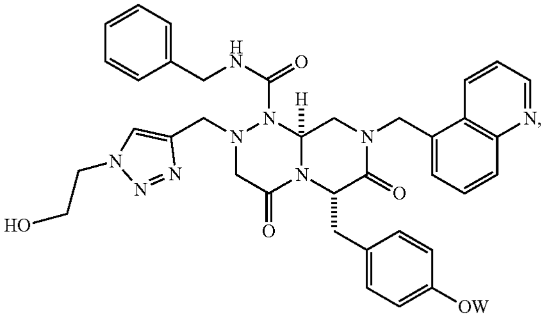
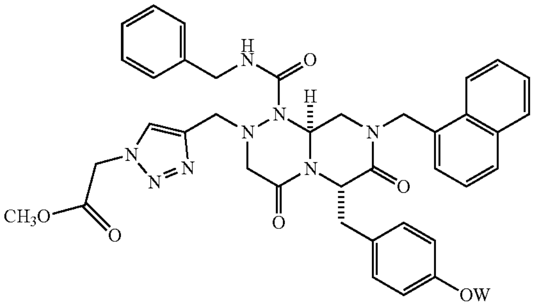
,
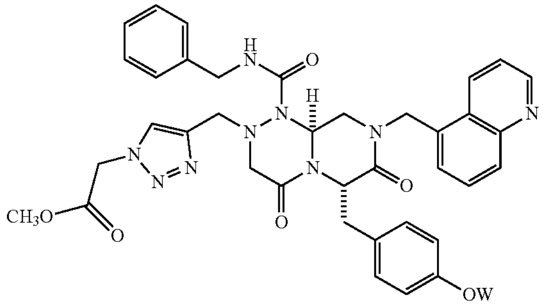
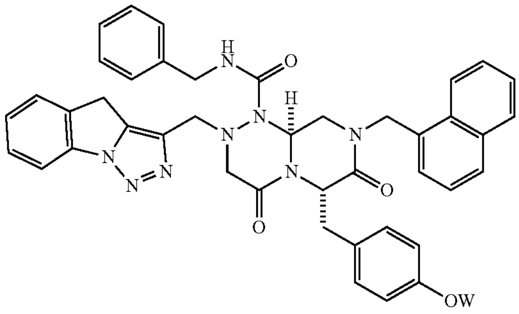
,
-continued
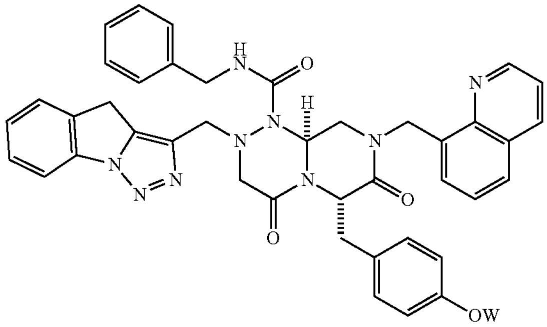
,
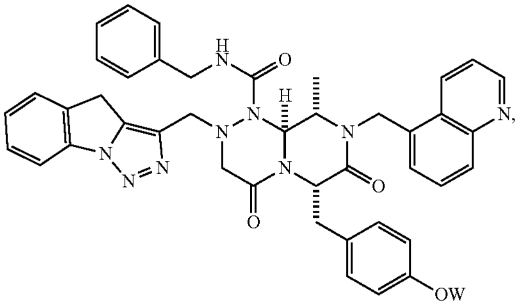
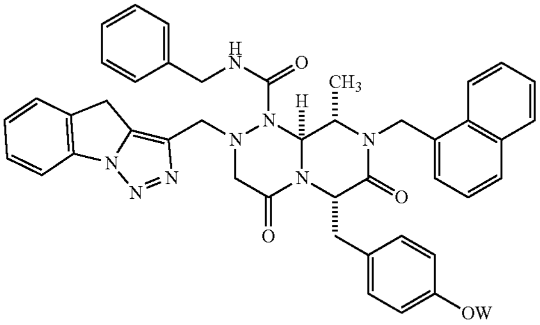
,
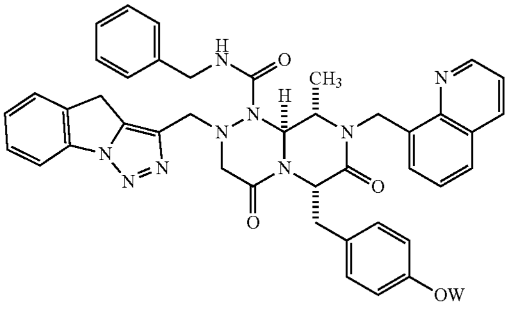
, or
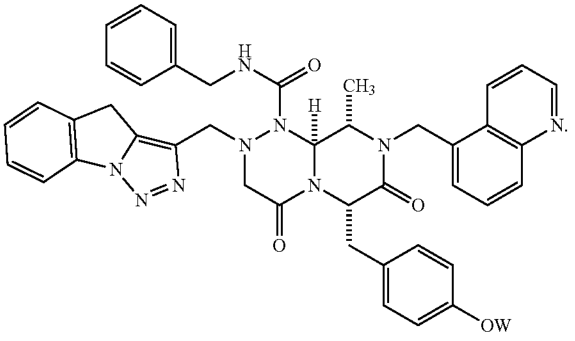
12. The compound of any one of clauses 1 to 11, wherein W is an ester of the alkyl acid or of the fatty acid, selected from:

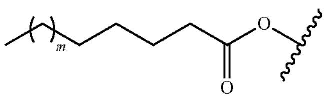

wherein m is 1 to 14,

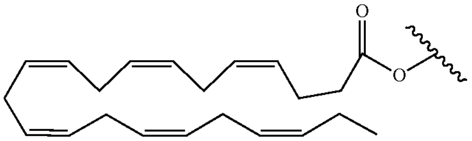

, or

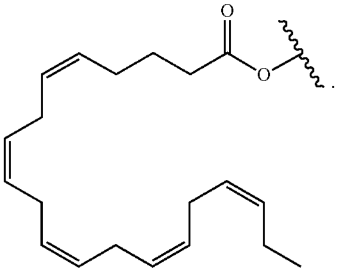

.

13. A pharmaceutical composition comprising the compound of any one of clauses 1 to 12, and a pharmaceutically acceptable carrier. In another aspect, provided is a pharmaceutical composition including a pharmaceutically acceptable excipient and a compound, as described herein.
14. A method of treating a disease or disorder associated with modulation of CREB binding protein (CBP)/catenin signaling pathway, said method comprises administering to a patient or a warm blooded mammal in need thereof a therapeutically effective amount of the compound of any one of clauses 1 to 11, wherein W is hydrogen, phosphate or phosphate salt, preferably hydrogen. In another aspect, provided is a method of treating a Wnt/catenin signaling pathway/CBP/catenin signaling pathway modulated disease or disorder in a subject in need of the treatment, the method including administering an effective amount of a compound described herein, to the subject.
15. The method of clause 14, wherein the disease or disorder associated with modulation of the CBP/catenin signaling pathway is cancer, fibrosis or diabetes.
16. The method of clause 15 for use in treating cancer, fibrosis or diabetes. For example, further provided is a method of treating fibrosis in a subject in need of the treatment, the method including administering an effective amount of a compound described herein, to the subject. Further provided is a method of treating diabetes in a subject in need of the treatment, the method including administering an effective amount of a compound described herein, to the subject. Further provided is a method of treating neurodevelopmental or neurodegenerative diseases in a subject in need of the treatment, the method including administering an effective amount of a compound described herein, to the subject. For example, further provided is a method of treating cancer in a subject in need of the treatment, the method including administering an effective amount of described herein, to the subject.
17. The method of clause 16, wherein the fibrosis is fibrosis of the lung, liver, kidney, heart or systemic fibrosis.
18. A cosmetic method for treating a skin condition, comprising transdermally or topically administering to a patient or a warm-blooded mammal, having a skin condition, a cosmeceutically effective amount of the compound of any one of clauses 1-11, wherein W is an ester of an alkyl acid or of a fatty acid, preferably wherein the ester of the alkyl acid or of the fatty acid is selected from:

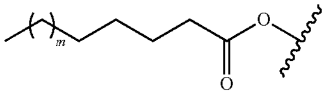

wherein m is 1 to 14,

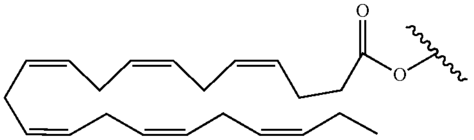

, or

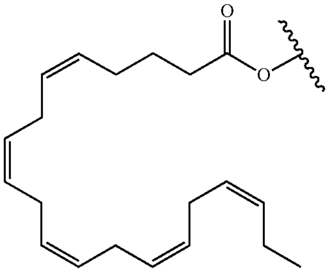

.

19. The method of clause 18, wherein the skin condition comprises one or more aging skin conditions selected from wrinkles, hyperpigmentation, redness, rosacea, dryness, cracking, loss of vibrance, loss of elasticity, thinning, loss of vibrance, scarring, acne, sun damage, hair loss, loss of hair coloration, reduced cuticle growth, and/or reduced nail growth.

Further provided is a method of treating neurodevelopmental or neurodegenerative diseases in a subject in need of the treatment, the method including administering an effective amount of a compound described herein, to the subject. Further provided is a cosmetic method for treating a skin condition, comprising transdermally or topically administering to a patient or a warm-blooded mammal, having a skin condition, a cosmeceutically effective amount of a compound described herein, preferably wherein the condition is one or more selected from wrinkles, hyperpigmentation, redness, rosacea, dryness, cracking, loss of vibrance, loss of elasticity, thinning, loss of vibrance, scarring, acne, sun damage, hair loss, loss of hair coloration, reduced cuticle growth, and/or reduced nail growth.

DETAILD DESCRIPTION OF THE DRAWINGS

FIG. 1 depicts the effects of the tested compounds on the Wnt-driven luciferase activity in stably transfected Hek293 cell line (STF1.1 assay). The STF1.1 assay is a general assay for Wnt inhibition. Compound ICG-001 was used as a positive control.

Figure 2:
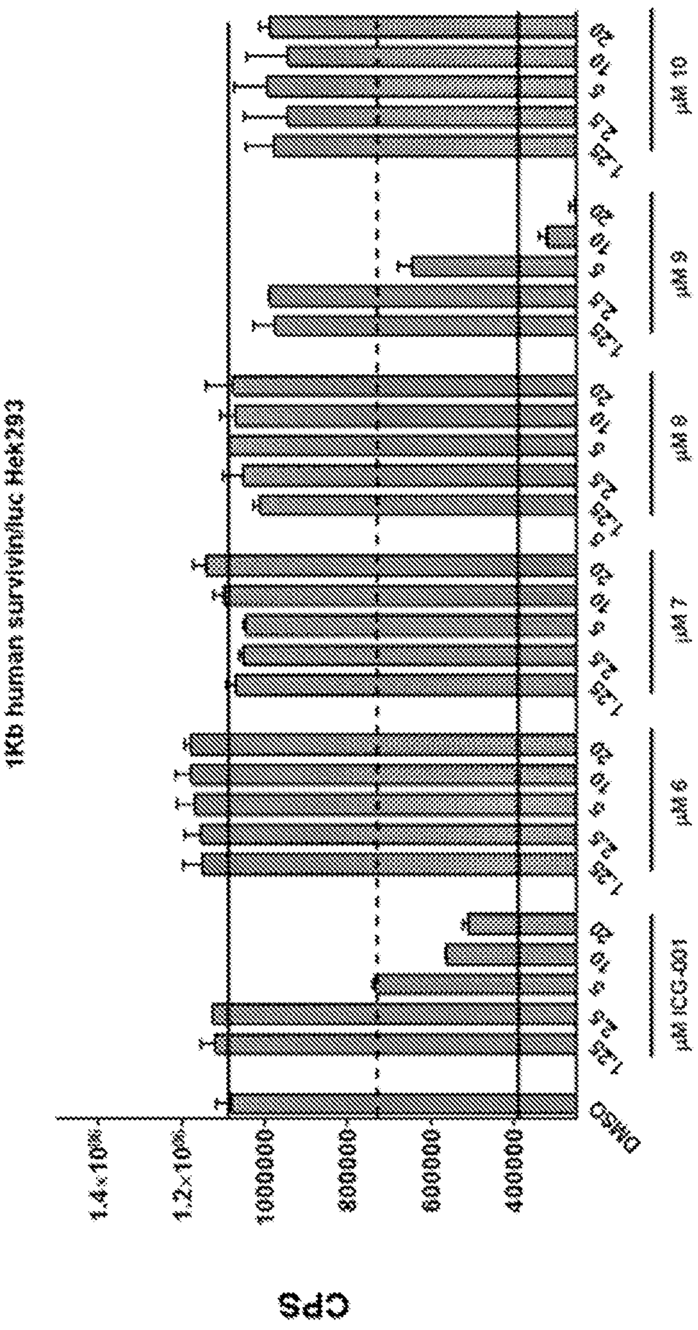

FIG. 2 depicts the effects of the tested compounds on the human Survinin 1 Kb-promoter-driven luciferase activity in stably transfected Hek293 cell line (1 Kb-survinin/luc Hek293 assay). The 1 Kb Hu-survivin\luc-Hek293 assay is utilized for identification of Kat3 coactivator specificity, in this instance specific Wnt/CBP/Catenin antagonists (Higuchi et al. *Current Mol. Pharmacol.* 2016, 9, 272-279). Compound ICG-001 was used as a positive control.

DETAILED DESCRIPTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—S—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —R', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol “~” denotes the point of attachment of a chemical moiety to the remainder of a molecule or chemical formula.

The term “oxo,” as used herein, means an oxygen that is double bonded to a carbon atom.

The term “alkylsulfonyl,” as used herein, means a moiety having the formula —$S(O_2)$—R', where R' is a substituted or unsubstituted alkyl group as defined above. R' may have a specified number of carbons (e.g., “$C_1$-$C_4$ alkylsulfonyl”).

The term “alkylarylene” as an arylene moiety covalently bonded to an alkylene moiety (also referred to herein as an alkylene linker). In embodiments, the alkylarylene group has the formula:

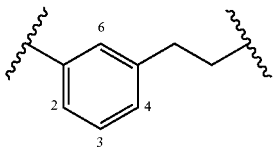

or

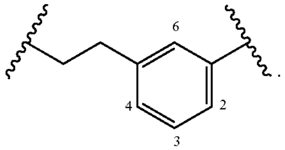

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$—$SO_3H$, —$OSO_3H$, —$SO_2NH_2$, —$NHNH_2$, —$ONH_2$, —$NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., “alkyl,” “heteroalkyl,” “cycloalkyl,” “heterocycloalkyl,” “aryl,” and “heteroaryl”) includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —R', -halogen, —SiR'R"R'", —OC(O)R', —C(O)R', —$CO_2$R', —CONR'R", —OC(O)NR'R", —NR"C(O)R', —NR'—C(O)NR"R'", —NR"$C(O)_2$R', —NR—C(NR'R"R'")=NR"", —NR—C(NR'R")=NR'", —S(O)R', —$S(O)_2$R', —$S(O)_2$NR'R", —$NRSO_2$R', —NR'NR"R'", —ONR'R", —NR'C(O)NR"NR'"R"", —CN, —$NO_2$, —NR'$SO_2$R", —NR'C(O)R", —NR'C(O)—OR", —NR'OR", in a number ranging from zero to (2 m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term “alkyl” is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"$C(O)_2$R', —NR—C(NR'R"R'")=NR"", —NR—C(NR'R")=NR'", —S(O)R', —$S(O)_2$R', —$S(O)_2$NR'R", —$NRSO_2$R', —NR'NR"R'", —ONR'R", —NR'C(O)NR"NR'"R"", —CN, —$NO_2$, —R', —$N_3$, —$CH(Ph)_2$, fluoro($C_1$-$C_4$)alkoxy, and fluoro($C_1$-$C_4$)alkyl, —NR'$SO_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—$(CRR')_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —$S(O)_2$—, —$(O)_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X'—$(C''R''R''')_d$, where s and d are independently integers of from 0 to 3, and X' is —O—, —NR'—, —S—, —S(O)—, —$S(O)_2$—, or —$S(O)_2$NR'—. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —$CCl_3$, —$CBr_3$, —$CF_3$, —$CI_3$, $CHCl_2$, —$CHBr_2$, $CHF_2$, —$CHI_2$, —$CH_2Cl$, —$CH_2Br$, $CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms. As used herein, the term "regioisomers" refers to compounds having the basic carbon skeleton unchanged but their functional groups or substituents change their position on a parent structure.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or $—CH_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "bind" and "bound" as used herein is used in accordance with its plain and ordinary meaning and refers to the association between atoms or molecules. The association can be direct or indirect. For example, bound atoms or molecules may be direct, e.g., by covalent bond or linker (e.g. a first linker or second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like).

The term "capable of binding" as used herein refers to a moiety (e.g. a compound as described herein) that is able to measurably bind to a target (e.g., a NF-κB, a Toll-like receptor protein). In embodiments, where a moiety is capable of binding a target, the moiety is capable of binding with a Kd of less than about 10 μM, 5 μM, 1 μM, 500 nM, 250 nM, 100 nM, 75 nM, 50 nM, 25 nM, 15 nM, 10 nM, 5 nM, 1 nM, or about 0.1 nM.

The terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

The terms "lung disease," "pulmonary disease," "pulmonary disorder," etc. are used interchangeably herein. The term is used to broadly refer to lung disorders characterized by difficulty breathing, coughing, airway discomfort and inflammation, increased mucus, and/or pulmonary fibrosis. Examples of lung diseases include lung cancer, cystic fibrosis, asthma, Chronic Obstructive Pulmonary Disease (COPD), bronchitis, emphysema, bronchiectasis, pulmonary edema, pulmonary fibrosis, sarcoidosis, pulmonary hypertension, pneumonia, tuberculosis, Interstitial Pulmonary Fibrosis (IPF), Interstitial Lung Disease (ILD), Acute Interstitial Pneumonia (A1P), Respiratory Bronchiolitis-associated Interstitial Lung Disease (RBILD), Desquamative Interstitial Pneumonia (DIP), Non-Specific Interstitial Pneumonia (NSIP), Idiopathic Interstitial Pneumonia (IIP), Bronchiolitis obliterans, with Organizing Pneumonia (BOOP), restrictive lung disease, or pleurisy.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cunateous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The terms "cutaneous metastasis" or "skin metastasis" refer to secondary malignant cell growths in the skin, wherein the malignant cells originate from a primary cancer site (e.g., breast). In cutaneous metastasis, cancerous cells from a primary cancer site may migrate to the skin where they divide and cause lesions. Cutaneous metastasis may result from the migration of cancer cells from breast cancer tumors to the skin.

The term "visceral metastasis" refer to secondary malignant cell growths in the internal organs (e.g., heart, lungs, liver, pancreas, intestines) or body cavities (e.g., pleura, peritoneum), wherein the malignant cells originate from a primary cancer site (e.g., head and neck, liver, breast). In visceral metastasis, cancerous cells from a primary cancer site may migrate to the internal organs where they divide and cause lesions. Visceral metastasis may result from the migration of cancer cells from liver cancer tumors or head and neck tumors to internal organs.

As used herein, the term "diabetes" refers to a group of metabolic discorders characterized by high blood sugar levels over a prolonged period of time. In certain instances, diabetes is represented by type 1 diabetes, type 2 diabetes, gestational diabetes, monogenic diabetes, and cystic fibrosis-related diabetes.

As used herein, the term "type 1 diabetes" refers to the condition when the body fails to produce insulin, and people with type I diabetes are insulin-dependent.

As used herein, the term "type 2 diabetes" refers to the condition when the way the body uses insulin is affected. While the body still makes insulin, the cells in the body do not respond to it as effectively. This type of diabetes is linked to obesity.

As used herein, the term "cystic fibrosis-related diabetes, CFRD" refers to diabetes specifically caused by genetic condition, cystic fibrosis (CF). In people with CF, the pancreas is scarred due to excessive amount of mucus, the characteristic feature of the disease. The scarring prevents the pancreas from producing normal amount of insulin.

As used herein, the term "fibrosis disorder" refers to the formation of excess fibrous connective tissue in an organ or tissue in a reparative or reactive process. Physiologically, fibrosis acts to deposit connective tissue, which can interfere with or totally inhibit the normal architecture and function of the underlying organ or tissue. In certain instances, fibrosis disorder is pulmonary fibrosis, hepatic fibrosis, renal fibrosis, cardiac fibrosis, or systemic fibrosis.

As used herein, the term "pulmonary fibrosis" refers to a condition that causes excessive lung scarring and stiffness.

As used herein, the term "hepatic fibrosis" refers to a condition in which an overly active wound healing causes excessive connective tissue build up in the liver and normal structural elements of tissues are replaced with large amounts of scar tissue.

As used herein, the term "renal fibrosis" or "interstitial fibrosis" refers to a condition characterized by the destruction of renal tubules and interstitial capillaries and the deposition of connective tissue on the kidney parenchyma leading to kidney failure.

As used herein, the term "cardiac fibrosis" refers to excess deposition of extracellular matrix in the cardiac muscle that leads to heart failure.

As used herein, the term "systemic fibrosis" refers to a disorder involving fibrosis of skin, joints, eyes, and internal organs, and is believed to be caused by exposure to gadolinium.

As used herein, the term neurodevelopmental diseases or disorders are a group of disorders which affect the development of the nervous system, leading to abnormal brain function which may affect emotion, learning ability, self-control, and memory. The effects of neurodevelopmental disorders tend to last for a person's entire lifetime. The neurodevelopmental disorders include Intellectual disability (ID) or intellectual and developmental disability (IDD), previously called mental retardation, specific learning disorders, like Dyslexia or Dyscalculia; Autism spectrum disorders, such as Asperger's syndrome or Autistic Disorder; Motor disorders including developmental coordination disorder and stereotypic movement disorder; Tic disorders including Tourette's syndrome; Traumatic brain injury (including congenital injuries such as those that cause cerebral palsy); Communication, speech and language disorders; Genetic disorders, such as fragile-X-syndrome, Down syndrome, attention deficit hyperactivity disorder, schizophrenia, schizotypal disorder, hypogonadotropic hypogonadal syndromes and disorders due to neurotoxicants like fetal alcohol spectrum disorder, Minamata disease caused by mercury, behavioral disorders including conduct disorder, etc. caused by other heavy metals such as lead, chromium, platinum etc., hydrocarbons like dioxin, PBDEs and PCBs, medications and illegal drugs, like cocaine and others.

As used herein, term neurodegeneration is the progressive loss of structure or function of neurons, including death of neurons. Many neurodegenerative diseases—including amyotrophic lateral sclerosis (ALS), Parkinson's disease, Alzheimer's disease, fatal familial insomnia, multiple sclerosis (MS) and Huntington's disease—occur as a result of neurodegenerative processes. Such diseases are incurable, resulting in progressive degeneration and/or death of neuron cells. As research progresses, many similarities appear that relate these diseases to one another on a sub-cellular level. Discovering these similarities offers hope for therapeutic advances that could ameliorate many diseases simultaneously. There are many parallels between different neurodegenerative disorders including atypical protein assemblies as well as induced cell death. Neurodegeneration can be found in many different levels of neuronal circuitry ranging from molecular to systemic.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom (s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and Remington: *The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

A "cosmeceutically effective amount" is amount which, when administered (e.g., transdermal, topical) is sufficient to affect cosmetic treatment of a cosmetic condition (e.g., wrinkles, hyperpigmentation, redness, rosacea, dryness, cracking, loss of vibrance, loss of elasticity, thinning, loss of vibrance, scarring, acne, sun damage, hair loss, loss of hair coloration, reduced cuticle growth, reduced nail growth).

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

As used herein, the term "co-administer" it is meant that a composition described herein is administered at the same time, just prior to, or just after the administration of one or more additional therapies. The compounds provided herein can be administered alone or can be co-administered to the patient. Co-administration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

As used herein, the term "control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

As used herein, the terms "selective" or "selectivity" or the like of a compound refers to the compound's ability to discriminate between molecular targets.

As used herein, the terms "specific", "specifically", "specificity", or the like of a compound refers to the compound's ability to cause a particular action, such as inhibition, to a particular molecular target with minimal or no action to other proteins in the cell.

As used herein, the term "CREB-binding protein", "CREBBP" or "CBP" is a protein that in humans is encoded by the CREBBP gene. The CREB protein carries out its function by activating transcription, where interaction with transcription factors is managed by one or more CREB domains: the nuclear receptor interaction domain (RID), the KIX domain (CREB and MYB interaction domain), the cysteine/histidine regions (TAZ1/CH1 and TAZ2/CH3) and the interferon response binding domain (IBiD). The CREB protein domains, KIX, TAZ1 and TAZ2, each bind tightly to a sequence spanning both transactivation domains 9aaTADs of transcription factor p53.

As used herein, the term "catenin" refers to a family of proteins found in complexes with cadherin cell adhesion molecules of animal cells. Catenins can bind to each other and actin and thought to be linking cadherins to the cytoskeleton.

As used herein, the term "CBP/catenin signaling pathway" or "Wnt/β catenin signaling pathway" refers to a group of signal transduction pathways which begin with proteins that pass signals into a cell through cell surface receptors. This is an evolutionarily conserved pathway and plays indispensable role in both embryonic development and adult homeostasis, such as regulation of cell growth, motility, differentiation during embryonic development, and activation of diverse signaling cascades inside the target cells.

II. Compounds

In an aspect, provided herein is a compound having the formula (unless stated otherwise W in the following compounds is H, phosphate, phosphate salt or an ester of an alkyl acid or of a fatty acid, preferably H):

(Ia)

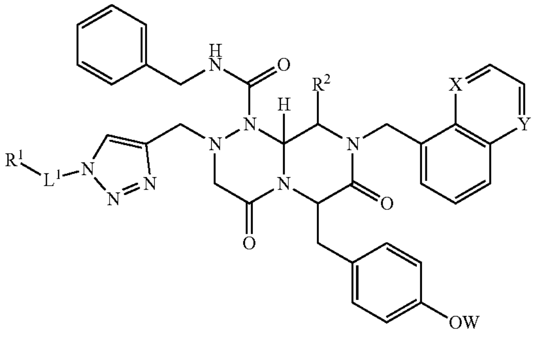

or (Ib)

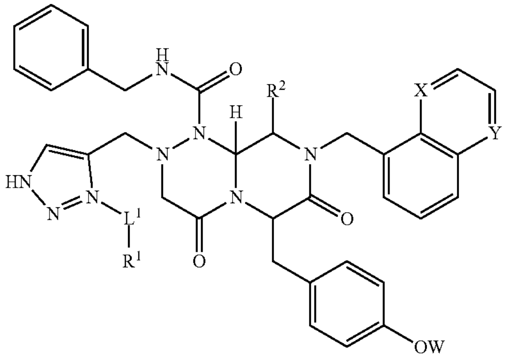

or

-continued (Ic)

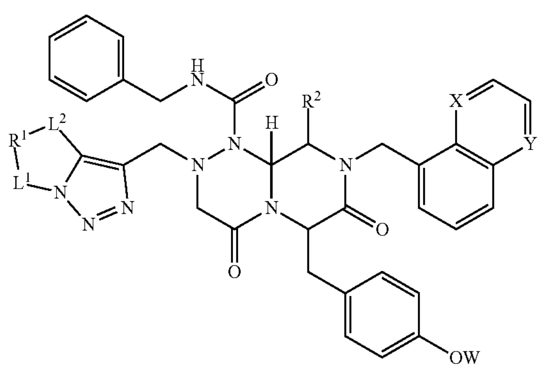

X is N or —CH. Y is N or —CH. $L^1$ or $L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. $R^1$ is independently hydrogen, halogen, $—CX^1_3$, $—CHX^1_2$, $—CH_2X^1$, $—OCX^1_3$, $—OCHX^1_2$, $—OCH_2X^1$, —CN, $—S(O)_2R^{1A}$, $—SR^{1A}$, $—S(O)R^{1A}$, $—SO_2NR^{1A}R^{1B}$, $—NHC(O)NR^{1A}R^{1B}$, $—N(O)_2$, $—NR^{1A}R^{1B}$, $—NHNR^{1A}R^{1B}$, $—C(O)R^{1A}$, $—C(O)—OR^{1A}$, $—C(O)NR^{1A}R^{1B}$, $—C(O)NHNR^{1A}R^{1B}$, $—OR^{1A}$, $—NR^{1A}SO_2R^{1B}$, $—NR^{1A}C(O)R^{1B}$, $—NR^{1A}C(O)OR^{1B}$, $—NR^{1A}OR^{1B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen or substituted or unsubstituted $C_1$-$C_4$ alkyl. $R^{1A}$ and $R^{1B}$ are independently hydrogen, $—CX^1_3$, $—CHX^1_2$, $—CH_2X^1$, —C(O)OH, $—C(O)NH_2$, —OH, $—NH_2$, —COOH, $—CONH_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC=(O)H, —NHC(O)OH, —NHOH, $—OCX^1_3$, $—OCHX^1_2$, $—OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{1A}$ and $R^{1B}$ substituents bonded to the same nitrogen atom may optionally be joined to form a substituted or unsubstituted heterocycloalkyl or substituted or unsubstituted heteroaryl. $X^1$ is halogen. W is hydrogen, phosphate or phosphate salt, or an ester of an alkyl acid or of a fatty acid, preferably hydrogen.

In embodiments, the compound has the formula (Ia'), (Ib') or (Ic):

(Ia')

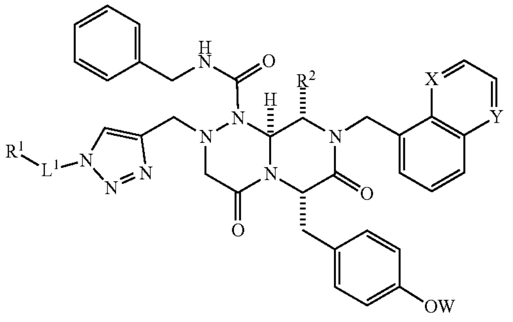

or

-continued (Ib')

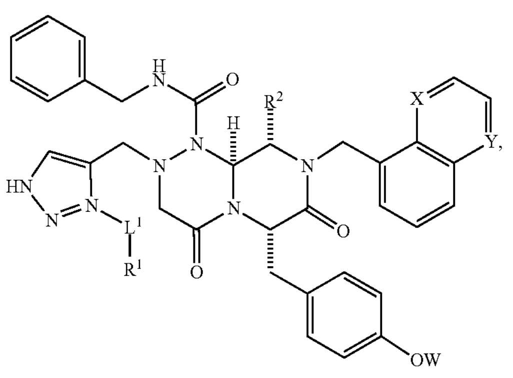

or (Ic')

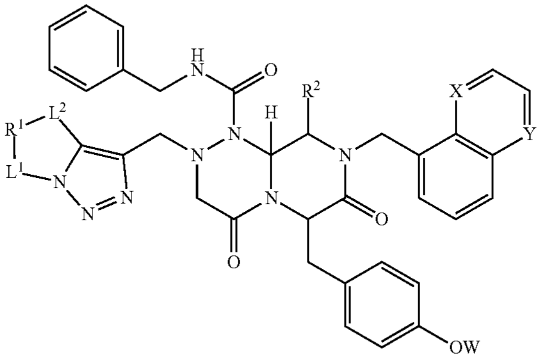

wherein X, Y, $L^1$, $L^2$, $R^1$, $R^2$ and W are as defined above, including embodiments thereof.

In embodiments, $L^1$ or $L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. In embodiments, $L^1$ or $L^2$ is a bond. In embodiments, $L^1$ or $L^2$ is a substituted or unsubstituted alkylene. In embodiments, $L^1$ or $L^2$ is $(CH_2)_n$, and n is an integer from 0 to 4. In embodiments, $L^1$ or $L^2$ is methylene or ethylene.

In embodiments, $R^1$ is independently hydrogen, halogen, $—CX^1_3$, $—CHX^1_2$, $—CH_2X^1$, $—OCX^1_3$, $—OCHX^1_2$, $—OCH_2X^1$, —CN, $—S(O)_2R^{1A}$, $—SR^{1A}$, $—S(O)R^{1A}$, $—SO_2NR^{1A}R^{1B}$, $—NHC(O)NR^{1A}R^{1B}$, $—N(O)_2$, $—NR^{1A}R^{1B}$, $—NHNR^{1A}R^{1B}$, $—C(O)R^{1A}$, $—C(O)—OR^{1A}$, $—C(O)NR^{1A}R^{1B}$, $—C(O)NHNR^{1A}R^{1B}$, $—OR^{1A}$, $—NR^{1A}SO_2R^{1B}$, $—NR^{1A}C(O)R^{1B}$, $—NR^{1A}C(O)OR^{1B}$, $—NR^{1A}OR^{1B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^1$ is hydrogen, halogen (e.g., —F, —Cl, Br, —I), $—CX^1_3$, $—CHX^1_2$, $—CH_2X^1$, $—OCX^1_3$, $—OCHX^1_2$, $—OCH_2X^1$, —CN, $—S(O)_2R^{1A}$, $—SR^{1A}$, $—S(O)R^{1A}$, $—SO_2NR^{1A}R^{1B}$, $—NHC(O)NR^{1A}R^{1B}$, $—N(O)_2$, $—NR^{1A}R^{1B}$, $—NHNR^{1A}R^{1B}$, $—C(O)R^{1A}$, $—C(O)—OR^{1A}$, $—C(O)NR^{1A}R^{1B}$, $—C(O)—NHNR^{1A}R^{1B}$, $—OR^{1A}$, $—NR^{1A}SO_2R^{1B}$, $—NR^{1A}C(O)R^{1B}$, $—NR^{1A}C(O)OR^{1B}$, $—NR^{1A}R^{1B}$, $—N_3$, (e.g., $—CF_3$, $—CHF_2$, $—CH_2F$, $—CCl_3$, $—CHCl_2$, $—CH_2Cl$, $—CBr_3$, $—CHBr_2$, $—CH_2Br$, $—CI_3$, $—CHI_2$, $—CH_2I$, $—OCF_3$, $—OCCl_3$, $—OCBr_3$, $—OCI_3$, $—OCHF_2$, $—OCHCl_2$, $—OCHBr_2$, $—OCHI_2$, $—OCH_2F$, $—OCH_2Cl$, $—OCH_2Br$, $—OCH_2I$, $—N_3$, —CN, —SH, $—SCH_3$, $—SO_2H$, $—SO_2CH_3$, $—SO_2NH_2$, $—SO_2NHCH_3$, $—NHC(O)NH_2$, $—NHC(O)NHCH_3$, $—NO_2$, $—NH_2$, $—NHCH_3$, —C(O)H, $—C(O)CH_3$, —C(O)OH, $—C(O)OCH_3$, $—C(O)NH_2$, $—C(O)NHCH_3$, —OH, $—OCH_3$, $—NHSO_2H$, $—NHSO_2CH_3$, —NHC(O)H, $—NCH_3C(O)H$, —NHC(O)OH, $—NCH_3C(O)OH$, —NHOH, $—NCH_3OH$, or $—NCH_3OCH_3$), substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). $X^1$ is independently —F, —Cl, —Br, or —I.

In embodiments, $R^1$ is hydrogen, —F, —Cl, Br, —I, $—CF_3$, $—CHF_2$, $—CH_2F$, $—CCl_3$, $—CHCl_2$, $—CH_2Cl$, $—CBr_3$, $—CHBr_2$, $—CH_2Br$, $—CI_3$, $—CHI_2$, $—CH_2I$, $—OCF_3$, $—OCCl_3$, $—OCBr_3$, $—OCI_3$, $—OCHF_2$, $—OCHCl_2$, $—OCHBr_2$, $—OCHI_2$, $—OCH_2F$, $—OCH_2Cl$, $—OCH_2Br$, $—OCH_2I$, $—N_3$, —CN, —SH, $—SCH_3$, $—SO_2H$, $—SO_2CH_3$, $—SO_2NH_2$, $—SO_2NHCH_3$, $—NHC(O)NH_2$, $—NHC(O)NHCH_3$, $—NO_2$, $—NH_2$, $—NHCH_3$, —C(O)H, $—C(O)CH_3$, —C(O)OH, $—C(O)OCH_3$, $—C(O)NH_2$, $—C(O)NHCH_3$, —OH, $—OCH_3$, $—NHSO_2H$, $—NHSO_2CH_3$, —NHC(O)H, $—NCH_3C(O)H$, —NHC(O)OH, $—NCH_3C(O)OH$, —NHOH, $—NCH_3OH$, $—NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^1$ is hydrogen, —F, —Cl, Br, —I, $—CF_3$, $—CHF_2$, $—CH_2F$, $—CCl_3$, $—CHCl_2$, $—CH_2Cl$, $—CBr_3$, $—CHBr_2$, $—CH_2Br$, $—CI_3$, $—CHI_2$, $—CH_2I$, $—OCF_3$, $—OCCl_3$, $—OCBr_3$, $—OCI_3$, $—OCHF_2$, $—OCHCl_2$, $—OCHBr_2$, $—OCHI_2$, $—OCH_2F$, $—OCH_2Cl$, $—OCH_2Br$, $—OCH_2I$, $—N_3$, —CN, —SH, $—SCH_3$, $—SO_2H$, $—SO_2CH_3$, $—SO_2NH_2$, $—SO_2NHCH_3$, —NHC (O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3OH$, —$NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^1$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^3$-substituted or unsubstituted alkyl (e.g., $C_1$-$C_8$ alkyl, $C_1$-$C_6$ alkyl, or $C_1$-$C_4$ alkyl), $R^3$-substituted or unsubstituted heteroalkyl (e.g., 2 to 8 membered heteroalkyl, 2 to 6 membered heteroalkyl, or 2 to 4 membered heteroalkyl), $R^3$-substituted or unsubstituted cycloalkyl (e.g., $C_3$-$C_8$ cycloalkyl, $C_3$-$C_6$ cycloalkyl, or $C_5$-$C_6$ cycloalkyl), $R^3$-substituted or unsubstituted heterocycloalkyl (e.g., 3 to 8 membered heterocycloalkyl, 3 to 6 membered heterocycloalkyl, or 5 to 6 membered heterocycloalkyl), $R^3$-substituted or unsubstituted aryl (e.g., $C_6$-$C_{10}$ aryl, $C_{10}$ aryl, or phenyl), or $R^3$-substituted or unsubstituted heteroaryl (e.g., 5 to 10 membered heteroaryl, 5 to 9 membered heteroaryl, or 5 to 6 membered heteroaryl).

In embodiments, $R^1$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_3I$, —$OCH_2F$, —$OCH_2Cl$, —$OCH_2Br$, or —$OCH_2I$.

In embodiments, $R^1$ is $R^3$-substituted or unsubstituted alkyl (e.g., $C_1$-$C_8$ alkyl, $C_1$-$C_6$ alkyl, or $C_1$-$C_4$ alkyl). In embodiments, $R^1$ is $R^3$-substituted alkyl (e.g., $C_1$-$C_8$ alkyl, $C_1$-$C_6$ alkyl, or $C_1$-$C_4$ alkyl). In embodiments, $R^1$ is an unsubstituted alkyl (e.g., $C_1$-$C_8$ alkyl, $C_1$-$C_6$ alkyl, or $C_1$-$C_4$ alkyl). In embodiments, $R^1$ is $R^3$-substituted or unsubstituted heteroalkyl (e.g., 2 to 8 membered heteroalkyl, 2 to 6 membered heteroalkyl, or 2 to 4 membered heteroalkyl). In embodiments, $R^1$ is $R^3$-substituted heteroalkyl (e.g., 2 to 8 membered heteroalkyl, 2 to 6 membered heteroalkyl, or 2 to 4 membered heteroalkyl). In embodiments, $R^1$ is an unsubstituted heteroalkyl (e.g., 2 to 8 membered heteroalkyl, 2 to 6 membered heteroalkyl, or 2 to 4 membered heteroalkyl). In embodiments, $R^1$ is $R^3$-substituted or unsubstituted cycloalkyl (e.g., $C_3$-$C_8$ cycloalkyl, $C_3$-$C_6$ cycloalkyl, or $C_5$-$C_6$ cycloalkyl 1). In embodiments, $R^1$ is $R^3$-substituted cycloalkyl (e.g., $C_3$-$C_8$ cycloalkyl, $C_3$-$C_6$ cycloalkyl, or $C_5$-$C_6$ cycloalkyl). In embodiments, $R^1$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^1$ is $R^3$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^1$ is $R^3$-substituted heterocycloalkyl (e.g., 3 to 8 membered heterocycloalkyl, 3 to 6 membered heterocycloalkyl, or 5 to 6 membered heterocycloalkyl). In embodiments, $R^1$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^1$ is $R^3$-substituted or unsubstituted aryl (e.g., $C_6$-$C_{10}$ aryl, $C_{10}$ aryl, or phenyl). In embodiments, $R^1$ is $R^3$-substituted aryl (e.g., $C_6$-$C_{10}$ aryl, $C_{10}$ aryl, or phenyl). In embodiments, $R^1$ is an unsubstituted aryl (e.g., $C_6$-$C_{10}$ aryl, $C_{10}$ aryl, or phenyl). In embodiments, $R^1$ is $R^3$-substituted or unsubstituted heteroaryl (e.g., 5 to 10 membered heteroaryl, 5 to 9 membered heteroaryl, or 5 to 6 membered heteroaryl). In embodiments, $R^1$ is $R^3$-substituted heteroaryl (e.g., 5 to 10 membered heteroaryl, 5 to 9 membered heteroaryl, or 5 to 6 membered heteroaryl). In embodiments, $R^1$ is an unsubstituted heteroaryl (e.g., 5 to 10 membered heteroaryl, 5 to 9 membered heteroaryl, or 5 to 6 membered heteroaryl).

$R^3$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^4$-substituted or unsubstituted alkyl (e.g., $C_1$-$C_8$ alkyl, $C_1$-$C_6$ alkyl, or $C_1$-$C_4$ alkyl), $R^4$-substituted or unsubstituted heteroalkyl (e.g., 2 to 8 membered heteroalkyl, 2 to 6 membered heteroalkyl, or 2 to 4 membered heteroalkyl), $R^4$-substituted or unsubstituted cycloalkyl (e.g., $C_3$-$C_8$ cycloalkyl, $C_3$-$C_6$ cycloalkyl, or $C_5$-$C_6$ cycloalkyl), $R^4$-substituted or unsubstituted heterocycloalkyl (e.g., 3 to 8 membered heterocycloalkyl, 3 to 6 membered heterocycloalkyl, or 5 to 6 membered heterocycloalkyl), $R^4$-substituted or unsubstituted aryl (e.g., $C_6$-$C_{10}$ aryl, $C_{10}$ aryl, or phenyl), or $R^4$-substituted or unsubstituted heteroaryl (e.g., 5 to 10 membered heteroaryl, 5 to 9 membered heteroaryl, or 5 to 6 membered heteroaryl).

In embodiments, $R^3$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^3$ is $R^4$-substituted or unsubstituted alkyl (e.g., $C_1$-$C_8$ alkyl, $C_1$-$C_6$ alkyl, or $C_1$-$C_4$ alkyl). In embodiments, $R^3$ is $R^4$-substituted (e.g., $C_1$-$C_8$ alkyl, $C_1$-$C_6$ alkyl, or $C_1$-$C_4$ alkyl). In embodiments, $R^3$ is unsubstituted alkyl (e.g., $C_1$-$C_8$ alkyl, $C_1$-$C_6$ alkyl, or $C_1$-$C_4$ alkyl). In embodiments, $R^3$ is $R^4$-substituted or unsubstituted heteroalkyl (e.g., 2 to 8 membered heteroalkyl, 2 to 6 membered heteroalkyl, or 2 to 4 membered heteroalkyl). In embodiments, $R^3$ is $R^4$-substituted heteroalkyl (e.g., 2 to 8 membered heteroalkyl, 2 to 6 membered heteroalkyl, or 2 to 4 membered heteroalkyl). In embodiments, $R^3$ is unsubstituted heteroalkyl (e.g., 2 to 8 membered heteroalkyl, 2 to 6 membered heteroalkyl, or 2 to 4 membered heteroalkyl). In embodiments, $R^3$ is $R^4$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^3$ is $R^4$-substituted cycloalkyl (e.g., $C_3$-$C_8$ cycloalkyl, $C_3$-$C_6$ cycloalkyl, or $C_5$-$C_6$ cycloalkyl). In embodiments, $R^3$ is unsubstituted cycloalkyl (e.g., $C_3$-$C_8$ cycloalkyl, $C_3$-$C_6$ cycloalkyl, or $C_5$-$C_6$ cycloalkyl). In embodiments, $R^3$ is $R^4$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^3$ is $R^4$-substituted heterocycloalkyl (e.g., 3 to 8 membered heterocycloalkyl, 3 to 6 membered heterocycloalkyl, or 5 to 6 membered heterocycloalkyl). In embodiments, $R^3$ is unsubstituted heterocycloalkyl (e.g., 3 to 8 membered heterocycloalkyl, 3 to 6 membered heterocycloalkyl, or 5 to 6 membered heterocycloalkyl). In embodiments, $R^3$ is $R^4$-substituted or unsubstituted aryl (e.g., $C_6$-$C_{10}$ aryl, $C_{10}$ aryl, or phenyl). In embodiments, $R^3$ is $R^4$-substituted aryl (e.g., $C_6$-$C_{10}$ aryl, $C_{10}$ aryl, or phenyl). In embodiments, $R^3$ is unsubstituted aryl (e.g., $C_6$-$C_{10}$ aryl, $C_{10}$ aryl, or phenyl). In embodiments, $R^3$ is $R^4$-substituted or unsubstituted heteroaryl (e.g., 5 to 10 membered heteroaryl, 5 to 9 membered heteroaryl, or 5 to 6 membered heteroaryl). In embodiments, $R^3$ is $R^4$-substituted heteroaryl (e.g., 5 to 10 membered heteroaryl, 5 to 9 membered heteroaryl, or 5 to 6 membered heteroaryl). In embodiments, $R^3$ is unsubstituted heteroaryl (e.g., 5 to 10 membered heteroaryl, 5 to 9 membered heteroaryl, or 5 to 6 membered heteroaryl).

$R^4$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^5$-substituted or unsubstituted alkyl (e.g., $C_1$-$C_8$ alkyl, $C_1$-$C_6$ alkyl, or $C_1$-$C_4$ alkyl), $R^5$-substituted or unsubstituted heteroalkyl (e.g., 2 to 8 membered heteroalkyl, 2 to 6 membered heteroalkyl, or 2 to 4 membered heteroalkyl), $R^5$-substituted or unsubstituted cycloalkyl (e.g., $C_3$-$C_8$ cycloalkyl, $C_3$-$C_6$ cycloalkyl, or $C_5$-$C_6$ cycloalkyl), $R^5$-substituted or unsubstituted heterocycloalkyl (e.g., 3 to 8 membered heterocycloalkyl, 3 to 6 membered heterocycloalkyl, or 5 to 6 membered heterocycloalkyl), $R^5$-substituted or unsubstituted aryl (e.g., $C_6$-$C_{10}$ aryl, $C_{10}$ aryl, or phenyl), or $R^5$-substituted or unsubstituted heteroaryl (e.g., 5 to 10 membered heteroaryl, 5 to 9 membered heteroaryl, or 5 to 6 membered heteroaryl).

In embodiments, $R^4$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^4$ is $R^5$-substituted or unsubstituted alkyl (e.g., $C_1$-$C_8$ alkyl, $C_1$-$C_6$ alkyl, or $C_1$-$C_4$ alkyl). In embodiments, $R^4$ is $R^5$-substituted (e.g., $C_1$-$C_8$ alkyl, $C_1$-$C_6$ alkyl, or $C_1$-$C_4$ alkyl). In embodiments, $R^4$ is unsubstituted alkyl (e.g., $C_1$-$C_8$ alkyl, $C_1$-$C_6$ alkyl, or $C_1$-$C_4$ alkyl). In embodiments, $R^4$ is $R^5$-substituted or unsubstituted heteroalkyl (e.g., 2 to 8 membered heteroalkyl, 2 to 6 membered heteroalkyl, or 2 to 4 membered heteroalkyl). In embodiments, $R^4$ is $R^5$-substituted heteroalkyl (e.g., 2 to 8 membered heteroalkyl, 2 to 6 membered heteroalkyl, or 2 to 4 membered heteroalkyl). In embodiments, $R^4$ is unsubstituted heteroalkyl (e.g., 2 to 8 membered heteroalkyl, 2 to 6 membered heteroalkyl, or 2 to 4 membered heteroalkyl). In embodiments, $R^4$ is $R^5$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^4$ is $R^5$-substituted cycloalkyl (e.g., $C_3$-$C_8$ cycloalkyl, $C_3$-$C_6$ cycloalkyl, or $C_5$-$C_6$ cycloalkyl). In embodiments, $R^4$ is unsubstituted cycloalkyl (e.g., $C_3$-$C_8$ cycloalkyl, $C_3$-$C_6$ cycloalkyl, or $C_5$-$C_6$ cycloalkyl). In embodiments, $R^4$ is $R^5$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^4$ is $R^5$-substituted heterocycloalkyl (e.g., 3 to 8 membered heterocycloalkyl, 3 to 6 membered heterocycloalkyl, or 5 to 6 membered heterocycloalkyl). In embodiments, $R^4$ is unsubstituted heterocycloalkyl (e.g., 3 to 8 membered heterocycloalkyl, 3 to 6 membered heterocycloalkyl, or 5 to 6 membered heterocycloalkyl). In embodiments, $R^4$ is $R^5$-substituted or unsubstituted aryl (e.g., $C_6$-$C_{10}$ aryl, $C_{10}$ aryl, or phenyl). In embodiments, $R^4$ is $R^5$-substituted aryl (e.g., $C_6$-$C_{10}$ aryl, $C_{10}$ aryl, or phenyl). In embodiments, $R^4$ is unsubstituted aryl (e.g., $C_6$-$C_{10}$ aryl, $C_{10}$ aryl, or phenyl). In embodiments, $R^4$ is $R^5$-substituted or unsubstituted heteroaryl (e.g., 5 to 10 membered heteroaryl, 5 to 9 membered heteroaryl, or 5 to 6 membered heteroaryl). In embodiments, $R^4$ is $R^5$-substituted heteroaryl (e.g., 5 to 10 membered heteroaryl, 5 to 9 membered heteroaryl, or 5 to 6 membered heteroaryl). In embodiments, $R^4$ is unsubstituted heteroaryl (e.g., 5 to 10 membered heteroaryl, 5 to 9 membered heteroaryl, or 5 to 6 membered heteroaryl).

$R^5$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^5$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^5$ is independently unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{1A}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3OH$, —$NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{1A}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3OH$, —$NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{1A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{3A}$-substituted or unsubstituted alkyl (e.g., $C_1$-$C_8$ alkyl, $C_1$-$C_6$ alkyl, or $C_1$-$C_4$ alkyl), $R^{3A}$-substituted or unsubstituted heteroalkyl (e.g., 2 to 8 membered heteroalkyl, 2 to 6 membered heteroalkyl, or 2 to 4 membered heteroalkyl), $R^{3A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{3A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{3A}$-substituted or unsubstituted aryl (e.g., $C_6$-$C_{10}$ aryl, $C_{10}$ aryl, or phenyl), or $R^{3A}$-substituted or unsubstituted heteroaryl (e.g., 5 to 10 membered heteroaryl, 5 to 9 membered heteroaryl, or 5 to 6 membered heteroaryl).

In embodiments, $R^{1A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{1A}$ is $R^{3A}$-substituted or unsubstituted alkyl (e.g., $C_1$-$C_8$ alkyl, $C_1$-$C_6$ alkyl, or $C_1$-$C_4$ alkyl). In embodiments, $R^{1A}$ is $R^{3A}$-substituted alkyl (e.g., $C_1$-$C_8$ alkyl, $C_1$-$C_6$ alkyl, or $C_1$-$C_4$ alkyl). In embodiments, $R^{1A}$ is an unsubstituted alkyl (e.g., $C_1$-$C_8$ alkyl, $C_1$-$C_6$ alkyl, or $C_1$-$C_4$ alkyl). In embodiments, $R^{1A}$ is $R^{3A}$-substituted or unsubstituted heteroalkyl (e.g., 2 to 8 membered heteroalkyl, 2 to 6 membered heteroalkyl, or 2 to 4 membered heteroalkyl). In embodiments, $R^{1A}$ is $R^{3A}$-substituted heteroalkyl (e.g., 2 to 8 membered heteroalkyl, 2 to 6 membered heteroalkyl, or 2 to 4 membered heteroalkyl). In embodiments, $R^{1A}$ is an unsubstituted heteroalkyl (e.g., 2 to 8 membered heteroalkyl, 2 to 6 membered heteroalkyl, or 2 to 4 membered heteroalkyl). In embodiments, $R^{1A}$ is $R^{3A}$-substituted or unsubstituted cycloalkyl (e.g., $C_3$-$C_8$ cycloalkyl, $C_3$-$C_6$ cycloalkyl, or $C_5$-$C_6$ cycloalkyl 1). In embodiments, $R^{1A}$ is $R^{3A}$-substituted cycloalkyl (e.g., $C_3$-$C_8$ cycloalkyl, $C_3$-$C_6$ cycloalkyl, or $C_5$-$C_6$ cycloalkyl). In embodiments, $R^{1A}$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1A}$ is $R^{3A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1A}$ is $R^{3A}$-substituted heterocycloalkyl (e.g., 3 to 8 membered heterocycloalkyl, 3 to 6 membered heterocycloalkyl, or 5 to 6 membered heterocycloalkyl). In embodiments, $R^{1A}$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^{1A}$ is $R^{3A}$-substituted or unsubstituted aryl (e.g., $C_6$-$C_{10}$ aryl, $C_{10}$ aryl, or phenyl). In embodiments, $R^{1A}$ is $R^{3A}$-substituted aryl (e.g., $C_6$-$C_{10}$ aryl, $C_{10}$ aryl, or phenyl). In embodiments, $R^{1A}$ is an unsubstituted aryl (e.g., $C_6$-$C_{10}$ aryl, $C_{10}$ aryl, or phenyl). In embodiments, $R^{1A}$ is $R^{3A}$-substituted or unsubstituted heteroaryl (e.g., 5 to 10 membered heteroaryl, 5 to 9 membered heteroaryl, or 5 to 6 membered heteroaryl). In embodiments, $R^{1A}$ is $R^{3A}$-substituted heteroaryl (e.g., 5 to 10 membered heteroaryl, 5 to 9 membered heteroaryl, or 5 to 6 membered heteroaryl). In embodiments, $R^{1A}$ is an unsubstituted heteroaryl (e.g., 5 to 10 membered heteroaryl, 5 to 9 membered heteroaryl, or 5 to 6 membered heteroaryl).

$R^{3A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{4A}$-substituted or unsubstituted alkyl (e.g., $C_1$-$C_8$ alkyl, $C_1$-$C_6$ alkyl, or $C_1$-$C_4$ alkyl), $R^{4A}$-substituted or unsubstituted heteroalkyl (e.g., 2 to 8 membered heteroalkyl, 2 to 6 membered heteroalkyl, or 2 to 4 membered heteroalkyl), $R^{4A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{4A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{4A}$-substituted or unsubstituted aryl (e.g., $C_6$-$C_{10}$ aryl, $C_{10}$ aryl, or phenyl), or $R^{4A}$-substituted or unsubstituted heteroaryl (e.g., 5 to 10 membered heteroaryl, 5 to 9 membered heteroaryl, or 5 to 6 membered heteroaryl).

In embodiments, $R^{3A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{3A}$ is $R^{4A}$-substituted or unsubstituted alkyl (e.g., $C_1$-$C_8$ alkyl, $C_1$-$C_6$ alkyl, or $C_1$-$C_4$ alkyl). In embodiments, $R^{3A}$ is $R^{4A}$-substituted (e.g., $C_1$-$C_8$ alkyl, $C_1$-$C_6$ alkyl, or $C_1$-$C_4$ alkyl). In embodiments, $R^{3A}$ is unsubstituted alkyl (e.g., $C_1$-$C_8$ alkyl, $C_1$-$C_6$ alkyl, or $C_1$-$C_4$ alkyl). In embodiments, $R^{3A}$ is $R^{4A}$-substituted or unsubstituted heteroalkyl (e.g., 2 to 8 membered heteroalkyl, 2 to 6 membered heteroalkyl, or 2 to 4 membered heteroalkyl). In embodiments, $R^{3A}$ is $R^{4A}$-substituted heteroalkyl (e.g., 2 to 8 membered heteroalkyl, 2 to 6 membered heteroalkyl, or 2 to 4 membered heteroalkyl). In embodiments, $R^{3A}$ is unsubstituted heteroalkyl (e.g., 2 to 8 membered heteroalkyl, 2 to 6 membered heteroalkyl, or 2 to 4 membered heteroalkyl). In embodiments, $R^{3A}$ is $R^{4A}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3A}$ is $R^{4A}$-substituted cycloalkyl (e.g., $C_3$-$C_8$ cycloalkyl, $C_3$-$C_6$ cycloalkyl, or $C_5$-$C_6$ cycloalkyl). In embodiments, $R^{3A}$ is unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3A}$ is $R^{4A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{3A}$ is $R^{4A}$-substituted heterocycloalkyl (e.g., 3 to 8 membered heterocycloalkyl, 3 to 6 membered heterocycloalkyl, or 5 to 6 membered heterocycloalkyl). In embodiments, $R^{3A}$ is unsubstituted heterocycloalkyl (e.g., 3 to 8 membered heterocycloalkyl, 3 to 6 membered heterocycloalkyl, or 5 to 6 membered heterocycloalkyl). In embodiments, $R^{3A}$ is $R^{4A}$-substituted or unsubstituted aryl (e.g., $C_6$-$C_{10}$ aryl, $C_{10}$ aryl, or phenyl). In embodiments, $R^{3A}$ is $R^{4A}$-substituted aryl (e.g., $C_6$-$C_{10}$ aryl, $C_{10}$ aryl, or phenyl). In embodiments, $R^{3A}$ is unsubstituted aryl (e.g., $C_6$-$C_{10}$ aryl, $C_{10}$ aryl, or phenyl). In embodiments, $R^{3A}$ is $R^{4A}$-substituted or unsubstituted heteroaryl (e.g., 5 to 10 membered heteroaryl, 5 to 9 membered heteroaryl, or 5 to 6 membered heteroaryl). In embodiments, $R^{3A}$ is $R^{4A}$-substituted heteroaryl (e.g., 5 to 10 membered heteroaryl, 5 to 9 membered heteroaryl, or 5 to 6 membered heteroaryl). In embodiments, $R^{3A}$ is unsubstituted heteroaryl (e.g., 5 to 10 membered heteroaryl, 5 to 9 membered heteroaryl, or 5 to 6 membered heteroaryl).

$R^{4A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{5A}$-substituted or unsubstituted alkyl (e.g., $C_1$-$C_8$ alkyl, $C_1$-$C_6$ alkyl, or $C_1$-$C_4$ alkyl), $R^{5A}$-substituted or unsubstituted heteroalkyl (e.g., 2 to 8 membered heteroalkyl, 2 to 6 membered heteroalkyl, or 2 to 4 membered heteroalkyl), $R^{5A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{5A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{5A}$-substituted or unsubstituted aryl (e.g., $C_6$-$C_{10}$ aryl, $C_{10}$ aryl, or phenyl), or $R^{5A}$-substituted or unsubstituted heteroaryl (e.g., 5 to 10 membered heteroaryl, 5 to 9 membered heteroaryl, or 5 to 6 membered heteroaryl).

In embodiments, $R^{4A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{4A}$ is $R^{5A}$-substituted or unsubstituted alkyl (e.g., $C_1$-$C_8$ alkyl, $C_1$-$C_6$ alkyl, or $C_1$-$C_4$ alkyl). In embodiments, $R^{4A}$ is $R^{5A}$-substituted (e.g., $C_1$-$C_8$ alkyl, $C_1$-$C_6$ alkyl, or $C_1$-$C_4$ alkyl). In embodiments, $R^{4A}$ is unsubstituted alkyl (e.g., $C_1$-$C_8$ alkyl, $C_1$-$C_6$ alkyl, or $C_1$-$C_4$ alkyl). In embodiments, $R^{4A}$ is $R^{5A}$-substituted or unsubstituted heteroalkyl (e.g., 2 to 8 membered heteroalkyl, 2 to 6 membered heteroalkyl, or 2 to 4 membered heteroalkyl). In embodiments, $R^{4A}$ is $R^{5A}$-substituted heteroalkyl (e.g., 2 to 8 membered heteroalkyl, 2 to 6 membered heteroalkyl, or 2 to 4 membered heteroalkyl). In embodiments, $R^{4A}$ is unsubstituted heteroalkyl (e.g., 2 to 8 membered heteroalkyl, 2 to 6 membered heteroalkyl, or 2 to 4 membered heteroalkyl). In embodiments, $R^{4A}$ is $R^{5A}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{4A}$ is $R^{5A}$-substituted cycloalkyl (e.g., $C_3$-$C_8$ cycloalkyl, $C_3$-$C_6$ cycloalkyl, or $C_5$-$C_6$ cycloalkyl). In embodiments, $R^{4A}$ is unsubstituted cycloalkyl (e.g., $C_3$-$C_8$ cycloalkyl, $C_3$-$C_6$ cycloalkyl, or $C_5$-$C_6$ cycloalkyl). In embodiments, $R^{4A}$ is $R^{5A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{4A}$ is $R^{5A}$-substituted heterocycloalkyl (e.g., 3 to 8 membered heterocycloalkyl, 3 to 6 membered heterocycloalkyl, or 5 to 6 membered heterocycloalkyl). In embodiments, $R^{4A}$ is unsubstituted heterocycloalkyl (e.g., 3 to 8 membered heterocycloalkyl, 3 to 6 membered heterocycloalkyl, or 5 to 6 membered heterocycloalkyl). In embodiments, $R^{4A}$ is $R^{5A}$-substituted or unsubstituted aryl (e.g., $C_6$-$C_{10}$ aryl, $C_{10}$ aryl, or phenyl). In embodiments, $R^{4A}$ is $R^{5A}$-substituted aryl (e.g., $C_6$-$C_{10}$ aryl, $C_{10}$ aryl, or phenyl). In embodiments, $R^{4A}$ is unsubstituted aryl (e.g., $C_6$-$C_{10}$ aryl, $C_{10}$ aryl, or phenyl). In embodiments, $R^{4A}$ is $R^{5A}$-substituted or unsubstituted heteroaryl (e.g., 5 to 10 membered heteroaryl, 5 to 9 membered heteroaryl, or 5 to 6 membered heteroaryl). In embodiments, $R^{4A}$ is $R^{5A}$-substituted heteroaryl (e.g., 5 to 10 membered heteroaryl, 5 to 9 membered heteroaryl, or 5 to 6 membered heteroaryl). In embodiments, $R^{4A}$ is unsubstituted heteroaryl (e.g., 5 to 10 membered heteroaryl, 5 to 9 membered heteroaryl, or 5 to 6 membered heteroaryl).

$R^{5A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{5A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{5A}$ is independently unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{1B}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{1B}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{1B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{3B}$-substituted or unsubstituted alkyl (e.g., $C_1$-$C_8$ alkyl, $C_1$-$C_6$ alkyl, or $C_1$-$C_4$ alkyl), $R^{3B}$-substituted or unsubstituted heteroalkyl (e.g., 2 to 8 membered heteroalkyl, 2 to 6 membered heteroalkyl, or 2 to 4 membered heteroalkyl), $R^{3B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{3B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{3B}$-substituted or unsubstituted aryl (e.g., $C_6$-$C_{10}$ aryl, $C_{10}$ aryl, or phenyl), or $R^{3B}$-substituted or unsubstituted heteroaryl (e.g., 5 to 10 membered heteroaryl, 5 to 9 membered heteroaryl, or 5 to 6 membered heteroaryl).

In embodiments, $R^{1B}$ is independently halogen, —$CF_3$, —$CCl_3$, $CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2$, —$OCH_2F$, —$OCH_2Cl$, —$OCH_2Br$, or —$OCH_2I$.

In embodiments, $R^{1B}$ is $R^{3B}$-substituted or unsubstituted alkyl (e.g., $C_1$-$C_8$ alkyl, $C_1$-$C_6$ alkyl, or $C_1$-$C_4$ alkyl). In embodiments, $R^{1B}$ is $R^{3B}$-substituted alkyl (e.g., $C_1$-$C_8$ alkyl, $C_1$-$C_6$ alkyl, or $C_1$-$C_4$ alkyl). In embodiments, $R^{1B}$ is an unsubstituted alkyl (e.g., $C_1$-$C_8$ alkyl, $C_1$-$C_6$ alkyl, or $C_1$-$C_4$ alkyl). In embodiments, $R^{1B}$ is $R^{3B}$-substituted or unsubstituted heteroalkyl (e.g., 2 to 8 membered heteroalkyl, 2 to 6 membered heteroalkyl, or 2 to 4 membered heteroalkyl). In embodiments, $R^{1B}$ is $R^{3B}$-substituted heteroalkyl (e.g., 2 to 8 membered heteroalkyl, 2 to 6 membered heteroalkyl, or 2 to 4 membered heteroalkyl). In embodiments, $R^{1B}$ is an unsubstituted heteroalkyl (e.g., 2 to 8 membered heteroalkyl, 2 to 6 membered heteroalkyl, or 2 to 4 membered heteroalkyl). In embodiments, $R^{1B}$ is $R^{3B}$-substituted or unsubstituted cycloalkyl (e.g., $C_3$-$C_8$ cycloalkyl, $C_3$-$C_6$ cycloalkyl, or $C_5$-$C_6$ cycloalkyl 1). In embodiments, $R^{1B}$ is $R^{3B}$-substituted cycloalkyl (e.g., $C_3$-$C_8$ cycloalkyl, $C_3$-$C_6$ cycloalkyl, or $C_5$-$C_6$ cycloalkyl). In embodiments, $R^{1B}$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1B}$ is $R^{3B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1B}$ is $R^{3B}$-substituted heterocycloalkyl (e.g., 3 to 8 membered heterocycloalkyl, 3 to 6 membered heterocycloalkyl, or 5 to 6 membered heterocycloalkyl). In embodiments, $R^{1B}$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^{1B}$ is $R^{3B}$-substituted or unsubstituted aryl (e.g., $C_6$-$C_{10}$ aryl, $C_{10}$ aryl, or phenyl). In embodiments, $R^{1B}$ is $R^{3B}$-substituted aryl (e.g., $C_6$-$C_{10}$ aryl, $C_{10}$ aryl, or phenyl). In embodiments, $R^{1B}$ is an unsubstituted aryl (e.g., $C_6$-$C_{10}$ aryl, $C_{10}$ aryl, or phenyl). In embodiments, $R^{1B}$ is $R^{3B}$-substituted or unsubstituted heteroaryl (e.g., 5 to 10 membered heteroaryl, 5 to 9 membered heteroaryl, or 5 to 6 membered heteroaryl). In embodiments, $R^{1B}$ is $R^{3B}$-substituted heteroaryl (e.g., 5 to 10 membered heteroaryl, 5 to 9 membered heteroaryl, or 5 to 6 membered heteroaryl). In embodiments, $R^{1B}$ is an unsubstituted heteroaryl (e.g., 5 to 10 membered heteroaryl, 5 to 9 membered heteroaryl, or 5 to 6 membered heteroaryl).

$R^{3B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{4B}$-substituted or unsubstituted alkyl (e.g., $C_1$-$C_8$ alkyl, $C_1$-$C_6$ alkyl, or $C_1$-$C_4$ alkyl), $R^{4B}$-substituted or unsubstituted heteroalkyl (e.g., 2 to 8 membered heteroalkyl, 2 to 6 membered heteroalkyl, or 2 to 4 membered heteroalkyl), $R^{4B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{4B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{4B}$-substituted or unsubstituted aryl (e.g., $C_6$-$C_{10}$ aryl, $C_{10}$ aryl, or phenyl), or $R^{4B}$-substituted or unsubstituted heteroaryl (e.g., 5 to 10 membered heteroaryl, 5 to 9 membered heteroaryl, or 5 to 6 membered heteroaryl).

In embodiments, $R^{3B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{3B}$ is $R^{4B}$-substituted or unsubstituted alkyl (e.g., $C_1$-$C_8$ alkyl, $C_1$-$C_6$ alkyl, or $C_1$-$C_4$ alkyl). In embodiments, $R^{3B}$ is $R^{4B}$-substituted (e.g., $C_1$-$C_8$ alkyl, $C_1$-$C_6$ alkyl, or $C_1$-$C_4$ alkyl). In embodiments, $R^{3B}$ is unsubstituted alkyl (e.g., $C_1$-$C_8$ alkyl, $C_1$-$C_6$ alkyl, or $C_1$-$C_4$ alkyl). In embodiments, $R^{3B}$ is $R^{4B}$-substituted or unsubstituted heteroalkyl (e.g., 2 to 8 membered heteroalkyl, 2 to 6 membered heteroalkyl, or 2 to 4 membered heteroalkyl). In embodiments, $R^{3B}$ is $R^{4B}$-substituted heteroalkyl (e.g., 2 to 8 membered heteroalkyl, 2 to 6 membered heteroalkyl, or 2 to 4 membered heteroalkyl). In embodiments, $R^{3B}$ is unsubstituted heteroalkyl (e.g., 2 to 8 membered heteroalkyl, 2 to 6 membered heteroalkyl, or 2 to 4 membered heteroalkyl). In embodiments, $R^{3B}$ is $R^{4B}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3B}$ is $R^{4B}$-substituted cycloalkyl (e.g., $C_3$-$C_8$ cycloalkyl, $C_3$-$C_6$ cycloalkyl, or $C_5$-$C_6$ cycloalkyl). In embodiments, $R^{3B}$ is unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3B}$ is $R^{4B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{3B}$ is $R^{4B}$-substituted heterocycloalkyl (e.g., 3 to 8 membered heterocycloalkyl, 3 to 6 membered heterocycloalkyl, or 5 to 6 membered heterocycloalkyl). In embodiments, $R^{3B}$ is unsubstituted heterocycloalkyl (e.g., 3 to 8 membered heterocycloalkyl, 3 to 6 membered heterocycloalkyl, or 5 to 6 membered heterocycloalkyl). In embodiments, $R^{3B}$ is $R^{4B}$-substituted or unsubstituted aryl (e.g., $C_6$-$C_{10}$ aryl, $C_{10}$ aryl, or phenyl). In embodiments, $R^{3B}$ is $R^{4B}$-substituted aryl (e.g., $C_6$-$C_{10}$ aryl, $C_{10}$ aryl, or phenyl). In embodiments, $R^{3B}$ is unsubstituted aryl (e.g., $C_6$-$C_{10}$ aryl, $C_{10}$ aryl, or phenyl). In embodiments, $R^{3B}$ is $R^{4B}$-substituted or unsubstituted heteroaryl (e.g., 5 to 10 membered heteroaryl, 5 to 9 membered heteroaryl, or 5 to 6 membered heteroaryl). In embodiments, $R^{3B}$ is $R^{4B}$-substituted heteroaryl (e.g., 5 to 10 membered heteroaryl, 5 to 9 membered heteroaryl, or 5 to 6 membered heteroaryl). In embodiments, $R^{3B}$ is unsubstituted heteroaryl (e.g., 5 to 10 membered heteroaryl, 5 to 9 membered heteroaryl, or 5 to 6 membered heteroaryl).

$R^{4B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{5B}$-substituted or unsubstituted alkyl (e.g., $C_1$-$C_8$ alkyl, $C_1$-$C_6$ alkyl, or $C_1$-$C_4$ alkyl), $R^{5B}$-substituted or unsubstituted heteroalkyl (e.g., 2 to 8 membered heteroalkyl, 2 to 6 membered heteroalkyl, or 2 to 4 membered heteroalkyl), $R^{5B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{5B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{5B}$-substituted or unsubstituted aryl (e.g., $C_6$-$C_{10}$ aryl, $C_{10}$ aryl, or phenyl), or $R^{5B}$-substituted or unsubstituted heteroaryl (e.g., 5 to 10 membered heteroaryl, 5 to 9 membered heteroaryl, or 5 to 6 membered heteroaryl).

In embodiments, $R^{4B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{4B}$ is $R^{5B}$-substituted or unsubstituted alkyl (e.g., $C_1$-$C_8$ alkyl, $C_1$-$C_6$ alkyl, or $C_1$-$C_4$ alkyl). In embodiments, $R^{4B}$ is $R^{5B}$-substituted (e.g., $C_1$-$C_8$ alkyl, $C_1$-$C_6$ alkyl, or $C_1$-$C_4$ alkyl). In embodiments, $R^{4B}$ is unsubstituted alkyl (e.g., $C_1$-$C_8$ alkyl, $C_1$-$C_6$ alkyl, or $C_1$-$C_4$ alkyl). In embodiments, $R^{4B}$ is $R^{5B}$-substituted or unsubstituted heteroalkyl (e.g., 2 to 8 membered heteroalkyl, 2 to 6 membered heteroalkyl, or 2 to 4 membered heteroalkyl). In embodiments, $R^{4B}$ is $R^{5B}$-substituted heteroalkyl (e.g., 2 to 8 membered heteroalkyl, 2 to 6 membered heteroalkyl, or 2 to 4 membered heteroalkyl). In embodiments, $R^{4B}$ is unsubstituted heteroalkyl (e.g., 2 to 8 membered heteroalkyl, 2 to 6 membered heteroalkyl, or 2 to 4 membered heteroalkyl). In embodiments, $R^{4B}$ is $R^{5B}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{4B}$ is $R^{5B}$-substituted cycloalkyl (e.g., $C_3$-$C_8$ cycloalkyl, $C_3$-$C_6$ cycloalkyl, or $C_5$-$C_6$ cycloalkyl). In embodiments, $R^{4B}$ is unsubstituted cycloalkyl (e.g., $C_3$-$C_8$ cycloalkyl, $C_3$-$C_6$ cycloalkyl, or $C_5$-$C_6$ cycloalkyl). In embodiments, $R^{4B}$ is $R^{5B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{4B}$ is $R^{5B}$-substituted heterocycloalkyl (e.g., 3 to 8 membered heterocycloalkyl, 3 to 6 membered heterocycloalkyl, or 5 to 6 membered heterocycloalkyl). In embodiments, $R^{4B}$ is unsubstituted heterocycloalkyl (e.g., 3 to 8 membered heterocycloalkyl, 3 to 6 membered heterocycloalkyl, or 5 to 6 membered heterocycloalkyl). In embodiments, $R^{4B}$ is $R^{5B}$-substituted or unsubstituted aryl (e.g., $C_6$-$C_{10}$ aryl, $C_{10}$ aryl, or phenyl). In embodiments, $R^{4B}$ is $R^{5B}$-substituted aryl (e.g., $C_6$-$C_{10}$ aryl, $C_{10}$ aryl, or phenyl). In embodiments, $R^{4B}$ is unsubstituted aryl (e.g., $C_6$-$C_{10}$ aryl, $C_{10}$ aryl, or phenyl). In embodiments, $R^{4B}$ is $R^{5B}$-substituted or unsubstituted heteroaryl (e.g., 5 to 10 membered heteroaryl, 5 to 9 membered heteroaryl, or 5 to 6 membered heteroaryl). In embodiments, $R^{4B}$ is $R^{5B}$-substituted heteroaryl (e.g., 5 to 10 membered heteroaryl, 5 to 9 membered heteroaryl, or 5 to 6 membered heteroaryl). In embodiments, $R^{4B}$ is unsubstituted heteroaryl (e.g., 5 to 10 membered heteroaryl, 5 to 9 membered heteroaryl, or 5 to 6 membered heteroaryl).

$R^{5B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{5B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{5B}$ is independently unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^1$ is —CN, —OH, a substituted alkyl, substituted heteroalkyl, unsubstituted aryl, or unsubstituted heteroaryl. In embodiments, $R^1$ is —CN. In embodiments, $R^1$ is —OH. In embodiments, $R^1$ is a substituted alkyl. In embodiments, $R^1$ is $CH_2$—$CH_2$—OH. In embodiments, $R^1$ is a substituted heteroalkyl. In embodiments, $R^1$ is $CH_2$—C(=O)—$OCH_3$. In embodiments, $R^1$ is an unsubstituted aryl. In embodiments, $R^1$ is phenyl. In embodiments, $R^1$ is an unsubstituted heteroaryl. In embodiments, $R^1$ is pyridinyl.

In embodiments, $R^2$ is hydrogen or unsubstituted $C_1$-$C_4$ alkyl. In embodiments, $R^2$ is hydrogen, —$CH_3$, or —$CH_2CH_3$. In embodiments, $R^2$ is hydrogen. In embodiments, $R^2$ is —$CH_3$. In embodiments, $R^2$ is —$CH_2CH_3$.

In embodiments, the compound has the formula (IIa):

(IIa)

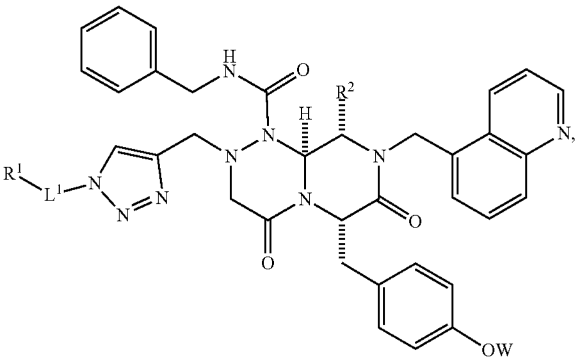

wherein $L^1$, $R^1$, $R^2$ are as defined above, including embodiments thereof.

In embodiments, the compound has the formula (IIb):

(IIb)

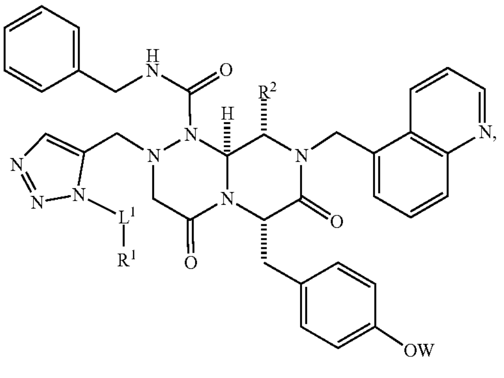

wherein $L^1$, $R^1$, $R^2$ are as defined above, including embodiments thereof.

In embodiments, the compound has the formula (IIc):

(IIc)

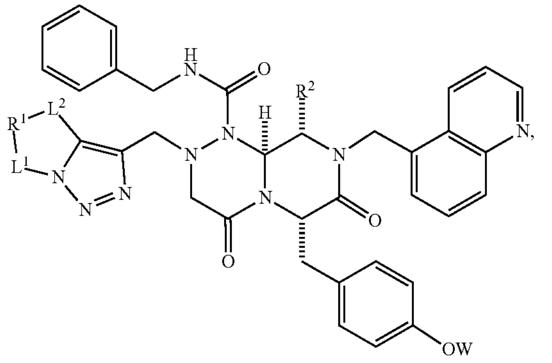

wherein $L^1$, $L^2$, $R^1$, $R^2$ are as defined above, including embodiments thereof.

In embodiments, the compound has the formula (IIIa):

(IIIa)

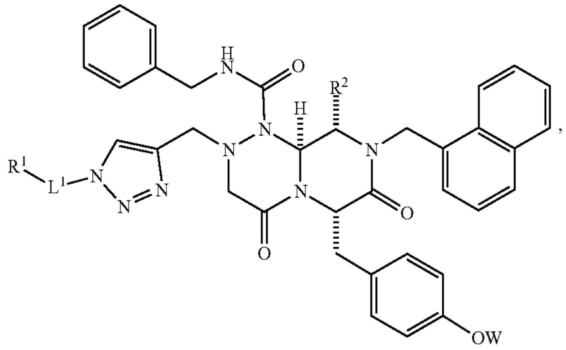

wherein $L^1$, $R^1$, $R^2$ are as defined above, including embodiments thereof.

In embodiments, the compound has the formula (IIIb):

(IIIb)

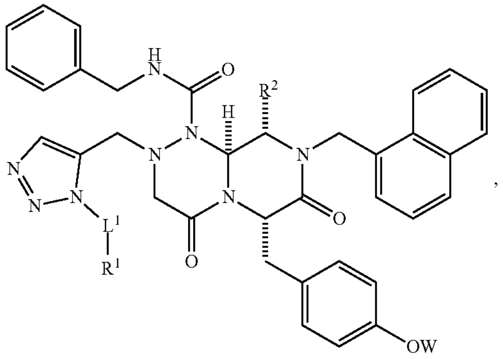

wherein $L^1$, $R^1$, $R^2$ are as defined above, including embodiments thereof.

In embodiments, the compound has the formula (IIIc):

(IIIc)

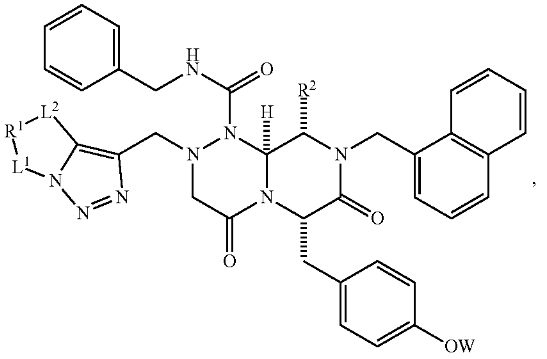

wherein $L^1$, $L^2$, $R^1$, $R^2$ are as defined above, including embodiments thereof.

In embodiments, the compound has the formula (IVa):

(IVa)

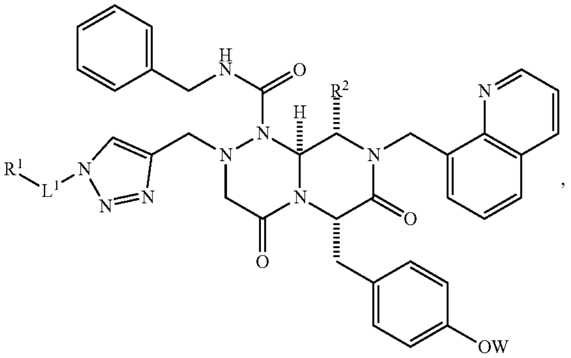

wherein $L^1$, $R^1$, $R^2$ are as defined above, including embodiments thereof.

In embodiments, the compound has the formula (IVb):

(IVb)

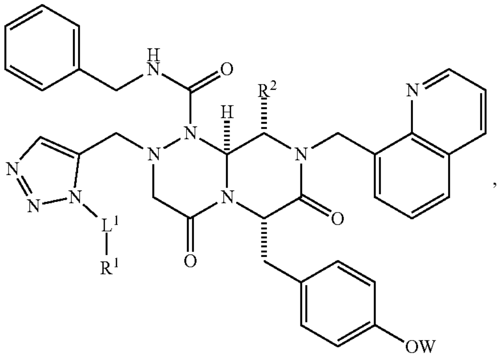

wherein $L^1$, $R^1$, $R^2$ are as defined above, including embodiments thereof.

In embodiments, the compound has the formula (IVc):

(IVc)

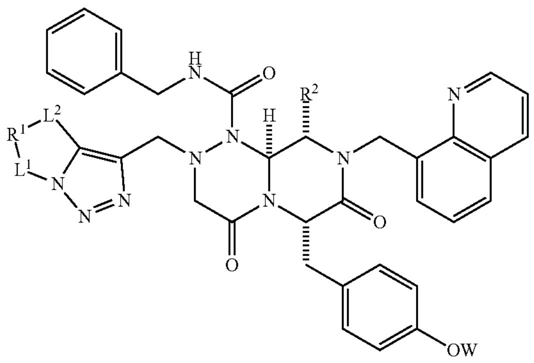

, wherein $L^1$, $L^2$, $R^1$, $R^2$ are as defined above, including embodiments thereof.

In embodiments, each $R^{1A}$ and $R^{1B}$ are independently hydrogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —COOH, —$CONH_2$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_{10}$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, each $R^{1A}$ and $R^{1B}$ are independently hydrogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —COOH, —$CONH_2$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

n is an integer from 0 to 4. In embodiments, n is 0. In embodiments, n is 1. In embodiments, n is 2. In embodiments, n is 3. In embodiments, n is 4.

$X^1$ is halogen. In embodiments, halogen is —F, —Cl, —Br, —I. In embodiments, $X^1$ is —F. In embodiments, $X^1$ is —Cl. In embodiments, $X^1$ is —Br. In embodiments, $X^1$ is —I.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl.

In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently unsubstituted alkyl, unsubstituted heteroalkyl, unsubstituted cycloalkyl, unsubstituted heterocycloalkyl, unsubstituted aryl, or unsubstituted heteroaryl.

In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted (e.g., substituted with a substituent group, a size-limited substituent group, or lower substituent group) or unsubstituted alkyl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted (e.g., substituted with a substituent group, a size-limited substituent group, or lower substituent group) alkyl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently unsubstituted alkyl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted or unsubstituted alkyl (e.g., $C_1$-$C_8$ alkyl, $C_1$-$C_6$ alkyl, or $C_1$-$C_4$ alkyl). In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted alkyl alkyl (e.g., $C_1$-$C_8$ alkyl, $C_1$-$C_6$ alkyl, or $C_1$-$C_4$ alkyl). In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently unsubstituted alkyl alkyl (e.g., $C_1$-$C_8$ alkyl, $C_1$-$C_6$ alkyl, or $C_1$-$C_4$ alkyl).

In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted (e.g., substituted with a substituent group, a size-limited substituent group, or lower substituent group) or unsubstituted heteroalkyl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted (e.g., substituted with a substituent group, a size-limited substituent group, or lower substituent group) heteroalkyl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently unsubstituted heteroalkyl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted or unsubstituted heteroalkyl (e.g., 2 to 8 membered, 2 to 6 membered, 4 to 6 membered, 2 to 3 membered, or 4 to 5 membered). In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted heteroalkyl (e.g., 2 to 8 membered, 2 to 6 membered, or 2 to 4 membered). In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently an unsubstituted heteroalkyl (e.g., 2 to 8 membered, 2 to 6 membered, or 2 to 4 membered).

In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted (e.g., substituted with a substituent group, a size-limited substituent group, or lower substituent group) or unsubstituted cycloalkyl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted (e.g., substituted with a substituent group, a size-limited substituent group, or lower substituent group) cycloalkyl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently an unsubstituted cycloalkyl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted cycloalkyl (e.g., $C_3$-$C_8$ cycloalkyl, $C_3$-$C_6$ cycloalkyl, or $C_5$-$C_6$ cycloalkyl). In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently unsubstituted cycloalkyl (e.g., $C_3$-$C_8$ cycloalkyl, $C_3$-$C_6$ cycloalkyl, or $C_5$-$C_6$ cycloalkyl).

In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted (e.g., substituted with a substituent group, a size-limited substituent group, or lower substituent group) or unsubstituted heterocycloalkyl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$, are independently substituted (e.g., substituted with a substituent group, a size-limited substituent group, or lower substituent group) heterocycloalkyl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently an unsubstituted heterocycloalkyl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted or unsubstituted heterocycloalkyl (e.g., 3 to 8 membered, 3 to 6 membered, or 5 to 6 membered). In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted heterocycloalkyl (e.g., 3 to 8 membered, 3 to 6 membered, or 5 to 6 membered). In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently an unsubstituted heterocycloalkyl (e.g., 3 to 8 membered, 3 to 6 membered, or 5 to 6 membered).

In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted (e.g., substituted with a substituent group, a size-limited substituent group, or lower substituent group) or unsubstituted aryl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted (e.g., substituted with a substituent group, a size-limited substituent group, or lower substituent group) aryl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently an unsubstituted aryl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted or unsubstituted aryl (e.g., $C_6$-$C_{10}$ aryl, $C_{10}$ aryl, or phenyl). In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted aryl (e.g., $C_6$-$C_{10}$ aryl, $C_{10}$ aryl, or phenyl). In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently an unsubstituted aryl (e.g., $C_6$-$C_{10}$ aryl, $C_{10}$ aryl, or phenyl).

In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted (e.g., substituted with a substituent group, a size-limited substituent group, or lower substituent group) or unsubstituted heteroaryl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted (e.g., substituted with a substituent group, a size-limited substituent group, or lower substituent group) heteroaryl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently an unsubstituted heteroaryl. In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted or unsubstituted heteroaryl (e.g., 5 to 10 membered heteroaryl, 5 to 9 membered heteroaryl, or 5 to 6 membered heteroaryl). In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently substituted heteroaryl (e.g., 5 to 10 membered heteroaryl, 5 to 9 membered heteroaryl, or 5 to 6 membered heteroaryl). In embodiments, $R^1$, $R^{1A}$, $R^{1B}$, $R^2$, $R^3$, $R^{3A}$, $R^{3B}$, $R^4$, $R^{4A}$, $R^{4A}$, $R^5$, $R^{5A}$, and $R^{5B}$ are independently an unsubstituted heteroaryl (e.g., 5 to 10 membered heteroaryl, 5 to 9 membered heteroaryl, or 5 to 6 membered heteroaryl).

In embodiments, the compound is:

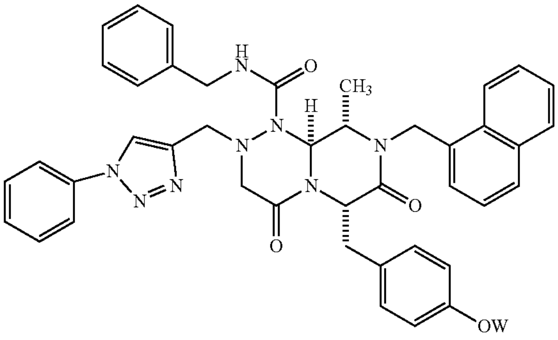

,

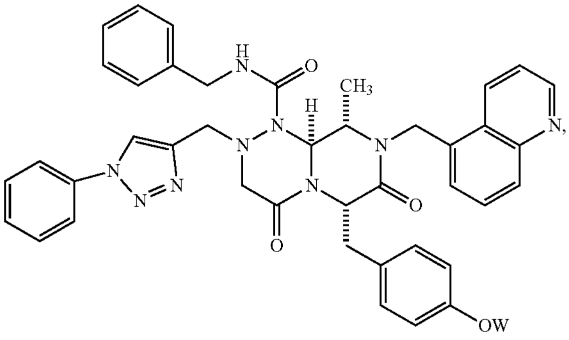

-continued

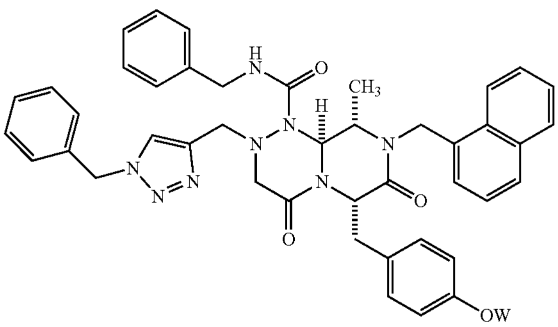

,

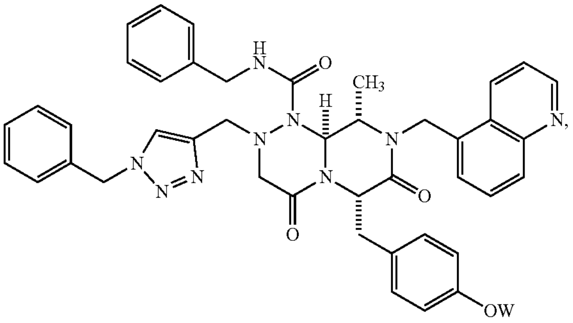

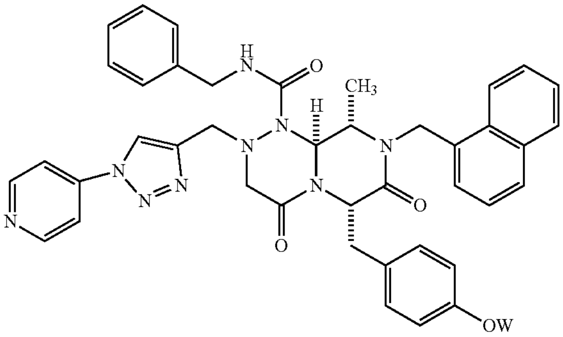

,

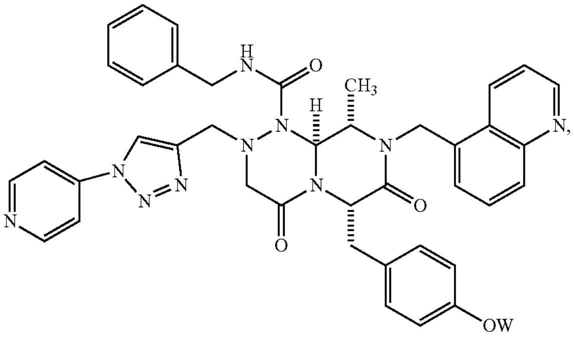

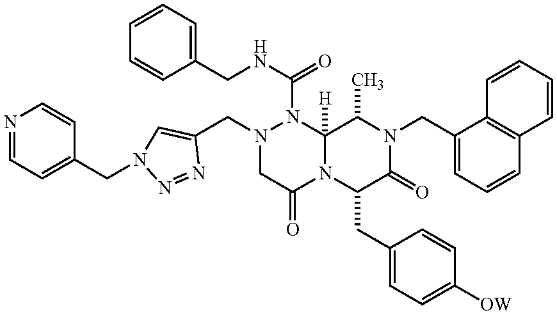

,

-continued
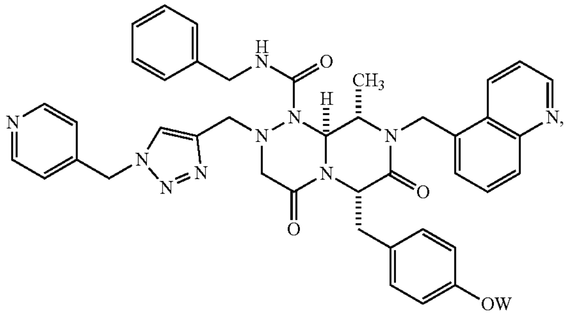
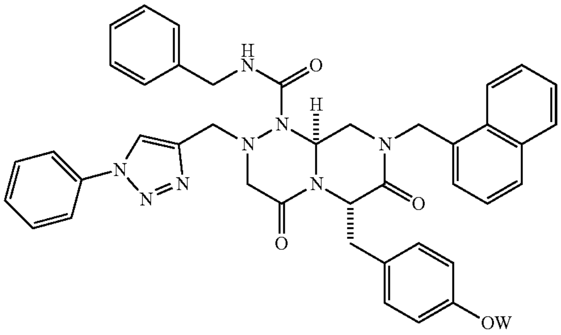
,
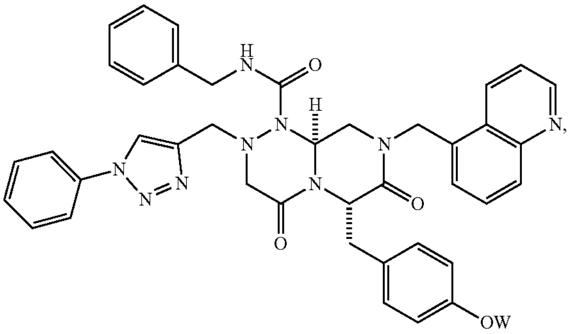
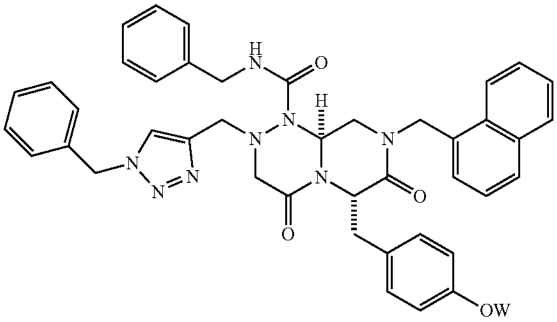
,
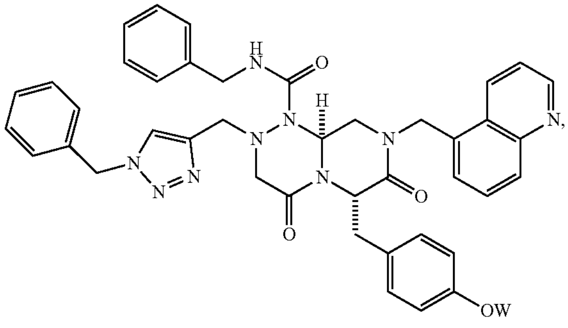
-continued
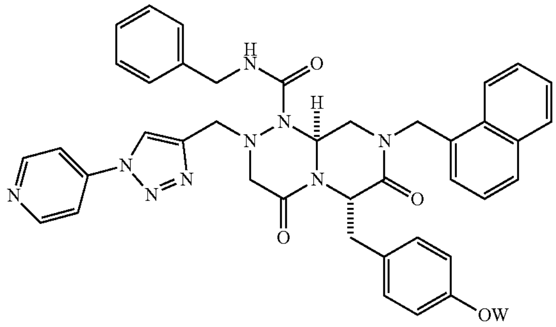
,
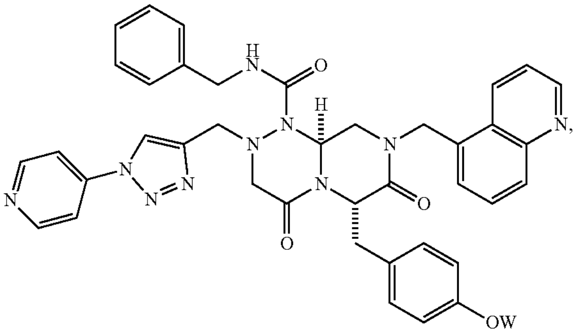
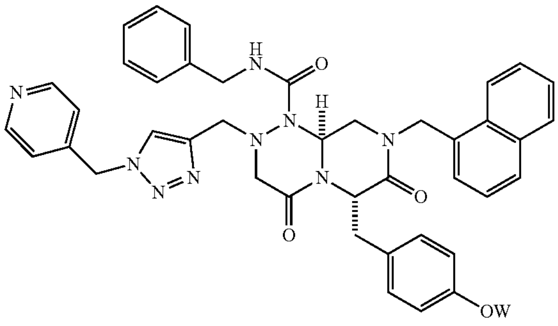
,
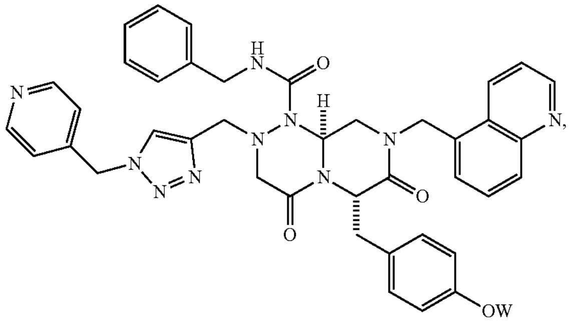
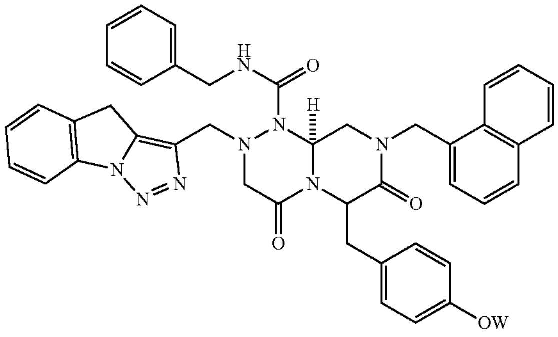
,

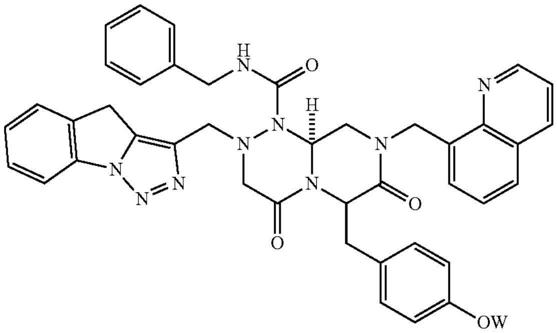
,
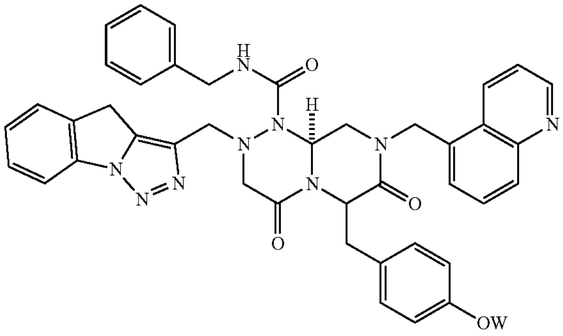
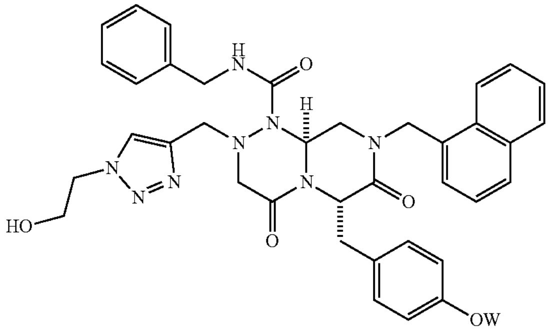
,
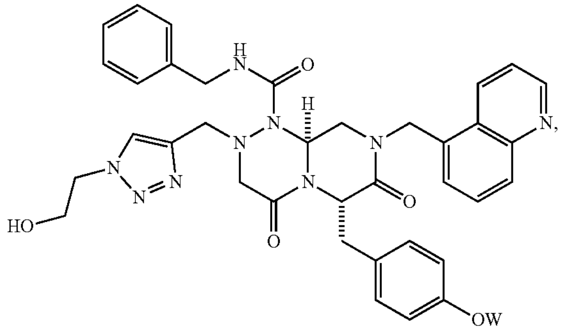
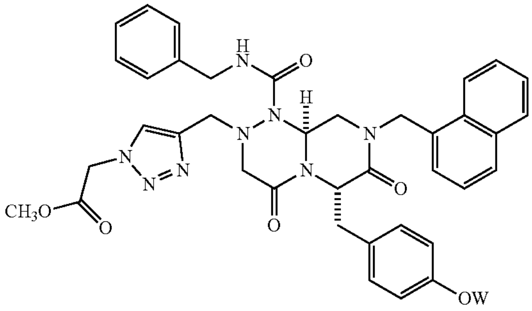
or
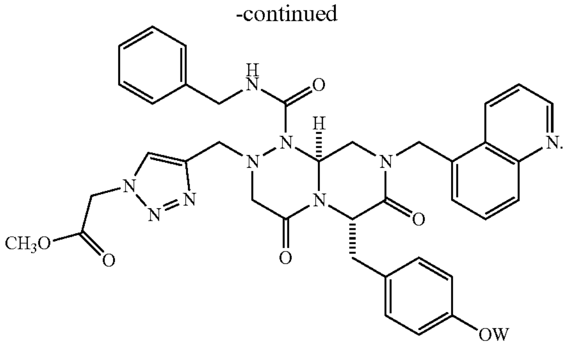
In embodiments, the compound has the formula:
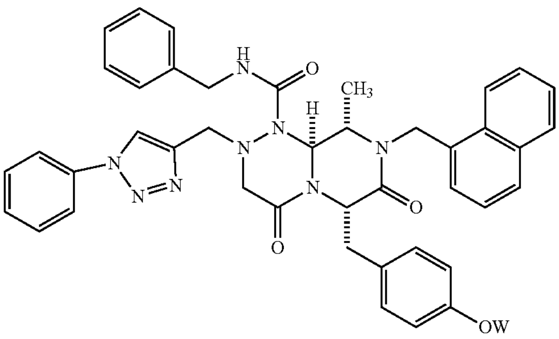
.
In embodiments, the compound has the formula:
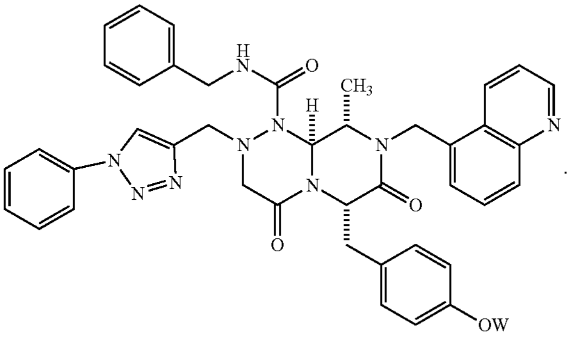
.
In embodiments, the compound has the formula:
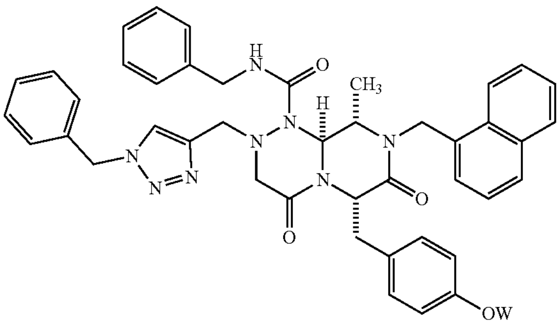
.

In embodiments, the compound has the formula:
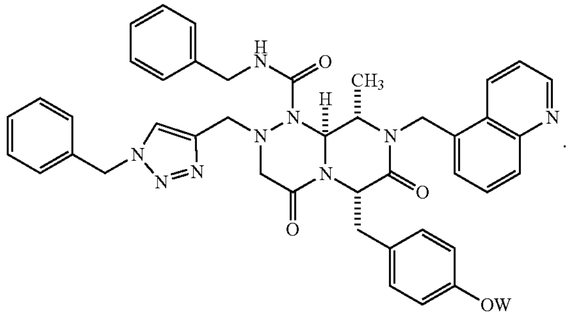
In embodiments, the compound has the formula:
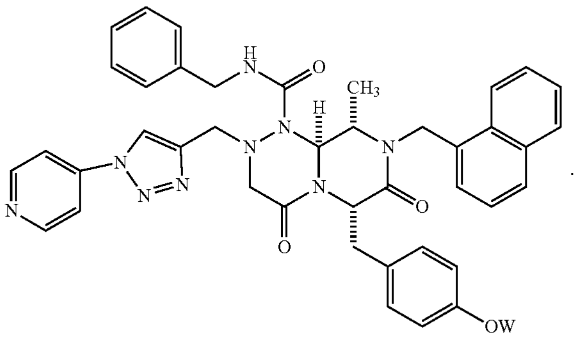
In embodiments, the compound has the formula:
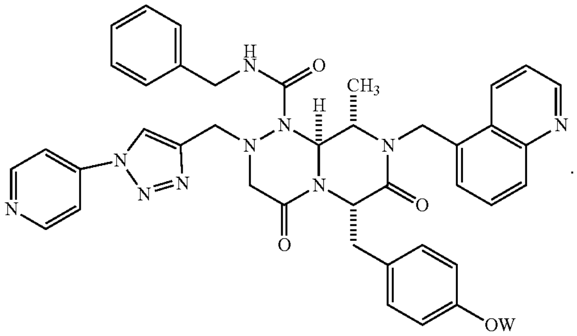
In embodiments, the compound has the formula:
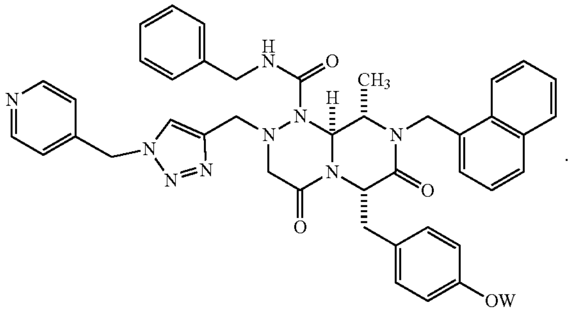
In embodiments, the compound has the formula:
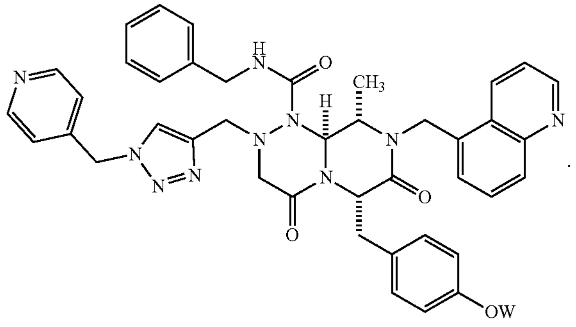
In embodiments, the compound has the formula:
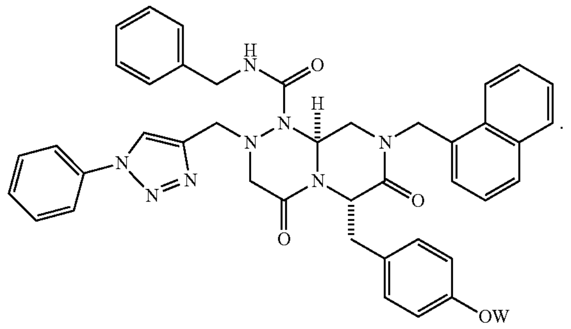
In embodiments, the compound has the formula:
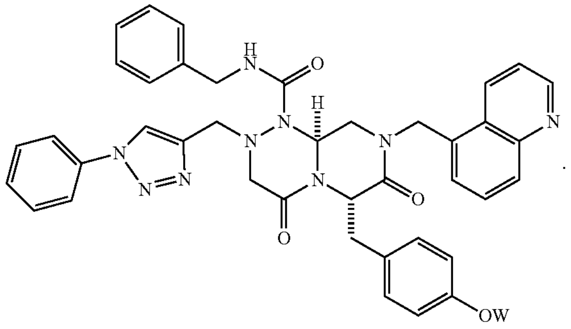
In embodiments, the compound has the formula:
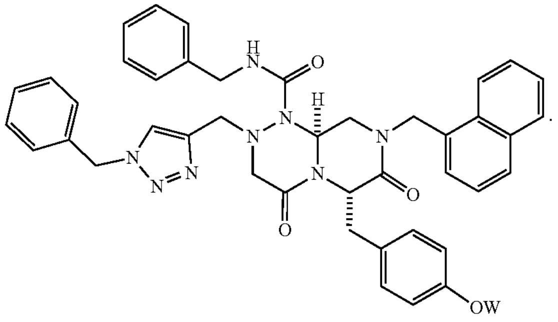

In embodiments, the compound has the formula:
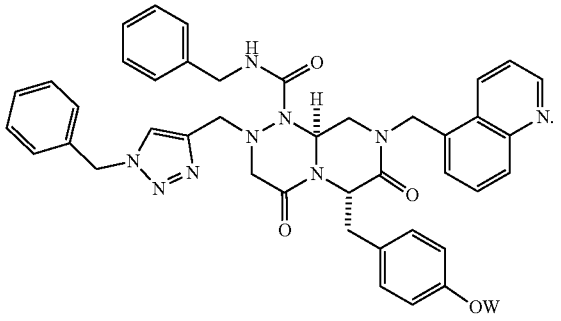
In embodiments, the compound has the formula:
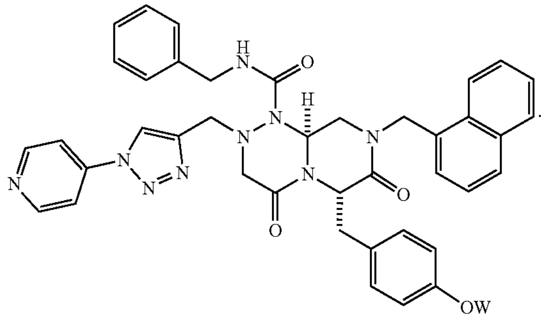
In embodiments, the compound has the formula:
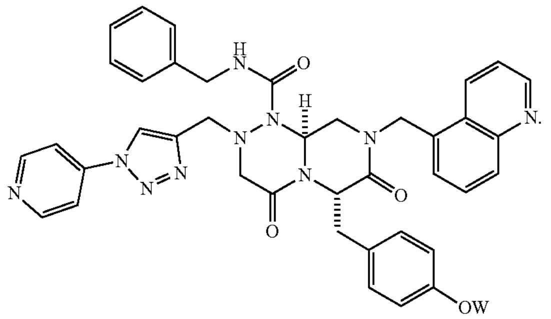
In embodiments, the compound has the formula:
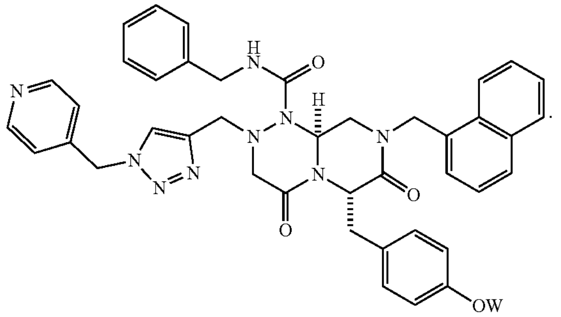
In embodiments, the compound has the formula:
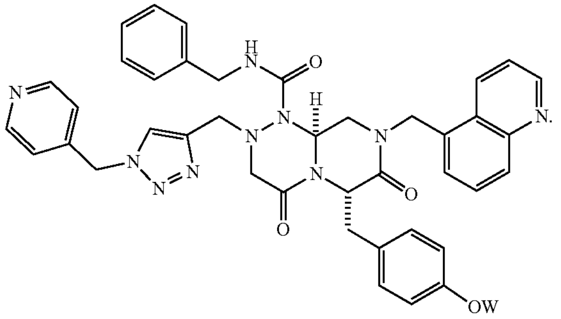
In embodiments, the compound has the formula:
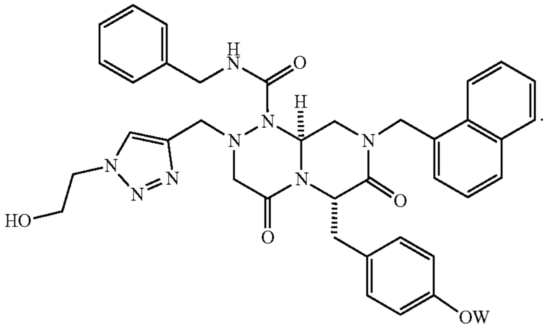
In embodiments, the compound has the formula:
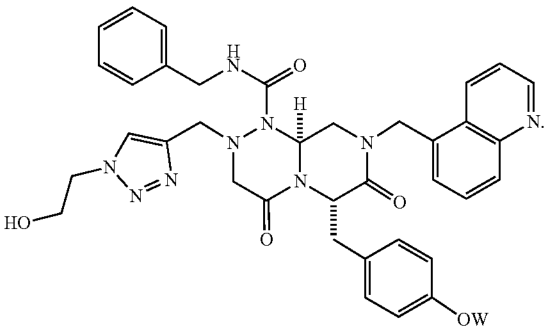
In embodiments, the compound has the formula:
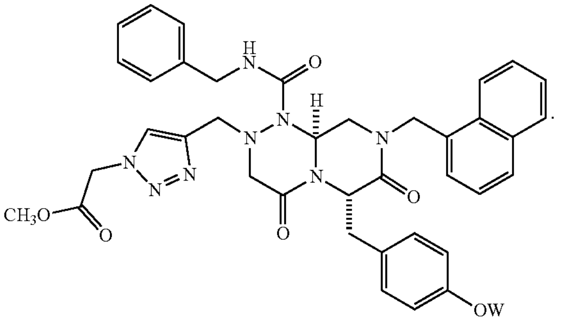

In embodiments, the compound has the formula:

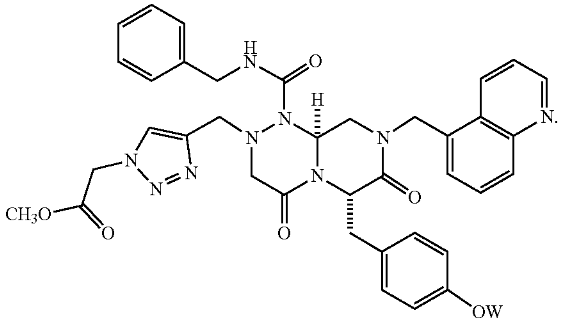

In embodiments, the compound has the formula:

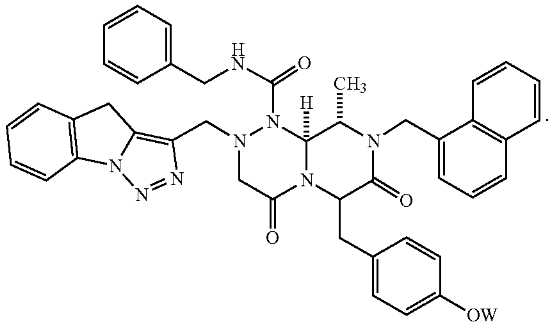

In embodiments, the compound has the formula:

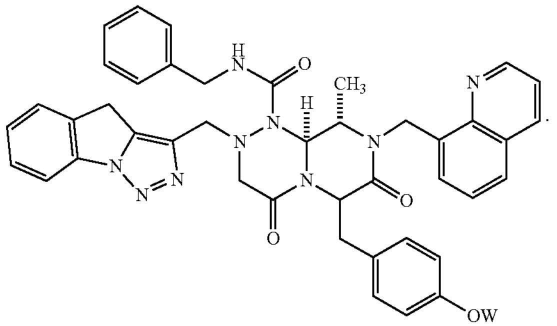

In embodiments, the compound has the formula:

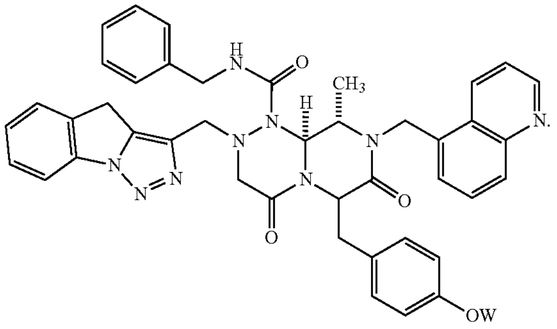

In embodiments, the compound has the formula as described elsewhere herein, for example within a table, claim or example.

III. Pharmaceutical and Cosmeceutical Compositions

In an aspect, there is provided a pharmaceutical composition, including a compound as described herein, including embodiments (e.g., structural Formulae (Ia), (Ib), (Ic), (Ia'), (Ib'), (Ic'), (IIa), (IIb), (IIc), (IIIa), (IIIb), (IIIc), (IVa), (IVb), and (IVc)) and a pharmaceutically acceptable excipient.

The compounds as described herein of the present disclosure may be in the form of compositions suitable for administration to a subject. In general, such compositions are "pharmaceutical compositions" comprising a compound (e.g., compounds described herein) and one or more pharmaceutically acceptable or physiologically acceptable excipients (e.g., acceptable diluents or carriers). In certain embodiments, the compounds are present in a therapeutically effective amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein.

The pharmaceutical compositions containing the active ingredient (e.g., an inhibitor of Wnt/catenin signaling pathway, or a compound described herein) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients that are suitable for the manufacture thereof. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, corn oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation.

Dispersible powders and granules suitable for preparation of an aqueous suspension by the addition of water provide the active ingredient in admixture with a dispersing or wetting agent, and optionally one or more suspending agents and/or preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of a compound described herein contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate-buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer; N-(2-Hydroxyethyl)piperazine-N'-(2-ethanesulfonic acid) (HEPES); 2-(N-Morpholino)ethanesulfonic acid (MES); 2-(N-Morpholino)ethanesulfonic acid sodium salt (MES); 3-(N-Morpholino)propanesulfonic acid (MOPS); and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time-delay material such as glyceryl monostearate or glyceryl stearate alone, or in combination with a wax, may be employed. Any drug delivery apparatus may be used to deliver a Wnt/catenin signaling pathway inhibitor, including implants (e.g., implantable pumps) and catheter systems, slow injection pumps and devices, all of which are well known to the skilled artisan.

Depot injections, which are generally administered subcutaneously or intramuscularly, may also be utilized to release a compound disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor® EL (BASF, Parsippany, NJ) or phosphate buffered saline (PBS), ethanol, polyol (e.g., glycerol, propylene glycol, and liquid polyethylene glycol), and suitable mixtures thereof. In addition, sterile fixed oils are conventionally employed as a solvent or suspending medium; for this purpose, any bland fixed oil may be employed, including synthetic mono- or diglycerides. Moreover, fatty acids, such as oleic acid, find use in the preparation of injectables. Prolonged absorption of particular injectable formulations can be achieved by including an agent that delays absorption (e.g., aluminum monostearate or gelatin).

The present disclosure contemplates the administration of the compounds described herein in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The compounds described herein contemplated by the present disclosure may be in the form of any other suitable pharmaceutical composition (e.g., sprays for nasal or inhalation use) currently known or developed in the future.

IV. Methods of Use

In another aspect, there is provided a method of treating a Wnt/catenin signaling pathway/CBP/catenin signaling pathway modulated disease or disorder in a subject in need of the treatment, the method including administering an effective amount of a compound described herein, including embodiments (e.g., structural Formulae (Ia), (Ib), (Ic), (Ia'), (Ib'), (Ic'), (IIa), (IIb), (IIc), (IIIa), (IIIb), (IIIc), (IVa), (IVb), and (IVc)), or a pharmaceutically acceptable salt thereof. In another aspect, there is provided a method of treating a Wnt/catenin signaling pathway/CBP/catenin signaling pathway modulated disease or disorder in a subject in need of the treatment, the method including administering an effective amount of a compound described herein, including embodiments (e.g., structural Formulae (Ia), (Ib), (Ic), (Ia'), (Ib'), (Ic'), (IIa), (IIb), (IIc), (IIIa), (IIIb), (IIIc), (IVa), (IVb), and (IVc)), or a pharmaceutically acceptable salt thereof.

In an aspect, there is provided a method of treating or preventing a Wnt/catenin signaling pathway/CBP/catenin signaling pathway modulated disease or disorder, including administering to a patient in need thereof a therapeutically effective amount of a compound or pharmaceutical composition as described herein, including embodiments (e.g., structural Formulae (Ia), (Ib), (Ic), (Ia'), (Ib'), (Ic'), (IIa), (IIb), (IIc), (IIIa), (IIIb), (IIIc), (IVa), (IVb), and (IVc)) or a pharmaceutically acceptable salt thereof. In an aspect, there is provided a method of treating or preventing a Wnt/catenin signaling pathway/CBP/catenin signaling pathway modulated disease or disorder, including administering to a patient in need thereof a therapeutically effective amount of a compound or pharmaceutical composition as described herein, including embodiments (e.g., structural Formulae (Ia), (Ib), (Ic), (Ia'), (Ib'), (Ic'), (IIa), (IIb), (IIc), (IIIa), (IIIb), (IIIc), (IVa), (IVb), and (IVc)) or a pharmaceutically acceptable salt thereof.

In accordance with the present disclosure, a compound (e.g., a compound described herein) or pharmaceutical salt thereof can be used to treat or prevent a proliferative condition or disorder, including a cancer, for example, brain cancer, glioma, glioblastoma, neuroblastoma, prostate cancer, colorectal cancer, pancreatic cancer, medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer. The present disclosure also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The disclosure contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In some embodiments, the tumor or cancer is breast cancer, ovarian cancer, colon adenocarcinoma, lung adenocarcinoma, lung small cell carcinoma, pancreatic adenocarcinoma, pancreatic neutoendocrine tumors, glioblastoma, prostate cancer, hepatocellular carcinoma, myeloma, leukemia, and lymphoma. The use of the term(s) cancer-related diseases, disorders and conditions is meant to refer broadly to conditions that are associated, directly or indirectly, with cancer, and includes, e.g., angiogenesis and precancerous conditions such as dysplasia. In embodiments, the cancer is breast cancer, ovarian cancer, colon adenocarcinoma, lung adenocarcinoma, lung small cell carcinoma, pancreatic adenocarcinoma, pancreatic neutoendocrine tumors, glioblastoma, prostate cancer, hepatocellular carcinoma, myeloma, leukemia, and lymphoma.

In embodiments, a cancer can be metastatic or at risk of becoming metastatic, or may occur in a diffuse tissue, including cancers of the blood or bone marrow (e.g., leukemia). In some further embodiments, the compounds of the disclosure can be used to overcome T-cell tolerance.

In some embodiments, the present disclosure provides methods for treating a proliferative condition, cancer, tumor, or precancerous condition with a compound described herein and at least one additional therapeutic or diagnostic agent, examples of which are set forth elsewhere herein.

The present disclosure provides methods for treating and/or preventing a proliferative condition, cancer, tumor, or precancerous disease, disorder or condition with a compound described herein.

In embodiments drawn to methods of treating cancer, the administration of a therapeutically effective amount of a compound described herein results in a cancer survival rate greater than the cancer survival rate observed by not administering a therapeutically effective amount of the compound. In further embodiments drawn to methods of treating cancer, the administration of a therapeutically effective amount of a compound described herein results in a reduction of tumor size or a slowing of tumor growth greater than reduction of tumor size or tumor growth observed following lack of administration of a therapeutically effective amount of the compound.

Embodiments of the present disclosure contemplate the administration of the compounds described herein to a subject for the treatment or prevention of any other disorder that may benefit from at least some level of Wnt/catenin signaling pathway/CBP/catenin signaling pathway modulation. Such diseases, disorders and conditions may include, for example, fibrotic disorders (pulmonary fibrosis, idiopathic pulmonary fibrosis, familial pulmonary fibrosis, hepatic fibrosis, renal fibrosis, cardiac fibrosis, systemic fibrosis) and metabolic disorders (diabetes).

In embodiments, a Wnt/catenin signaling pathway/CBP/catenin signaling pathway-mediated disease or disorder is cancer, fibrotic disease or disorder, or metabolic disorder. In embodiments, a Wnt/catenin signaling pathway/CBP/catenin signaling pathway-mediated disease or disorder is cancer. In embodiments, a Wnt/catenin signaling pathway/CBP/catenin signaling pathway-mediated disease or disorder is a fibrotic disease or disorder. In embodiments, a Wnt/catenin signaling pathway/CBP/catenin signaling pathway-mediated disease or disorder is a metabolic disease or disorder.

In embodiments, the Wnt/catenin signaling pathway/CBP/catenin signaling pathway-mediated disease or disorder is cancer. In certain embodiments, cancer includes, but is not limited to, brain cancer, glioma, glioblastoma, neuroblastoma, prostate cancer, colorectal cancer, pancreatic cancer, medulloblastoma, melanoma, cervical cancer, gastric cancer, ovarian cancer, lung cancer, cancer of the head, Hodgkin's Disease, and Non-Hodgkin's Lymphomas.

In embodiments, a method of treating the Wnt/catenin signaling pathway/CBP/catenin signaling pathway-mediated cancer comprises administering to a patient in need thereof a therapeutically effective amount of a compound or pharmaceutical composition as described herein, including embodiments (e.g., structural Formulae (Ia), (Ib), (Ia'), (Ib'), (IIa), (IIb), (IIIa), (IIIb), (IVa), and (IVb) or a pharmaceutically acceptable salt thereof).

In embodiments, the Wnt/catenin signaling pathway/CBP/catenin signaling pathway-mediated disease or disorder is fibritoc disease or disorder. In certain embodiments, fibritoc disease or disorder is pulmonary fibrosis, idiopathic pulmonary fibrosis, familial pulmonary fibrosis, hepatic fibrosis, renal fibrosis, cardiac fibrosis, or systemic fibrosis.

In embodiments, a method of treating the Wnt/catenin signaling pathway/CBP/catenin signaling pathway-mediated fibritoc disease or disorder comprises administering to a patient in need thereof a therapeutically effective amount of a compound or pharmaceutical composition as described herein, including embodiments (e.g., structural Formulae (Ia), (Ib), (Ia'), (Ib'), (IIa), (IIb), (IIIa), (IIIb), (IVa), and (IVb)), or a pharmaceutically acceptable salt thereof).

In embodiments, the Wnt/catenin signaling pathway/CBP/catenin signaling pathway-mediated disease or disorder is metabolic disorder. In embodiments, the Wnt/catenin signaling pathway/CBP/catenin signaling pathway-mediated disease or disorder is diabetes. In certain embodiments, diabetes is type 1 diabetes, type 2 diabetes, gestational diabetes, monogenic diabetes, or cystic fibrosis-related diabetes.

In embodiments, the Wnt/catenin signaling pathway/CBP/catenin signaling pathway-mediated disease or disorder is a neurodevelopmental or neurodegenerative disorder. In certain embodiments, austism spectrum disorder, schizophrenia, Alzheimer's disease, Parkinson's disease, amyotrophic lateral sclerosis (ALS), or multiple scleroris (MS).

In embodiments, a method of treating the Wnt/catenin signaling pathway/CBP/catenin signaling pathway-mediated diabetes comprises administering to a patient in need thereof a therapeutically effective amount of a compound or pharmaceutical composition as described herein, including embodiments (e.g., structural Formulae (Ia), (Ib), (Ic), (Ia'), (Ib'), (Ic'), (IIa), (IIb), (IIc), (IIIa), (IIIb), (IIIc), (IVa), (IVb), and (IVc)), or a pharmaceutically acceptable salt thereof.

The present disclosure contemplates the administration of the compounds described herein, and compositions (e.g., pharmaceutical salts, pharmaceutical composition) thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the compounds disclosed herein over a defined period of time. In embodiments, the administration is oral administration. In embodiments, the administration is parenteral administration.

The compounds of the present disclosure may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or $ED_{50}$ of an agent is the dose or amount of an agent that produces a therapeutic response or desired effect in 50% of the population to which it is administered. Although the $ED_{50}$ is commonly used as a measure of reasonable expectance of an agent's effect, it is not necessarily the dose that a clinician might deem appropriate taking into consideration all relevant factors. Thus, in some situations the effective amount is more than the calculated $ED_{50}$, in other situations the effective amount is less than the calculated $ED_{50}$, and in still other situations the effective amount is the same as the calculated $ED_{50}$.

In addition, an effective dose of the compounds of the present disclosure may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In embodiments, the compounds contemplated by the present disclosure may be administered (e.g., orally) at dosage levels of about 0.01 mg/kg to about 50 mg/kg, or about 1 mg/kg to about 25 mg/kg, of subject body weight per day, one, two, three, four or more times a day, to obtain the desired therapeutic effect. For administration of an oral agent, the compositions can be provided in the form of tablets, capsules and the like containing from 0.05 to 1000 milligrams of the active ingredient, particularly 0.05, 0.1, 0.25, 0.5, 0.75, 1.0, 1.25, 1.5, 1.75, 2.0, 2.5, 5.0, 7.5, 10.0, 15.0, 20.0, 25.0, 50.0, 75.0, 100.0, 125.0, 150.0, 175.0, 200.0, 250.0, 300.0, 400.0, 500.0, 600.0, 750.0, 800.0, 900.0, and 1000.0 milligrams of the active ingredient. A pharmaceutically acceptable carrier(s), diluent(s) and/or excipient(s) may be present in an amount of from about 0.1 g to about 2.0 g.

In embodiments, the dosage of the desired compound is contained in a "unit dosage form". The phrase "unit dosage form" refers to physically discrete units, each unit including a predetermined amount of a compound (e.g., a compound described herein), sufficient to produce the desired effect. It will be appreciated that the parameters of a unit dosage form will depend on the particular agent and the effect to be achieved.

V. KITS

In another aspect, provided herein is a kit including a compound described herein or pharmaceutical compositions thereof. The kits are generally in the form of a physical structure housing various components, as described below, and may be utilized, for example, in practicing the methods described above.

A kit may include one or more of the compounds disclosed herein (e.g., provided in a sterile container), which may be in the form of a pharmaceutical composition suitable for administration to a subject. In embodiments, the compound has the structure of Formulae (Ia), (Ib), (Ic), (Ia'), (Ib'), (Ic'), (IIa), (IIb), (IIc), (IIIa), (IIIb), (IIIc), (IVa), (IVb), and (IVc)), or a pharmaceutically acceptable salt thereof. The compounds described herein can be provided in a form that is ready for use (e.g., a tablet or capsule) or in a form requiring, for example, reconstitution or dilution (e.g., a powder) prior to administration. When the compound is in a form that needs to be reconstituted or diluted by a user, the kit may also include diluents (e.g., sterile water), buffers, pharmaceutically acceptable excipients, and the like, packaged with, or separately from, the compound. Each component of the kit may be enclosed within an individual container, and all of the various containers may be within a single package. A kit of the present disclosure may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EMBODIMENTS

Embodiment 1. A compound of formula (Ia) or (Ib):

(Ia)

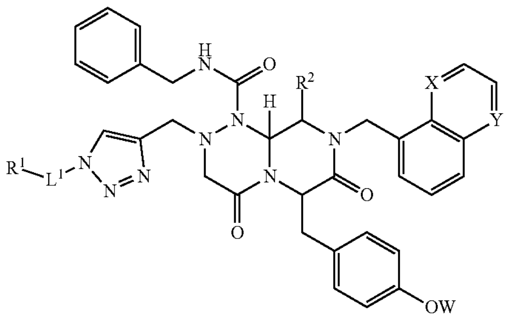

or (Ib)

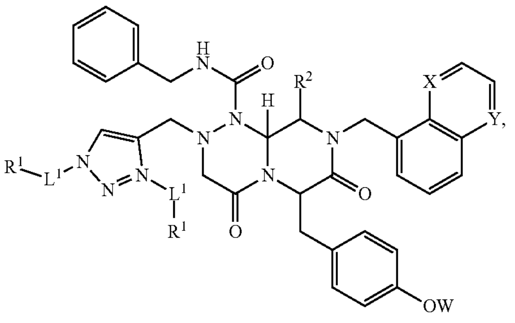

or (Ic)

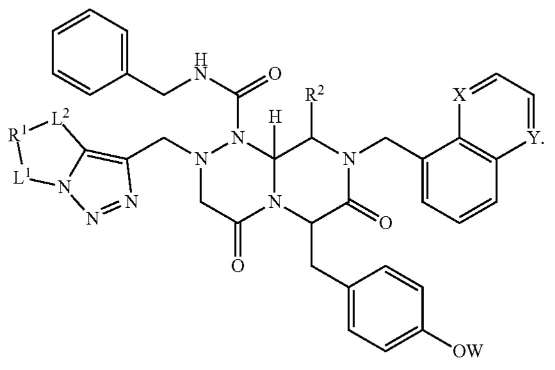

or a pharmaceutically acceptable salt thereof, wherein:

X is N or —CH;

Y is N or —CH;

$L^1$ or $L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;

$R^1$ is independently hydrogen, halogen, $—CX^1_3$, $—CHX^1_2$, $—CH_2X^1$, $—OCX^1_3$, $—OCHX^1_2$, $—OCH_2X^1$, —CN, $—S(O)_2R^{1A}$, $—SR^{1A}$, $—S(O)R^{1A}$, $—SO_2NR^{1A}R^{1B}$, $—NHC(O)NR^{1A}R^{1B}$, $—N(O)_2$, $—NR^{1A}R^{1B}$, $—NHNR^{1A}R^{1B}$, $—C(O)R^{1A}$, $—C(O)—OR^{1A}$, $—C(O)—NR^{1A}R^{1B}$, $—C(O)NHNR^{1A}R^{1B}$, $—OR^{1A}$, $—NR^{1A}SO_2R^{1B}$, $—NR^{1A}C(O)R^{1B}$, $—NR^{1A}C(O)OR^{1B}$, 13 $NR^{1A}OR^{1B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen or substituted or unsubstituted $C_1$-$C_4$ alkyl;

$R^{1A}$ and $R^{1B}$ are independently hydrogen, $—CX^1_3$, $—CHX^1_2$, $—CH_2X^1$, —C(O)OH, $—C(O)NH_2$, —OH, $—NH_2$, —COOH, $—CONH_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)OH, —NHOH, $—OCX^1_3$, $—OCHX^1_2$, $—OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{1A}$ and $R^{1B}$ substituents bonded to the same nitrogen atom may optionally be joined to form a substituted or unsubstituted heterocycloalkyl or substituted or unsubstituted heteroaryl;

$X^1$ is independently halogen; and wherein W is hydrogen, phosphate or phosphate salt, or an ester of an alkyl acid or of a fatty acid, preferably hydrogen.

Embodiment 2. The compound of embodiment 1, wherein the compound is of the formula (Ia'), (Ib') or (Ic'):

(Ia')

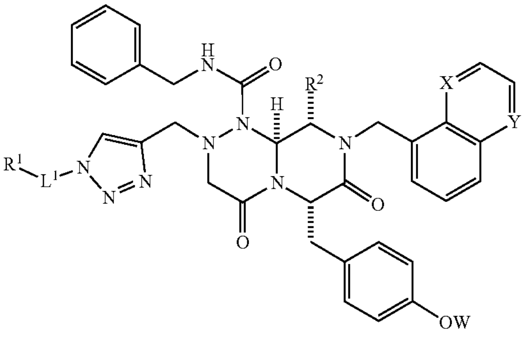

or

-continued (Ib')

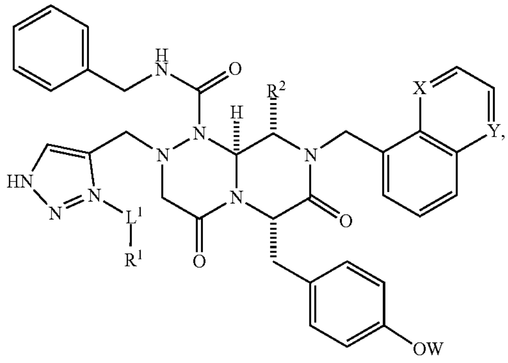

, or (Ic')

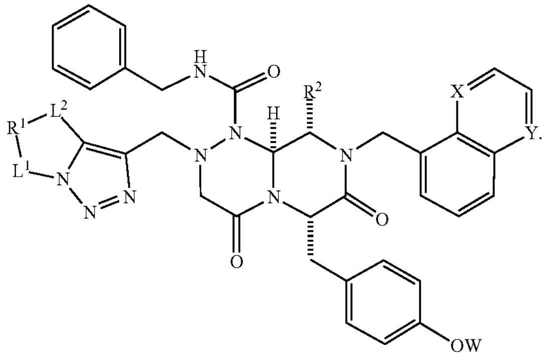

.

or a pharmaceutically acceptable salt thereof.

Embodiment 3. The compound of embodiment 1 or 2, wherein the compound is of the formula (IIa) or (IIb):

(IIa)

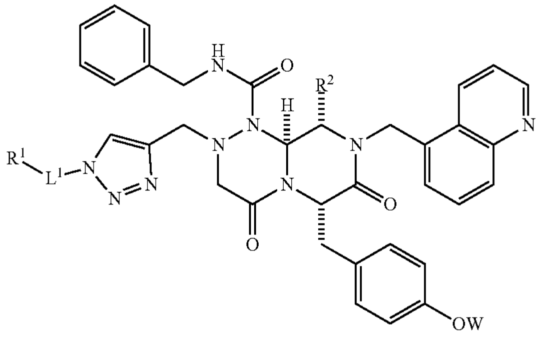

or

-continued
(IIb)
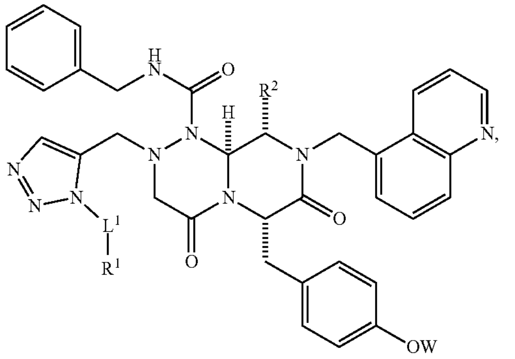
or
(IIc)
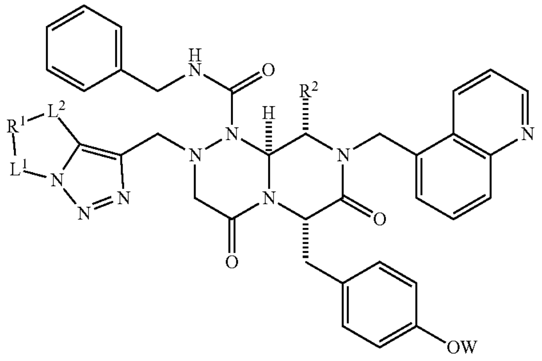
or a pharmaceutically acceptable salt thereof.
Embodiment 4. The compound of embodiment 1 or 2, wherein the compound is of the formula (IIIa), (IIIb) or (IIIc):
(IIIa)
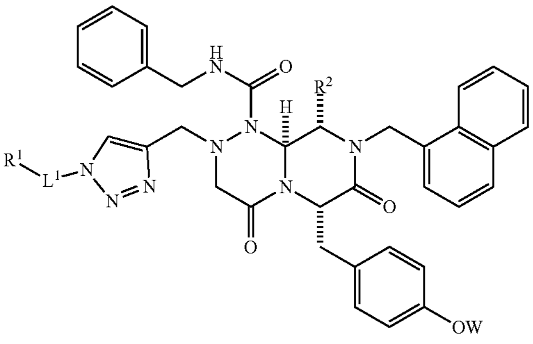
or
-continued
(IIIb)
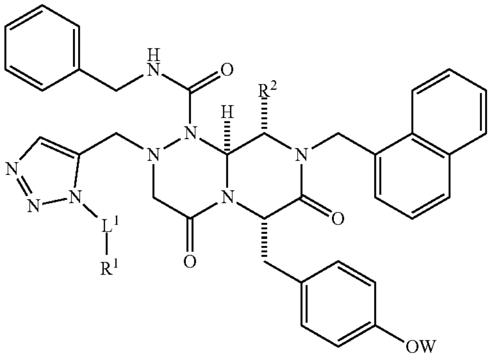
,
(IIIc)
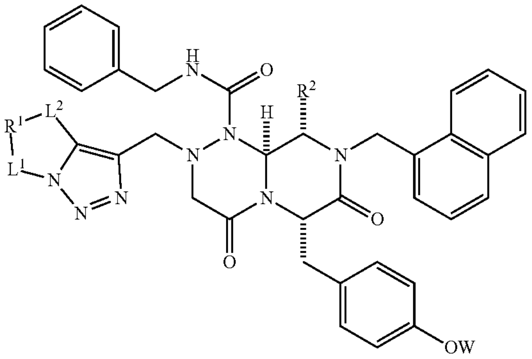
or a pharmaceutically acceptable salt thereof.
Embodiment 5. The compound of embodiment 1 or 2, wherein the compound is of the formula (IVa), (IVb), or (IVc):
(IVa)
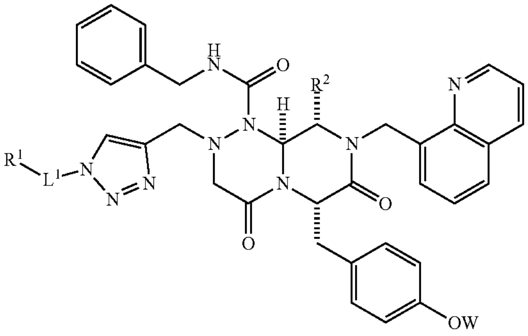
or
(IVb)
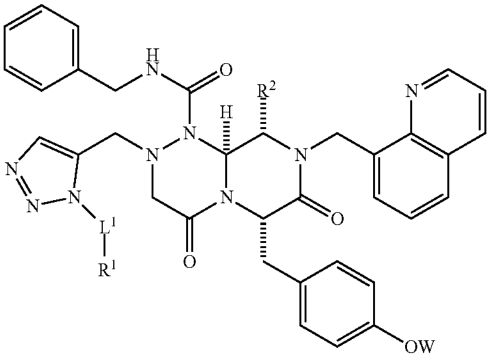
, -continued (IVc)

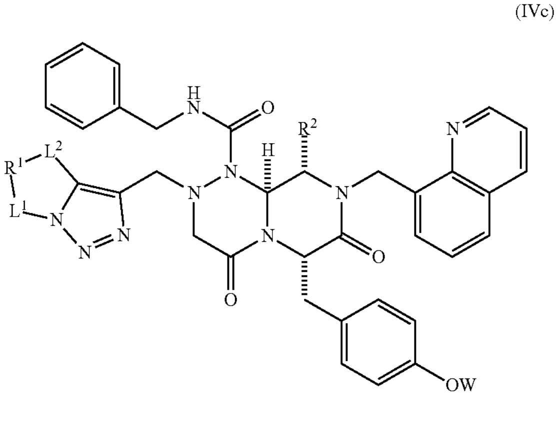

or a pharmaceutically acceptable salt thereof.

Embodiment 6. The compound of any one of embodiments 1 to 5, wherein $L^1$ or $L^2$ is $(CH_2)n$, and n is an integer from 0 to 4.

Embodiment 7. The compound of any one of embodiments 1 to 6, wherein $R^2$ is hydrogen, $—CH_3$, or $—CH_2CH_3$.

Embodiment 8. The compound of any one of embodiments 1 to 7, wherein $L^1$ or $L^2$ is methylene or ethylene.

Embodiment 9. The compound of any one of embodiments 1 to 8, wherein $R^1$ is halogen, $—CX^1_3$, $—CHX^1_2$, $—CH_2X^1$, $—OCX^1_3$, $—OCHX^1_2$, $—OCH_2X^1$, —CN, $—S(O)_2R^{1A}$, $—SR^{1A}$, $—S(O)R^{1A}$, $—SO_2NR^{1A}R^{1B}$, $—NHC(O)NR^{1A}R^{1B}$, $—N(O)_2$, $—NR^{1A}R^{1B}$, $—NHNR^{1A}R^{1B}$, $—C(O)R^{1A}$, $—C(O)—OR^{1A}$, $—C(O)NR^{1A}R^{1B}$, $—C(O)NHNR^{1A}R^{1B}$, $—OR^{1A}SO_2R^{1B}$, $—NR^{1A}C(O)R^{1B}$, $—NR^{1A}C(O)OR^{1B}$, $—NR^{1A}OR^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl Embodiment 10. The compound of embodiment 9, wherein $R^1$ is —CN, —OH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 11. The compound of embodiment 1, wherein the compound is:

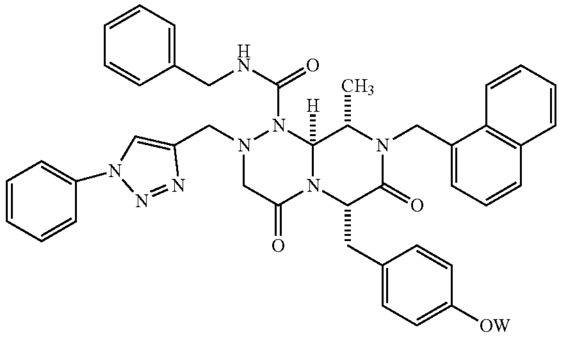

,

-continued

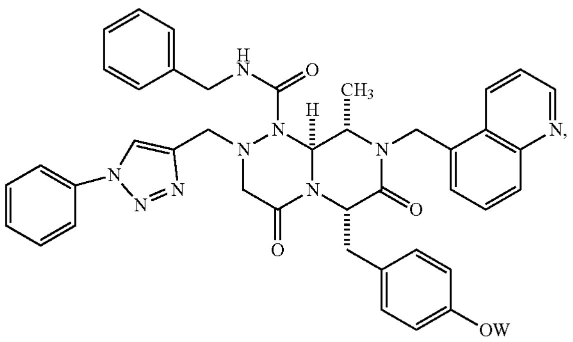

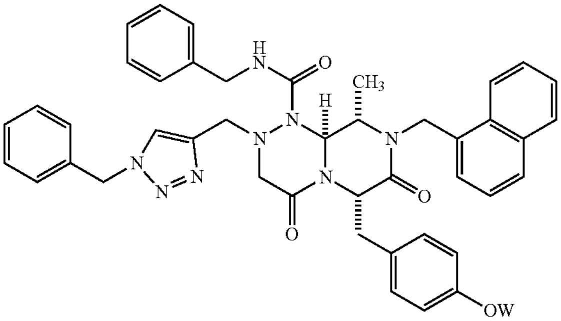

,

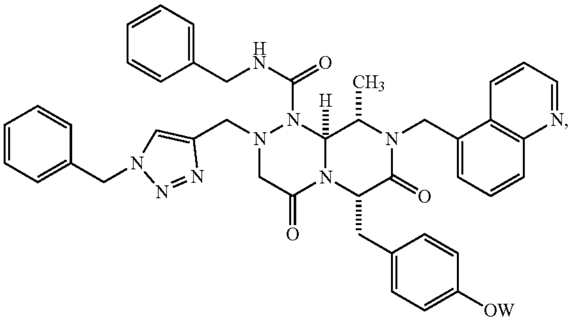

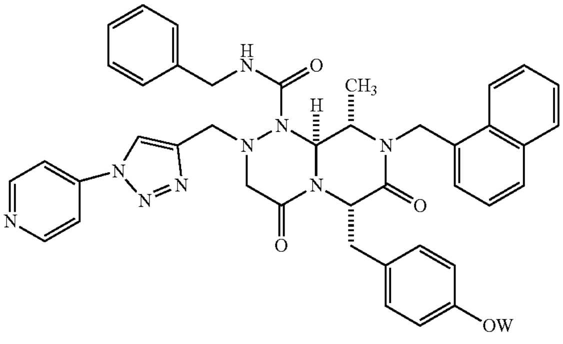

,

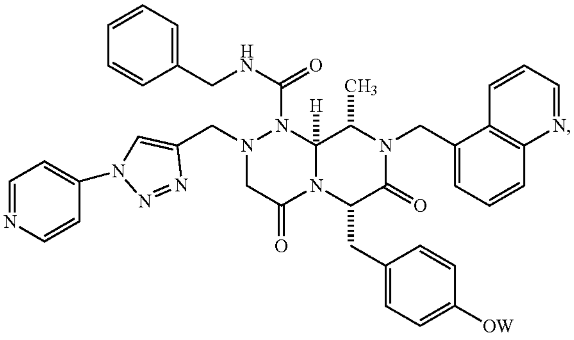

-continued
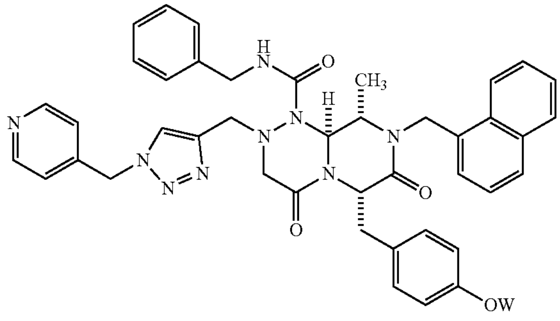
,
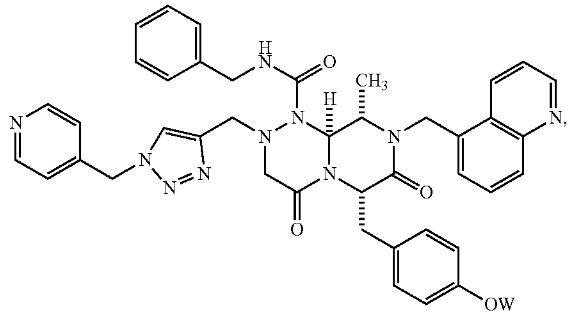
,
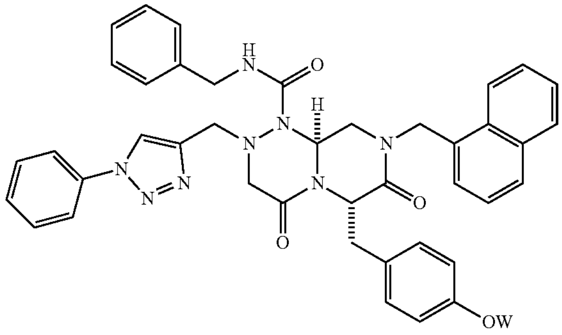
,
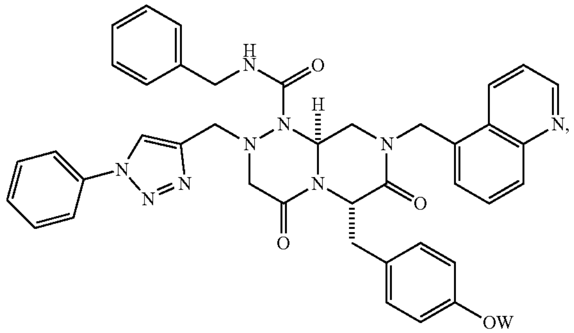
,
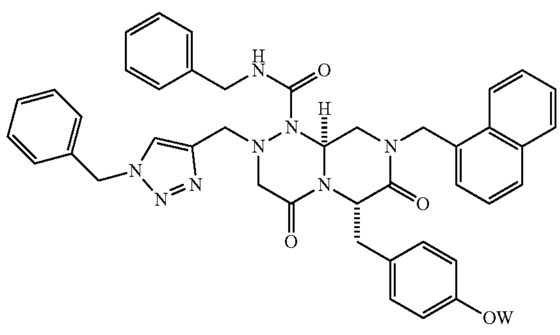
,
-continued
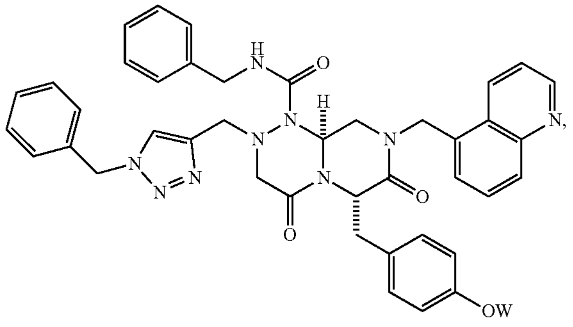
,
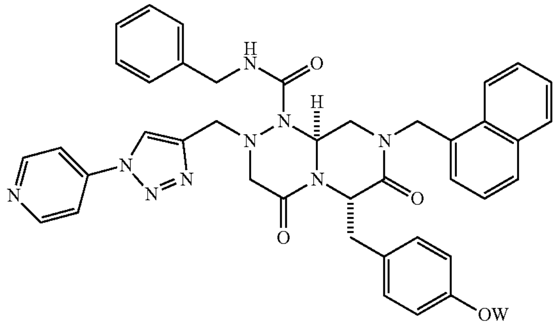
,
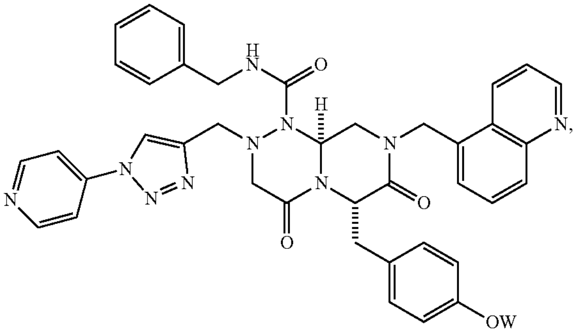
,
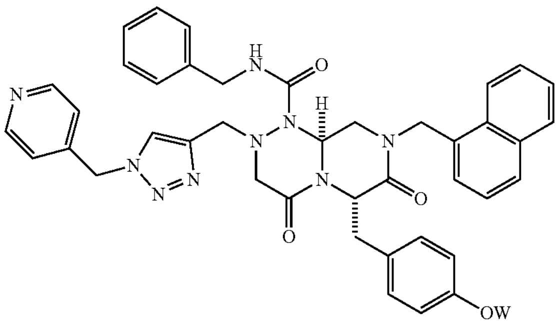
,
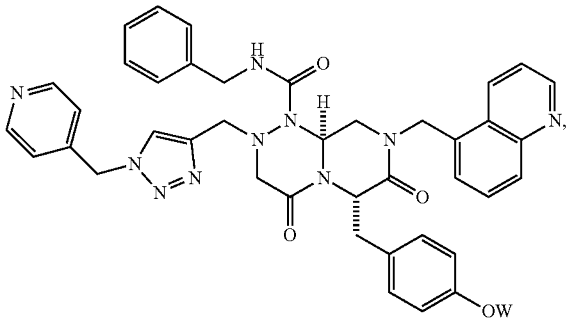
, -continued
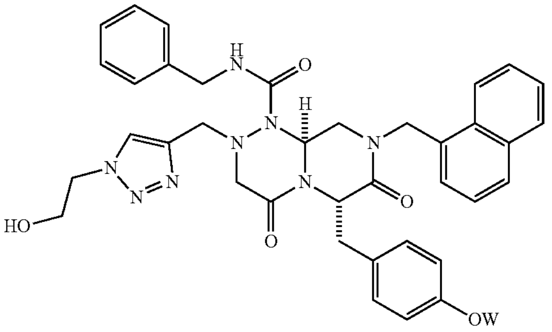
,
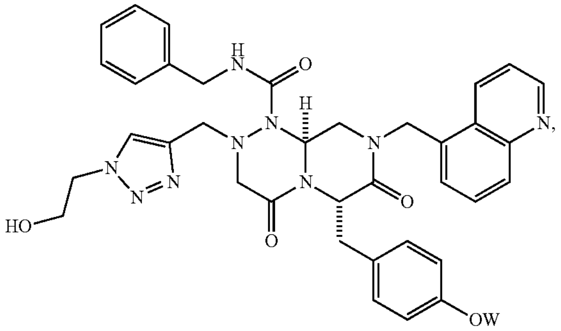
,
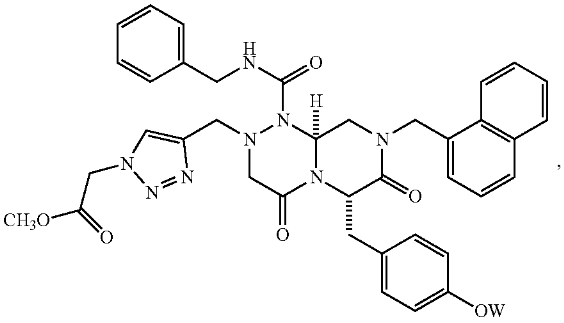
,
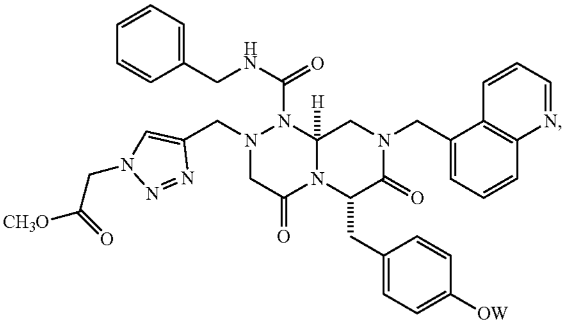
,
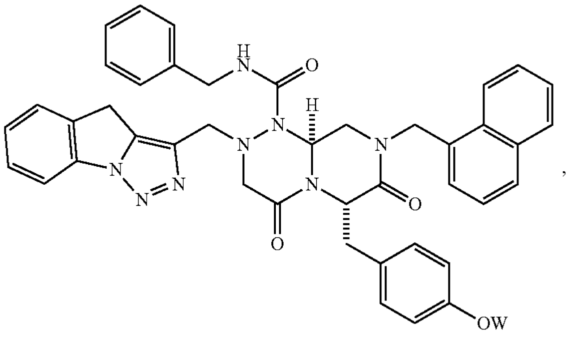
,
-continued
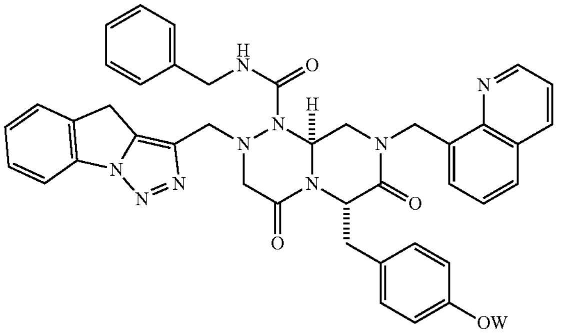
,
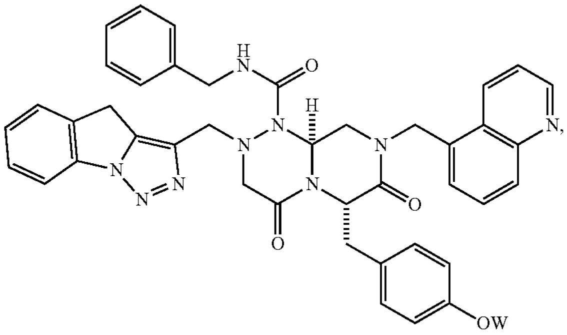
,
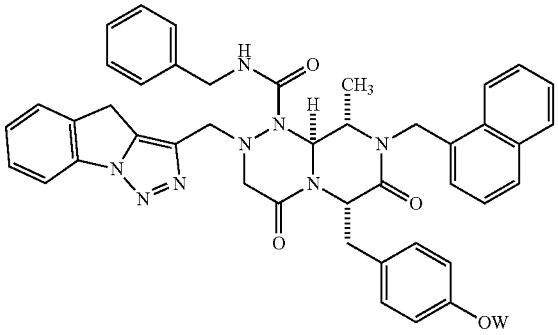
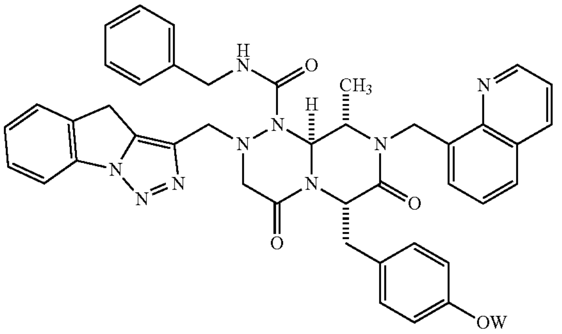
,
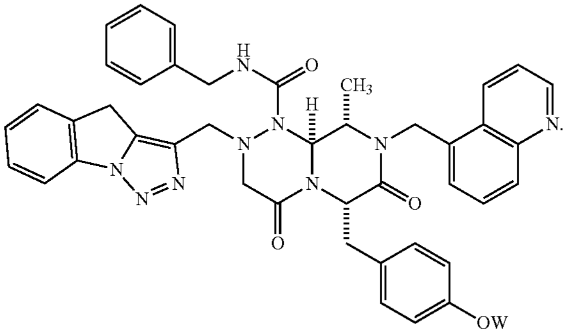
.

Embodiment 12. The compound of any one of embodiments 1 to 11, wherein the ester of the alkyl acid or of the fatty acid is selected from:

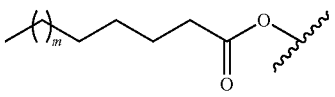

wherein m is 1 to 14,

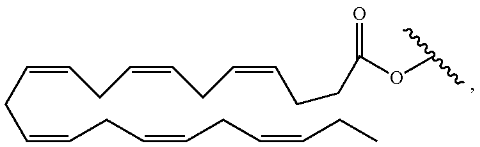

, or

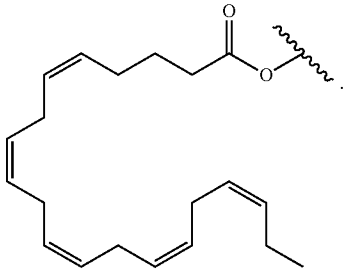

.

Embodiment 13. A pharmaceutical composition comprising the compound of any one of embodiments 1 to 12, and a pharmaceutically acceptable carrier.

Embodiment 14. A method of treating a disease or disorder associated with modulation of CREB binding protein (CBP)/catenin signaling pathway, said method comprises administering to a patient or a warm blooded mammal in need thereof a therapeutically effective amount of the compound of any one of embodiments 1 to 11.

Embodiment 15. The method of embodiment 13, wherein the disease or disorder associated with modulation of the CBP/catenin signaling pathway is cancer, fibrosis, diabetes, or neurodevelopmental or neurodegenerative diseases.

Embodiment 16. The method of embodiment 14 for use in treating cancer, fibrosis, diabetes, or neurodevelopmental or neurodegenerative diseases.

Embodiment 17. The method of embodiment 15, wherein the fibrosis is fibrosis of the lung, liver, kidney, heart or systemic fibrosis.

Embodiment 18. A cosmetic method for treating a skin condition, comprising transdermally or topically administering to a patient or a warm-blooded mammal, having a skin condition, a cosmeceutically effective amount of the compound of any one of embodiments 1-11, wherein W is an ester of an alkyl acid or of a fatty acid, preferably wherein the ester of the alkyl acid or of the fatty acid is selected from:

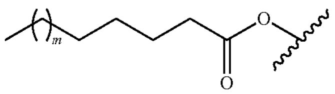

wherein m is 1 to 14,

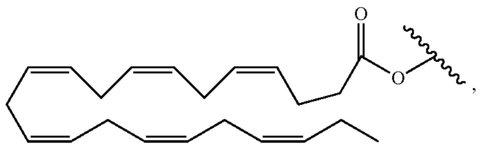

, or

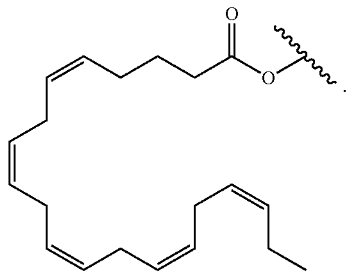

.

Embodiment 19. The method of embodiment 18, wherein the skin condition comprises one or more aging skin conditions selected from wrinkles, hyperpigmentation, redness, rosacea, dryness, cracking, loss of vibrance, loss of elasticity, thinning, loss of vibrance, scarring, acne, sun damage, hair loss, loss of hair coloration, reduced cuticle growth, and/or reduced nail growth.

EXAMPLES

Identification of Wnt/Catenin Signaling Pathway/CBP/Catenin Signaling Pathway Modulators In embodiments, compounds described herein possess at least one property or characteristic that is of therapeutic relevance. Candidate inhibitors may be identified by using, for example, an art-accepted assay or model. The Example section described assay(s) that were used to determine the Wnt/catenin signaling pathway/CBP/catenin signaling pathway modulatory activity of the compounds described herein, as well as assays that could be used to evaluate one or more characteristics of the compounds; the skilled artisan is aware of other procedures, assay formats, and the like that can be employed to generate data and information useful to assess the Wnt/catenin signaling pathway/CBP/catenin signaling pathway modulators described herein.

After identification, candidate inhibitors can be further evaluated by using techniques that provide data regarding characteristics of the modulators (e.g., pharmacokinetic parameters). Comparisons of the candidate modulators to a reference standard (which may the "best-of-class" of current modulators) are indicative of the potential viability of such candidates. Wnt/catenin signaling pathway/CBP/catenin signaling pathway modulators that can serve as reference or benchmark compounds include those shown to demonstrate desired activity and characteristics useful for analyzing candidate modulators which will be apparent to the skilled artisan.

Chemical Synthesis

Example 1

Synthesis of methyl 2-(4-(((6S,9aS)-1-(benzylcarbamoyl)-6-(4-hydroxybenzyl)-4,7-dioxo-8-(quinolin-8-ylmethyl)octahydro-2H-pyrazino[2,1-c][1,2,4]triazin-2-yl)methyl)-1H-1,2,3-triazol-1-yl)acetate (2)

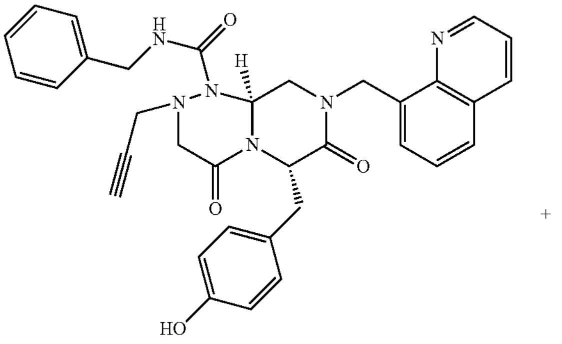

+

1

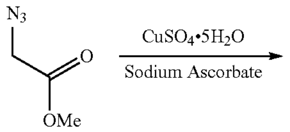

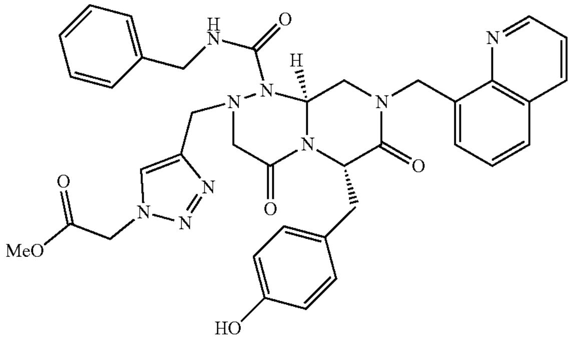

2

To a solution of 1 (30 mg, 0.05 mmol, 1 equiv) and azide (12 mg, 0.1 mmol, 2 equiv) in MeOH (1.0 mL) and $H_2O$ (0.5 mL) was added copper sulfate pentahydrate (1.3 mg, 0.005 mmol, 0.1 equiv) and sodium ascorbate (20 mg, 0.1 mmol). The reaction was stirred overnight. The reaction was diluted with $CH_2Cl_2$ and washed with $H_2O$ and brine. The crude residue was purified by chromatography to provide the product 2 (21 mg, 0.03 mmol, 60% yield). $^1H$ NMR (400 MHz, $CDCl_3$) δ (ppm): 8.86 (dd, 1H, J=2.0 Hz, 4.4 Hz), 8.14 (dd, 1H, J=2.0 Hz, 8.4 Hz), 7.75 (d, 1H, J=8.0 Hz), 7.61 (d, 1H, J=6.4 Hz), 7.50-7.58 (m, 1H), 7.39 (dd, 1H, J=4.4 Hz, 8.4 Hz), 7.20-7.35 (m, 5H), 7.10 (t, 1H, J=6.4 Hz), 6.92 (d, 2H, J=8.4 Hz), 6.56 (d, 2H, J=8.4 Hz), 5.46-5.53 (m, 1H), 5.36 (d, 1H, J=14.8 Hz), 5.30-5.34 (m, 1H), 5.20 (d, 1H, J=14.8 Hz), 5.03 (s, 2H), 4.36 (dd, 1H, J=6.4 Hz, 15.2 Hz), 4.24 (dd, 1H, J=6.0 Hz, 15.2 Hz), 4.12 (s, 2H), 3.80 (d, 2H, J=14.0 Hz), 3.77 (s, 3H), 3.64 (dd, 1H, J=4.4 Hz, 11.6 Hz), 3.50 (d, 1H, J=16.4 Hz), 3.28-3.38 (m, 2H); 13C NMR (75 MHz, $CDCl_3$) δ (ppm): 166.5, 166.4, 162.5, 156.0, 155.5, 149.7, 146.6, 142.5, 139.0, 136.4, 134.0, 130.6, 129.4, 128.6, 128.3, 127.8, 127.6, 127.5, 127.3, 126.6, 123.9, 121.2, 115.8, 60.6, 57.0, 53.2, 53.1, 52.2, 52.1, 50.6, 47.2, 44.1, 35.7; MS $C_{37}H_{37}N_9O_6$ $[M+H]^+$ calc'd: 703.29, found: 703.36.

Example 2

Synthesis of (6S,9aS)-2-((8H-[1,2,3]triazolo[5,1-a]isoindol-3-yl)methyl)-N-benzyl-6-(4-hydroxybenzyl)-8-(naphthalen-1-ylmethyl)-4,7-dioxohexahydro-2H-pyrazino[2,1-c][1,2,4]triazine-1(6H)-carboxamide (5)

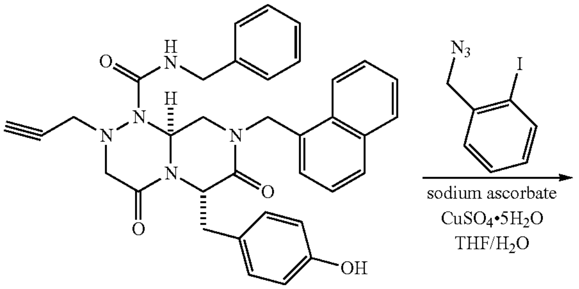

3

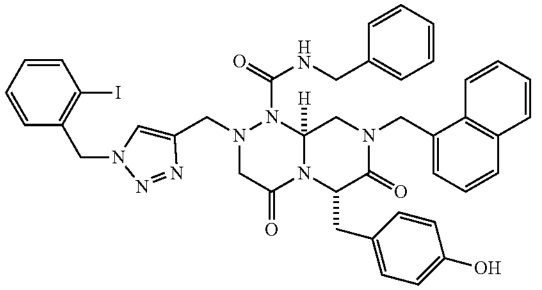

+

4

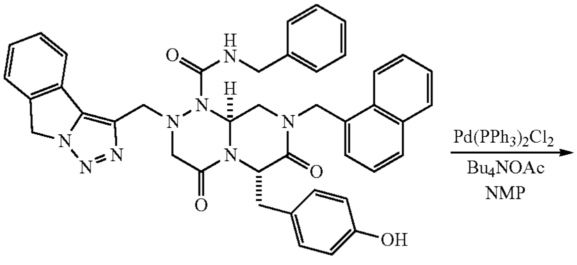

5

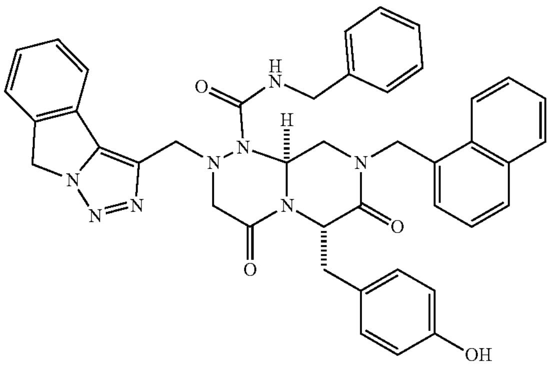

5

Step 1. To a stirred solution of alkyne 3 (120 mg, 0.2 mmol) in 4 mL THF were added 2-iodobenzyl azide (100 mg, 0.4 mmol), copper sulfate pentahydrate (2.5 mg, 0.01 mmol) in 1 mL $H_2O$ and Sodium Ascorbic acid (80 mg, 0.4 mmol). The reaction was stirred at rt overnight and THF was removed. The residue was extracted with DCM. The organic layer were dried and evaporated. The short chromatograph with 1-2% $MeOH/CH_2Cl_2$ gave a 130 mg mixture of 4 and 5 (9:1 ratio).

Step 2. To a stirred solution of a mixture 4 and 5 (9:1 ratio, 130 mg, 0.15 mmol) from Step 1 above in 1.2 mL NMP was added $Pd(PPh_3)_2Cl_2$ (5 mg, 0.0075 mmol) and $Bu_4NOAc$ (90 mg, 0.3 mmol) under $N_2$. The mixture was heated to 100° C. for 18 h. After cooling down, the reaction was diluted with EtOAc and washed with H2O (5×). The chromatograph with 1-2% $MeOH/CH_2Cl_2$ gave the product 5 (90 mg, 0.12 mmol, 60% yield for two steps). $^1H$ NMR (400 MHz, $CDCl_3$) δ (ppm): 8.11 (d, 1H, J=8.8 Hz), 7.84 (d, 1H, J=8.4 Hz), 7.79 (d, 1H, J=8.4 Hz), 7.54-7.58 (m, 1H), 7.46-7.51 (m, 2H), 7.32-7.42 (m, 4H), 7.18-7.28 (m, 4H), 7.08 (d, 2H, J=6.4 Hz), 7.02-7.08 (b, 1H), 7.01 (d, 2H, J=8.4 Hz), 6.60 (d, 2H, J=8.4 Hz), 5.51 (dd, 1H, J=4.0 Hz, 10.4 Hz), 5.44 (t, 1H, J=5.6 Hz), 5.08-5.25 (m, 4H), 4.16-4.28 (m, 3H), 4.07 (d, 1H, J=14.8 Hz), 3.61 (t, 1H, J=10.4 Hz), 3.28-3.48 (m, 5H); 13C NMR (75 MHz, $CDCl_3$) δ (ppm): 166.1, 162.5, 156.0, 155.7, 140.9, 138.8, 133.9, 132.6, 131.5, 130.75, 130.65, 129.1, 128.94, 128.87, 128.80, 128.5, 127.4, 127.3, 127.1, 126.8, 126.7, 126.1, 125.3, 124.5, 123.6, 120.8, 115.8, 60.5, 57.0, 53.2, 52.4, 51.2, 50.5, 48.1, 44.0, 35.7; MS $C_{42}H_{38}N_8O_4$ $[M+H]^+$ calc'd: 719.3; found: 719.3

Example 3

Synthesis of 4-(((6S,9aS)-1-(benzylcarbamoyl)-4,7-dioxo-2-((1-phenyl-1H-1,2,3-triazol-4-yl)methyl)-8-(quinolin-5-ylmethyl)octahydro-1H-pyrazino[2,1-c][1,2,4]triazin-6-yl)methyl)phenyl dodecanoate

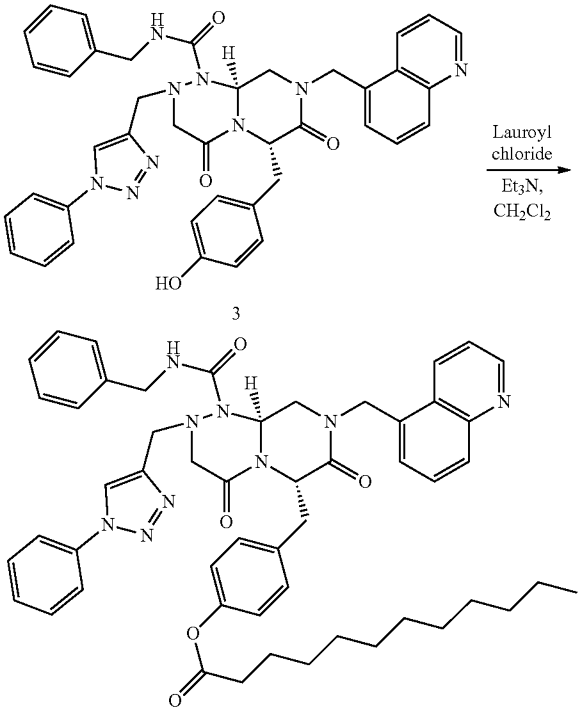

3

4

To a solution of 3 (118 mg, 0.167 mmol) in dry $CH_2Cl_2$ at 0° C. was added $Et_3N$ (0.047 mL, 0.334 mmol), followed by slow addition of lauroyl chloride (0.058 mL, 0.251 mmol). The reaction mixture was stirred under argon at 0° C. for 1 hour and at room temperature overnight, and evaporated to dryness. The resulting residues were taken into EtOAc and sat'd $NaHCO_3$ (aq.), and the organic layers were washed with sat'd NaCl and dried ($MgSO_4$). Evaporation, purification by silica-gel chromatography and lyophilization gave the title product 4 as a foam. MS (ESI): m/z 890.5 $(M+H)^+$.

Biological Assays

Wnt-Driven Luciferase Activity in Stably Transfected Cell Line Assay (STF1.1 Assay)

Hek-293 (human embryonic kidney 293), STF1.1 cells were maintained in DMEM, 10% FBS, Pen-Strep supplemented with 200 μg/mL G418. One day prior to assay, cells were split into a white, opaque 96-well plate at 10,000 cells per well in 50 microliters of complete medium without G418. After allowing the cells to stabilize and attach overnight, 40 microliters of complete medium (without G418) containing 2.5× final concentration of compound or DMSO control was added to the cells and allowed to incubate for 1 hour at 37° C., 5% CO2 prior to adding 10 microliters of a 100 mM LiCl solution prepared in complete medium (without G418). After 24 hours, 100 microliters of BrightGlo (Promega, Cat. #: G7573) was added to each well and the plate was shaken for 5 minutes prior to reading on the Perkin-Elmer EnVision Plate Reader.

Human Survivin 1 Kb-Promoter-Driven Luciferase Activity in Stably Transfected Cell Line Assay (1 Kb Hu-Survivin\luc-Hek293 Assay)

1 Kb Hu-survivin\luc-Hek293 cells were maintained in DMEM, 10% FBS, Pen-Strep supplemented with 1 μg/mL of puromycin. One day prior to assay, cells were split into a white, opaque 96-well plate at 10,000 cells per well in 50 microliters of complete medium without puromycin. After allowing the cells to stabilize and attach overnight, 50 microliters of complete medium (without G418) containing 2× final concentration of compound or DMSO control was added to the cells. After 24 hours, 100 microliters of BrightGlo (Promega, Cat. #: G7573) was added to each well and the plate was shaken for 5 minutes prior to reading on the Perkin-Elmer EnVision Plate Reader.

The results are shown in FIGS. 1 and 2. Compound μM9 is an example of a specific Wnt/CBP/Catenin antagonist with a similar profile to the positive control ICG-001.

It is understood that the examples described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound of formula (Ia) or formula (Ic):

(Ia)

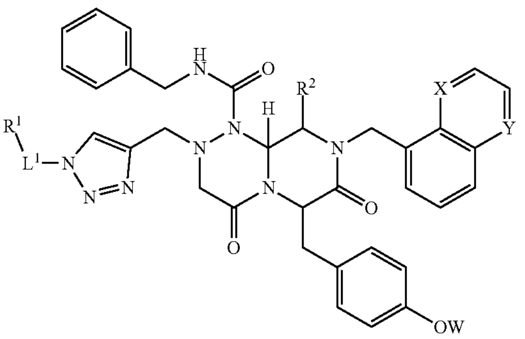

or (Ic)

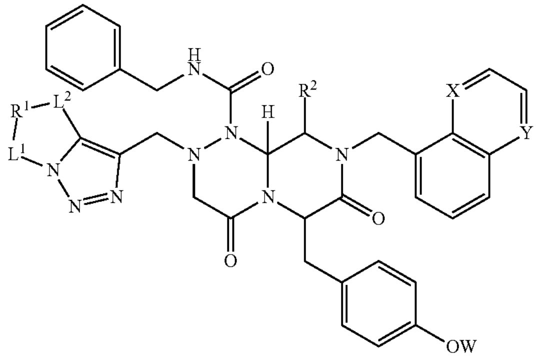

or a pharmaceutically acceptable salt or stereoisomer thereof, wherein:

$L^1$ is a bond, alkylene, heteroalkylene, cycloalkylene, heterocycloalkylene, arylene, or heteroarylene;

$R^1$ is H, halogen, CN, $NO_2$, alkyl, heteroalkyl, $CH_2X^1$, $CH(X^1)_2$, $C(X^1)_3$, $C(O)R^{1A}$, $C(O)OR^{1A}$, $C(O)NR^{1A}R^{1B}$, $C(O)NHNR^{1A}R^{1B}$, $NR^{1A}R^{1B}$, $NR^{1A}C(O)R^{1B}$, $NR^{1A}C(O)OR^{1B}$, $NR^{1A}OR^{1B}$, $NR^{1A}S(O)_2R^{1B}$, $NHC(O)NR^{1A}R^{1B}$, $NHNR^{1A}R^{1B}$, $N_3$, $OCH_2X^1$, $OCH(X^1)_2$, $OC(X^1)_3$, $OR^{1A}$, $SR^{1A}$, $S(O)R^{1A}$, $S(O)_2R^{1A}$, $S(O)_2NR^{1A}R^{1B}$, cycloalkyl, heterocycloalkyl, aryl, or heteroaryl;

$R^{1A}$ is H, alkyl, heteroalkyl, $CH_2X^1$, $CH(X^1)_2$, $C(X^1)_3$, $C(O)OH$, $C(O)NH_2$, $NH_2$, $NHC(O)H$, $NHC(O)OH$, $NHOH$, $NHC(O)NH_2$, $NHC(O)NHNH_2$, $NHNH_2$, $NHS(O)_2H$, OH, $OCH_2X^1$, $OCH(X^1)_2$, $OC(X^1)_3$, $ONH_2$, $OS(O)_2OH$, SH, $S(O)_2NH_2$, $S(O)_2OH$, cycloalkyl, heterocycloalkyl, aryl, or heteroaryl;

$R^{1B}$ is H, alkyl, heteroalkyl, $CH_2X^1$, $CH(X^1)_2$, $C(X^1)_3$, $C(O)OH$, $C(O)NH_2$, $NH_2$, $NHC(O)H$, $NHC(O)OH$, $NHOH$, $NHC(O)NH_2$, $NHC(O)NHNH_2$, $NHNH_2$, $NHS(O)_2H$, OH, $OCH_2X^1$, $OCH(X^1)_2$, $OC(X^1)_3$, $ONH_2$, $OS(O)_2OH$, SH, $S(O)_2NH_2$, $S(O)_2OH$, cycloalkyl, heterocycloalkyl, aryl, or heteroaryl; or $R^{1A}$ and $R^{1B}$, together with the nitrogen atom to which they are bonded, form a heterocycloalkyl or heteroaryl;

each $X^1$ is independently halogen

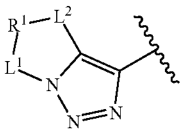

is

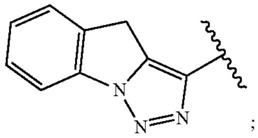

;

$R^2$ is H or $C_1$-$C_4$ alkyl;

W is H, phosphate, a phosphate salt, an ester of an alkyl acid, or an ester of a fatty acid;

X is CH or N; and

Y is CH or N.

2. The compound of claim 1, or a stereoisomer thereof, wherein the stereoisomer of the compound is of formula (Ia') or formula (Ic'):

(Ia')

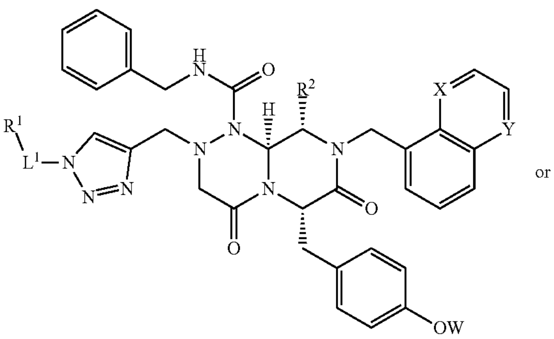

or (Ic')

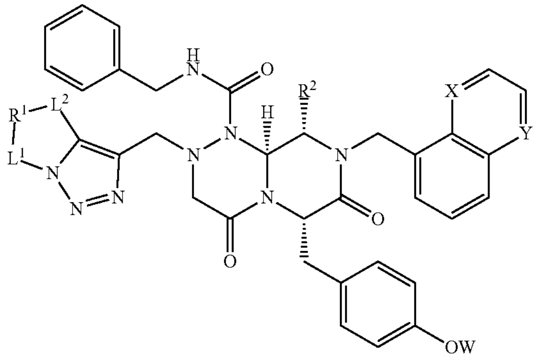

or a pharmaceutically acceptable salt thereof.

3. The compound of claim 1, or a stereoisomer thereof, wherein the stereoisomer of the compound is of formula (IIa) or formula (IIc):

(IIa)

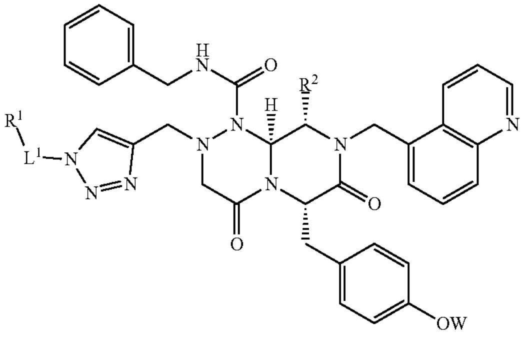

or (IIc)

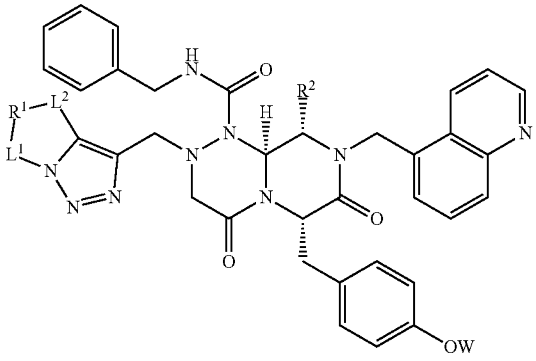

or a pharmaceutically acceptable salt thereof.

4. The compound of claim 1, or a stereoisomer thereof, wherein the stereoisomer of the compound is of formula (IIIa) or formula (IIIc):

(IIIa)

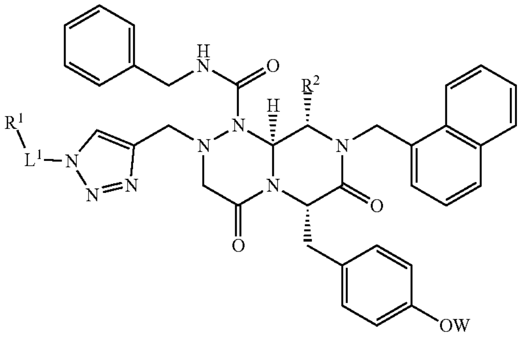

or

-continued (IIIc)

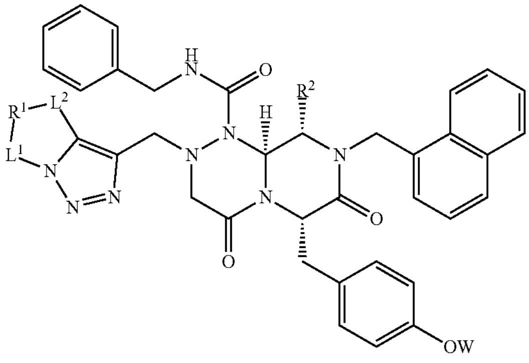

or a pharmaceutically acceptable salt thereof.

5. The compound of claim 1, or a stereoisomer thereof, wherein the stereoisomer of the compound is of formula (IVa) or formula (IVc):

(IVa)

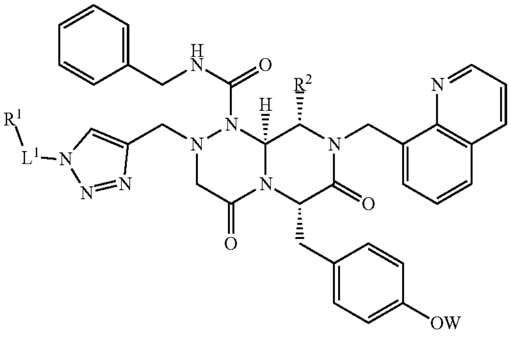

or (IVc)

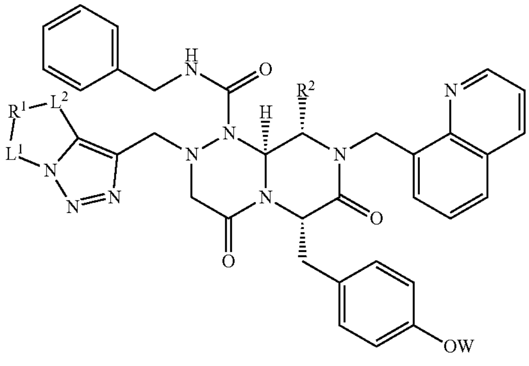

or a pharmaceutically acceptable salt thereof.

6. The compound of claim 1, or a pharmaceutically acceptable salt or stereoisomer thereof, wherein:

$L^1$ is a bond or $-(CH_2)_n-$; and n is 1, 2, 3, or 4.

7. The compound of claim 1, or a pharmaceutically acceptable salt or stereoisomer thereof, wherein $R^1$ is halogen, CN, $NO_2$, alkyl, heteroalkyl, $CH_2X^1$, $CH(X^1)_2$, $C(X^1)_3$, $C(O)R^{1A}$, $C(O)OR^{1A}$, $C(O)NR^{1A}R^{1B}$, $C(O)NHNR^{1A}R^{1B}$, $NR^{1A}R^{1B}$, $NR^{1A}C(O)R^{1B}$, $NR^{1A}C(O)OR^{1B}$, $NR^{1A}OR^{1B}$, $NR^{1A}S(O)_2R^{1B}$, $NHC(O)NR^{1A}R^{1B}$, $NHNR^{1A}R^{1B}$, $OCH_2X^1$, $OCH(X^1)_2$, $OC(X^1)_3$, $OR^{1A}$, $SR^{1A}$, $S(O)R^{1A}$, $S(O)_2R^{1A}$, $S(O)_2NR^{1A}R^{1B}$, cycloalkyl, heterocycloalkyl, aryl, or heteroaryl.

8. The compound of claim 7, or a pharmaceutically acceptable salt or stereoisomer thereof, wherein $R^1$ is CN, alkyl, heteroalkyl, OH, cycloalkyl, heterocycloalkyl, aryl, or heteroaryl.

9. The compound of claim 1, or a pharmaceutically acceptable salt or stereoisomer thereof, wherein $R^2$ is H, $CH_3$, or $CH_2CH_3$.

10. The compound of claim 1, or a pharmaceutically acceptable salt or stereoisomer thereof, wherein W is:

wherein m is 1, 2, 3, 4, 5, 6, 7, 8, 9, 10, 11, 12, 13, or 14;

(a)

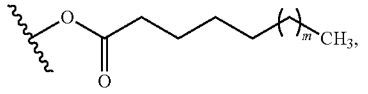

(b)

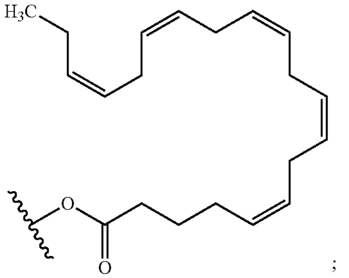

; or (c)

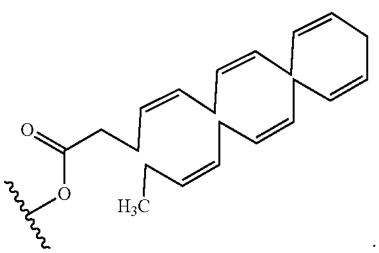

11. The compound of claim 1, or a stereoisomer thereof, wherein the stereoisomer of the compound is selected from the group consisting of:

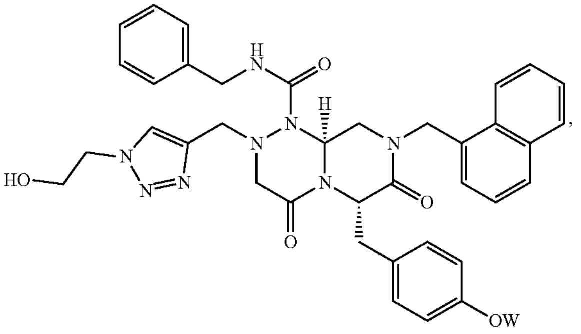

-continued

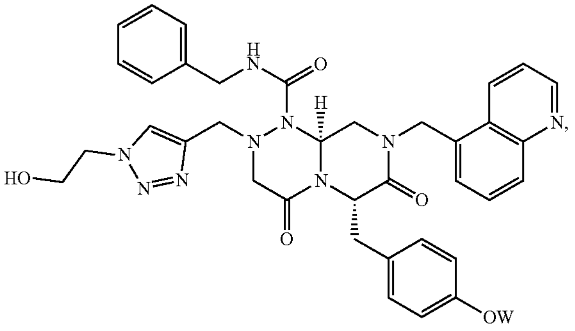

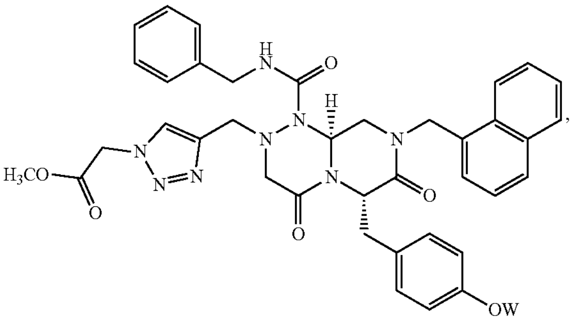

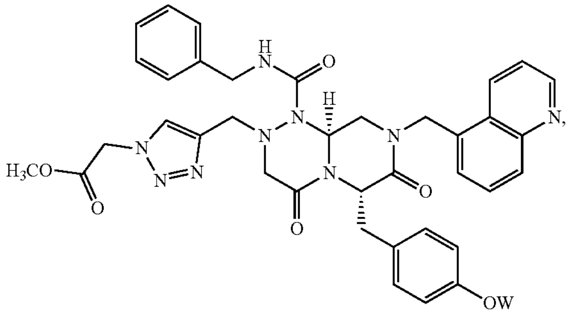

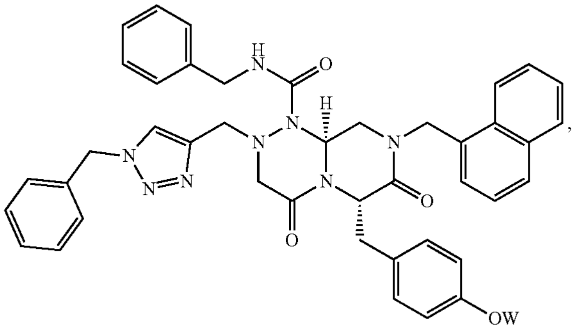

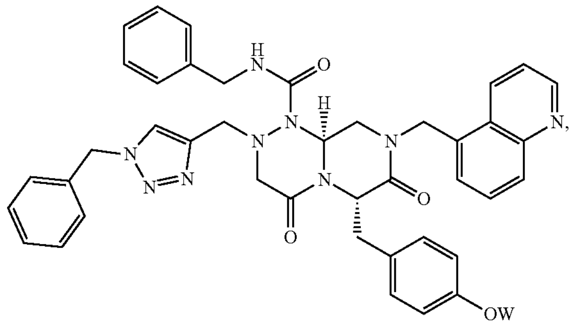

-continued
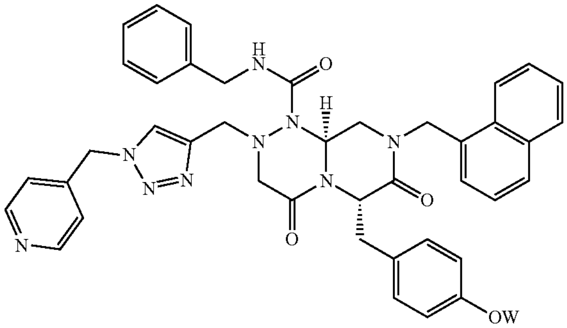
,
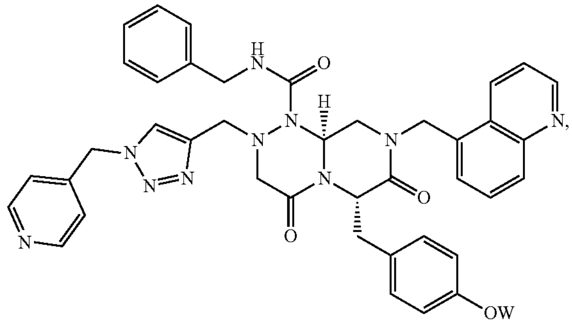
,
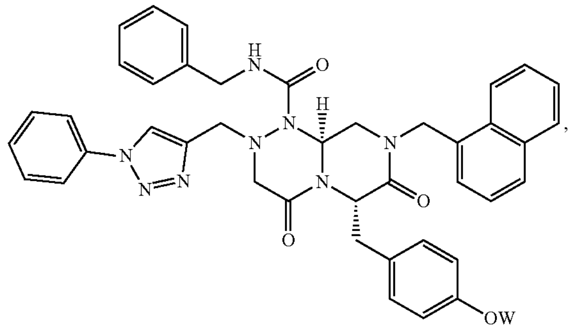
,
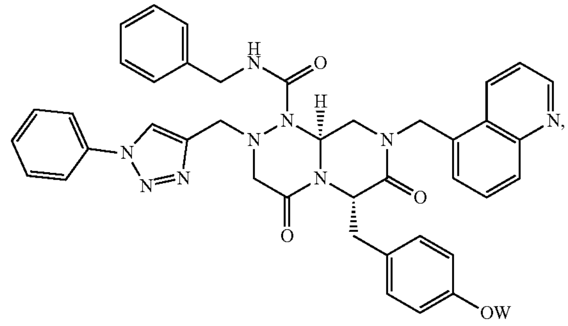
,
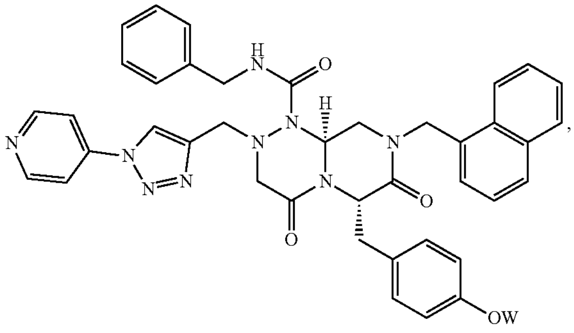
,
-continued
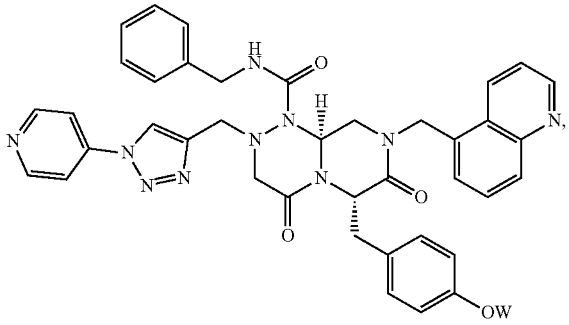
,
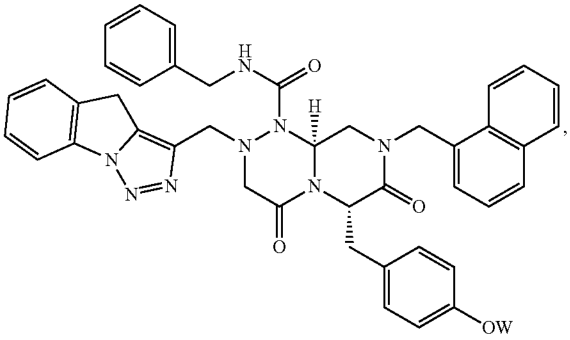
,
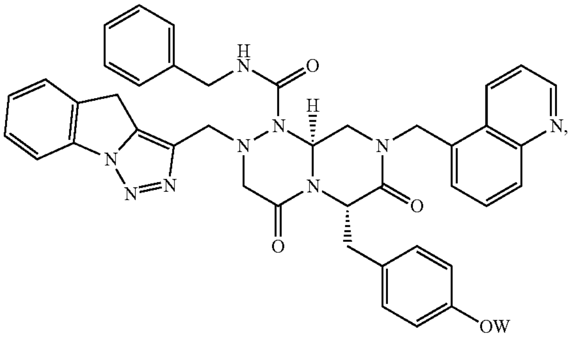
,
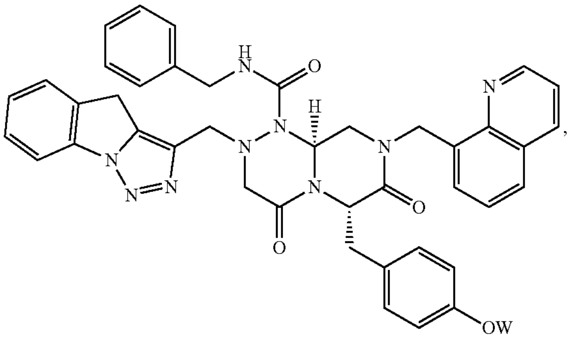
,
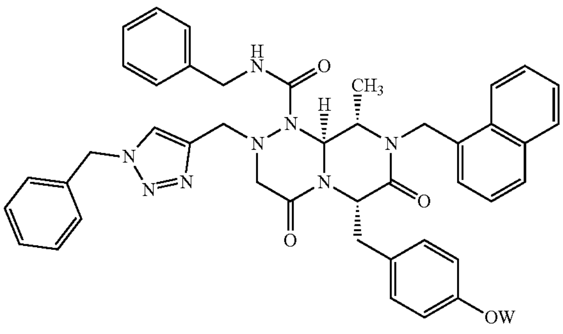
, -continued
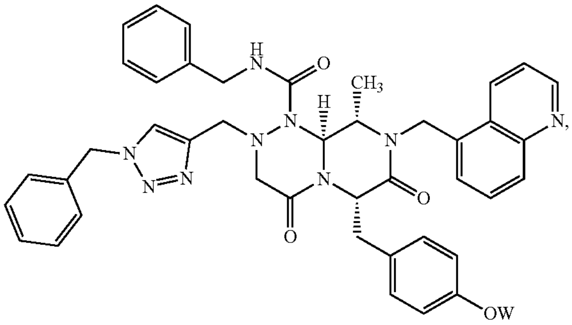
,
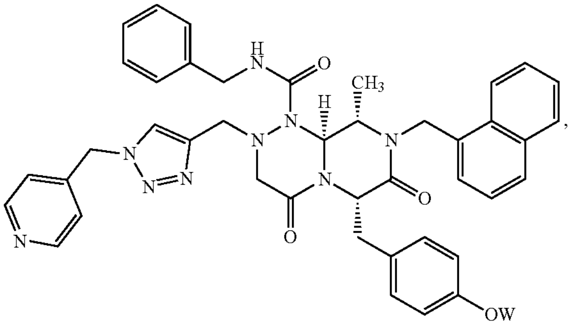
,
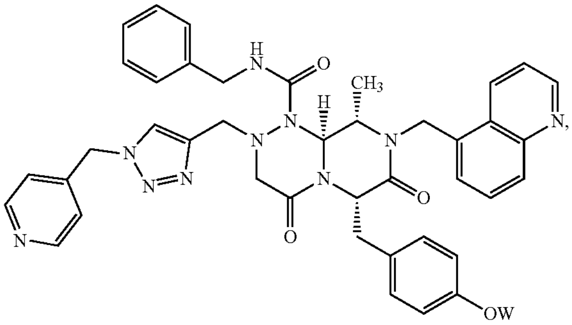
,
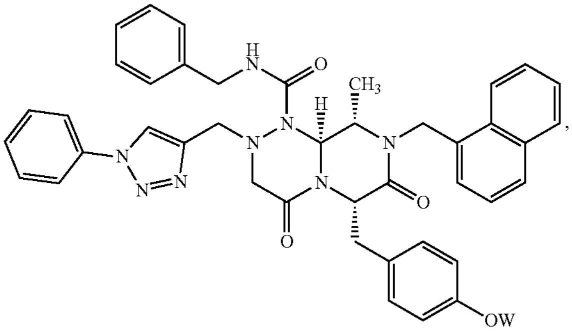
,
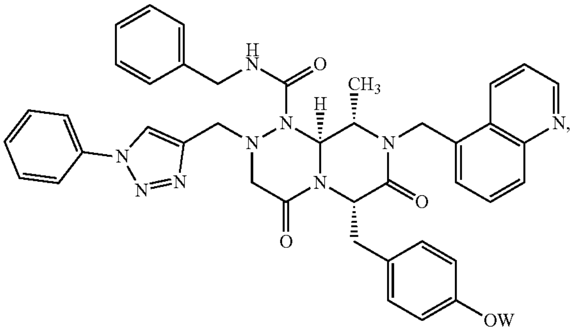
,
-continued
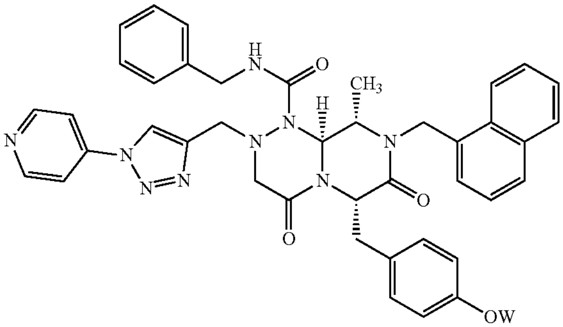
,
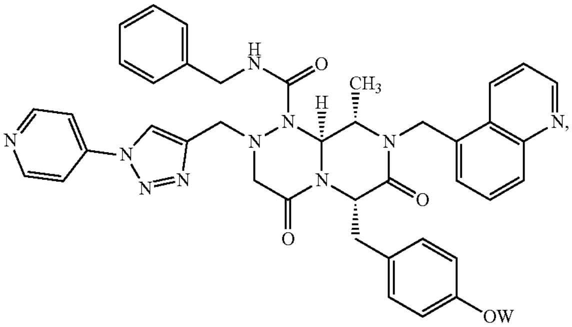
,
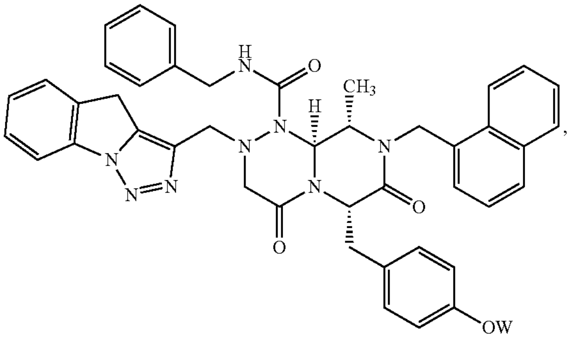
,
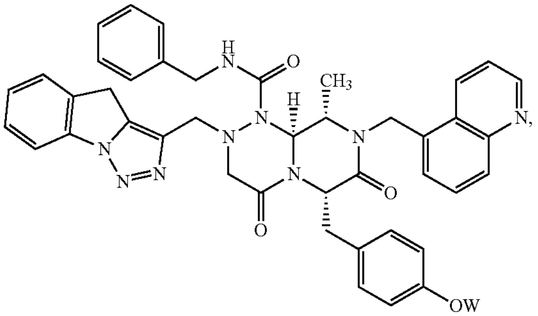
, and
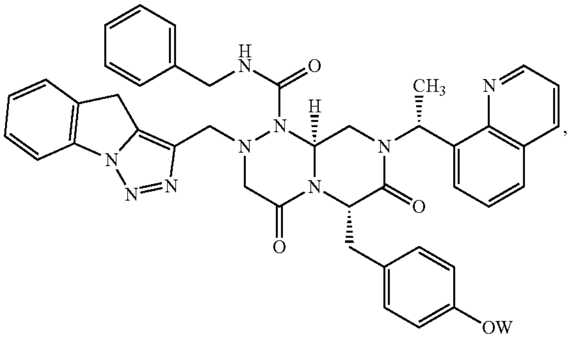
,
or a pharmaceutically acceptable salt thereof.

12. A pharmaceutical composition comprising a pharmaceutically acceptable carrier and a compound of claim 1, or a pharmaceutically acceptable salt or stereoisomer thereof.

13. A method for modulating cAMP-response element binding protein (CREB)/catenin signaling pathway in a warm blooded mammal or patient, wherein the method comprises administering to the warm blooded mammal or patient in need thereof a therapeutically effective amount of a compound of formula (Ia) or formula (Ic):

(Ia)

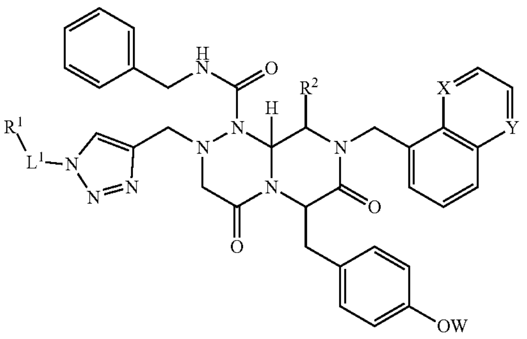

or (Ic)

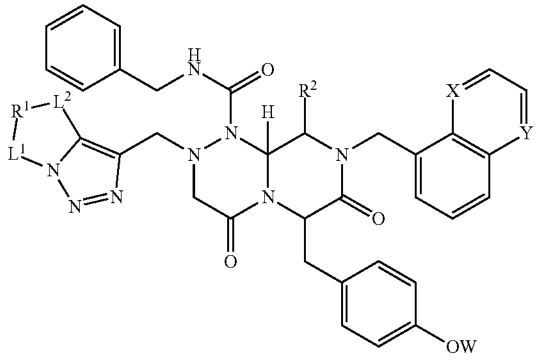

or a pharmaceutically acceptable salt or stereoisomer thereof, wherein:

$L^1$ is a bond, alkylene, heteroalkylene, cycloalkylene, heterocycloalkylene, arylene, or heteroarylene;

$R^1$ is H, halogen, CN, $NO_2$, alkyl, heteroalkyl, $CH_2X^1$, $CH(X^1)_2$, $C(X^1)_3$, $C(O)R^{1A}$, $C(O)OR^{1A}$, $C(O)NR^{1A}R^{1B}$, $C(O)NHNR^{1A}R^{1B}$, $NR^{1A}R^{1B}$, $NR^{1A}C(O)R^{1B}$, $NR^{1A}C(O)OR^{1B}$, $NR^{1A}OR^{1B}$, $NR^{1A}S(O)_2R^{1B}$, $NHC(O)NR^{1A}R^{1B}$, $NHNR^{1A}R^{1B}$, $N_3$, $OCH_2X^1$, $OCH(X^1)_2$, $OC(X^1)_3$, $OR^{1A}$, $SR^{1A}$, $S(O)R^{1A}$, $S(O)_2R^{1A}$, $S(O)_2NR^{1A}R^{1B}$, cycloalkyl, heterocycloalkyl, aryl, or heteroaryl;

$R^{1A}$ is H, alkyl, heteroalkyl, $CH_2X^1$, $CH(X^1)_2$, $C(X^1)_3$, C(O)OH, $C(O)NH_2$, $NH_2$, NHC(O)H, NHC(O)OH, NHOH, $NHC(O)NH_2$, $NHC(O)NHNH_2$, $NHNH_2$, $NHS(O)_2H$, OH, $OCH_2X^1$, $OCH(X^1)_2$, $OC(X^1)_3$, $ONH_2$, $OS(O)_2OH$, SH, $S(O)_2NH_2$, $S(O)_2OH$, cycloalkyl, heterocycloalkyl, aryl, or heteroaryl;

$R^{1B}$ is H, alkyl, heteroalkyl, $CH_2X^1$, $CH(X^1)_2$, $C(X^1)_3$, C(O)OH, $C(O)NH_2$, $NH_2$, NHC(O)H, NHC(O)OH, NHOH, $NHC(O)NH_2$, $NHC(O)NHNH_2$, $NHNH_2$, $NHS(O)_2H$, OH, $OCH_2X^1$, $OCH(X^1)_2$, $OC(X^1)_3$, $ONH_2$, $OS(O)_2OH$, SH, $S(O)_2NH_2$, $S(O)_2OH$, cycloalkyl, heterocycloalkyl, aryl, or heteroaryl; or $R^{1A}$ and $R^{1B}$, together with the nitrogen atom to which they are bonded, form a heterocycloalkyl or heteroaryl;

each $X^1$ is independently halogen;

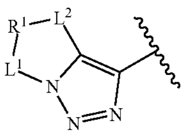 is 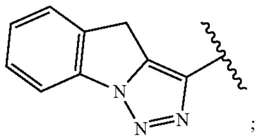 ;

$R^2$ is H or $C_1$-$C_4$ alkyl;

W is H, phosphate, a phosphate salt, an ester of an alkyl acid, or an ester of a fatty acid;

X is CH or N; and

Y is CH or N.

14. The method of claim 13, wherein the warm blooded mammal or patient has a disease or disorder associated with modulation of the cAMP-response element binding protein (CREB)/catenin signaling pathway selected from the group consisting of cancer, diabetes, and fibrosis.

15. The method of claim 14, wherein the fibrosis is selected from the group consisting of cardiac fibrosis, hepatic fibrosis, pulmonary fibrosis, renal fibrosis, and systemic fibrosis.

16. A cosmetic method for treating a skin condition in a warm blooded mammal or patient, wherein the method comprises topically or transdermally administering to the warm blooded mammal or patient in need thereof a cosmeceutically effective amount of a compound of formula (Ia) or formula (Ic):

(Ia)

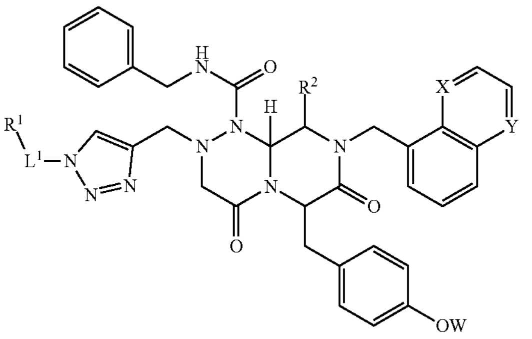

or (Ic)

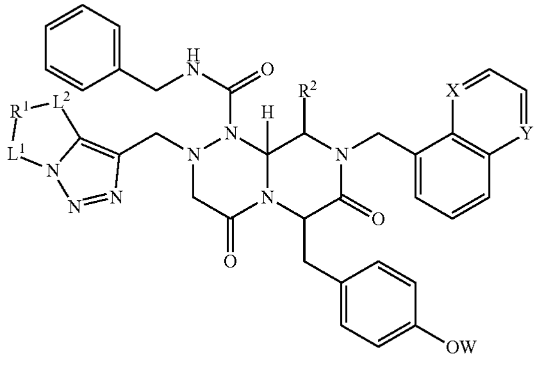

or a pharmaceutically acceptable salt or stereoisomer thereof, wherein:

$L^1$ is a bond, alkylene, heteroalkylene, cycloalkylene, heterocycloalkylene, arylene, or heteroarylene;

$R^1$ is H, halogen, CN, $NO_2$, alkyl, heteroalkyl, $CH_2X^1$, $CH(X^1)_2$, $C(X^1)_3$, $C(O)R^{1A}$, $C(O)OR^{1A}$, $C(O)NR^{1A}R^{1B}$, $C(O)NHNR^{1A}R^{1B}$, $NR^{1A}R^{1B}$, $NR^{1A}C(O)R^{1B}$, $NR^{1A}C(O)OR^{1B}$, $NR^{1A}OR^{1B}$, $NR^{1A}S(O)_2R^{1B}$, $NHC(O)NR^{1A}R^{1B}$, $NHNR^{1A}R^{1B}$, $N_3$, $OCH_2X^1$, $OCH(X^1)_2$, $OC(X^1)_3$, $OR^{1A}$, $SR^{1A}$, $S(O)R^{1A}$, $S(O)_2R^{1A}$, $S(O)_2NR^{1A}R^{1B}$, cycloalkyl, heterocycloalkyl, aryl, or heteroaryl;

$R^{1A}$ is H, alkyl, heteroalkyl, $CH_2X^1$, $CH(X^1)_2$, $C(X^1)_3$, C(O)OH, $C(O)NH_2$, $NH_2$, NHC(O)H, NHC(O)OH, NHOH, $NHC(O)NH_2$, $NHC(O)NHNH_2$, $NHNH_2$, $NHS(O)_2H$, OH, $OCH_2X^1$, $OCH(X^1)_2$, $OC(X^1)_3$, $ONH_2$, $OS(O)_2OH$, SH, $S(O)_2NH_2$, $S(O)_2OH$, cycloalkyl, heterocycloalkyl, aryl, or heteroaryl;

$R^{1B}$ is H, alkyl, heteroalkyl, $CH_2X^1$, $CH(X^1)_2$, $C(X^1)_3$, C(O)OH, $C(O)NH_2$, $NH_2$, NHC(O)H, NHC(O)OH, NHOH, $NHC(O)NH_2$, $NHC(O)NHNH_2$, $NHNH_2$, $NHS(O)_2H$, OH, $OCH_2X^1$, $OCH(X^1)_2$, $OC(X^1)_3$, $ONH_2$, $OS(O)_2OH$, SH, $S(O)_2NH_2$, $S(O)_2OH$, cycloalkyl, heterocycloalkyl, aryl, or heteroaryl; or $R^{1A}$ and $R^{1B}$, together with the nitrogen atom to which they are bonded, form a heterocycloalkyl or heteroaryl;

each $X^1$ is independently halogen;

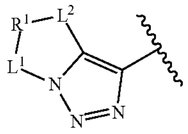
is
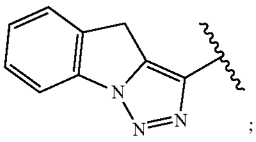
;

$R^2$ is H or $C_1$-$C_4$ alkyl;

W is H, phosphate, a phosphate salt, an ester of an alkyl acid, or an ester of a fatty acid;

X is CH or N; and

Y is CH or N.

17. The method of claim 16, wherein the skin condition is an aging skin condition.

18. The method of claim 17, wherein the aging skin condition is characterized by at least one attribute selected from the group consisting of acne, cracking, dryness, hyperpigmentation, loss of elasticity, loss of hair, loss of vibrance, redness, reduced cuticle growth, reduced nail growth, rosacea, scarring, sun damage, thinning, and wrinkles.

19. The method of claim 18, wherein the loss of hair is further characterized by loss of coloration of the hair.

20. The method of claim 16, wherein W is:

wherein m is 1, 2, 3, 4, 5, 6, 7, 8, 9, 10, 11, 12, 13, or 14;

(a)

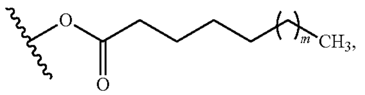

(b)

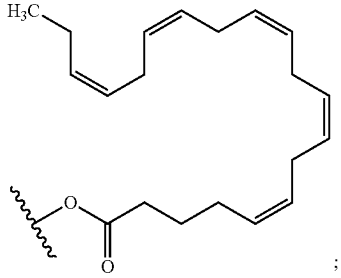

; or (c)

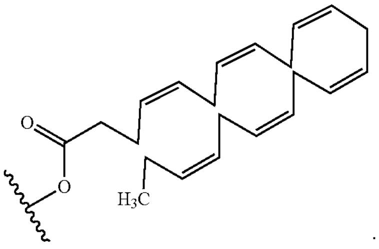

.

* * * * *